US009655729B2

(12) United States Patent
Parisi et al.

(10) Patent No.: US 9,655,729 B2
(45) Date of Patent: May 23, 2017

(54) TIBIAL BEARING COMPONENT FOR A KNEE PROSTHESIS WITH IMPROVED ARTICULAR CHARACTERISTICS

(71) Applicant: Zimmer, Inc., Warsaw, IN (US)

(72) Inventors: Raymond C. Parisi, Wakarusa, IN (US); Abraham P Habegger, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/062,262

(22) Filed: Mar. 7, 2016

(65) Prior Publication Data

US 2016/0184107 A1   Jun. 30, 2016

Related U.S. Application Data

(63) Continuation of application No. 14/284,028, filed on May 21, 2014, now Pat. No. 9,295,558, which is a continuation of application No. 13/459,056, filed on Apr. 27, 2012, now Pat. No. 8,764,838.

(60) Provisional application No. 61/561,657, filed on Nov. 18, 2011, provisional application No. 61/577,293, filed on Dec. 19, 2011, provisional application No. 61/592,576, filed on Jan. 30, 2012, provisional application No. 61/621,361, filed on Apr. 6, 2012, provisional application No. 61/621,363, filed on Apr. 6, 2012, provisional application No. 61/621,364, filed on Apr. 6, 2012, provisional application No. 61/621,366, filed on Apr. 6, 2012.

(51) Int. Cl.
  *A61F 2/38* (2006.01)
  *A61F 2/30* (2006.01)

(52) U.S. Cl.
  CPC .......... *A61F 2/3868* (2013.01); *A61F 2/389* (2013.01); *A61F 2/3886* (2013.01); *A61F 2002/30604* (2013.01); *A61F 2002/30616* (2013.01)

(58) Field of Classification Search
  CPC .......... A61F 2/389; A61F 2002/30604; A61F 2002/30616
  See application file for complete search history.

(56) References Cited

U.S. PATENT DOCUMENTS

5,047,057 A  9/1991  Lawes
5,059,216 A  10/1991  Winters
(Continued)

FOREIGN PATENT DOCUMENTS

CA      2856070 C     7/2016
CN    101214175 A     7/2008
(Continued)

OTHER PUBLICATIONS

"U.S. Appl. No. 14/918,721, Preliminary Amendment filed Oct. 23, 2015", 8 pgs.
(Continued)

*Primary Examiner* — Brian Dukert
(74) *Attorney, Agent, or Firm* — Schwegman Lundberg & Woessner, P.A.

(57) ABSTRACT

An orthopedic knee prosthesis includes a tibial bearing component with articular features which operate to protect adjacent soft tissues of the natural knee, promote and/or accommodate desired articulation with an abutting femoral component, and facilitate expedient and effective implantation by a surgeon.

21 Claims, 26 Drawing Sheets

(56) References Cited

U.S. PATENT DOCUMENTS

| | | |
|---|---|---|
| 5,171,283 A | 12/1992 | Pappas et al. |
| 5,192,328 A | 3/1993 | Winters |
| 5,219,362 A | 6/1993 | Tuke et al. |
| 5,282,870 A | 2/1994 | Moser et al. |
| 5,387,240 A | 2/1995 | Pottenger et al. |
| 5,413,604 A | 5/1995 | Hodge |
| 5,609,639 A | 3/1997 | Walker |
| 5,609,643 A | 3/1997 | Colleran et al. |
| 5,658,342 A | 8/1997 | Draganich et al. |
| 6,013,103 A | 1/2000 | Kaufman et al. |
| 6,068,658 A | 5/2000 | Insall et al. |
| 6,080,195 A | 6/2000 | Colleran et al. |
| 6,102,954 A | 8/2000 | Albrektsson et al. |
| 6,123,729 A | 9/2000 | Insall et al. |
| 6,203,576 B1 | 3/2001 | Afriat et al. |
| 6,210,443 B1 | 4/2001 | Marceaux et al. |
| 6,325,828 B1 | 12/2001 | Dennis et al. |
| 6,406,497 B2 | 6/2002 | Takei |
| 6,428,577 B1 | 8/2002 | Evans |
| 6,491,726 B2 | 12/2002 | Pappas |
| 6,558,426 B1 | 5/2003 | Masini |
| 6,660,039 B1 | 12/2003 | Evans et al. |
| 7,081,137 B1 | 7/2006 | Servidio |
| 7,160,330 B2 | 1/2007 | Axelson, Jr. et al. |
| 7,261,740 B2 | 8/2007 | Tuttle |
| 7,264,635 B2 | 9/2007 | Suguro |
| 7,309,362 B2 | 12/2007 | Yasuda et al. |
| 7,326,252 B2 | 2/2008 | Otto et al. |
| 7,351,263 B2 | 4/2008 | Afriat |
| 7,413,577 B1 | 8/2008 | Servidio |
| 7,625,407 B2 | 12/2009 | Akizuki |
| 7,635,390 B1 | 12/2009 | Bonutti |
| 7,678,152 B2 | 3/2010 | Suguro et al. |
| 7,776,085 B2 | 8/2010 | Bernero et al. |
| 8,690,954 B2 | 4/2014 | Parisi et al. |
| 8,764,838 B2 | 7/2014 | Parisi et al. |
| 8,858,643 B2 | 10/2014 | Parisi et al. |
| 9,072,607 B2 | 7/2015 | Parisi et al. |
| 9,186,255 B2 | 11/2015 | Parisi |
| 9,204,970 B2 | 12/2015 | Parisi et al. |
| 9,295,558 B2 | 3/2016 | Parisi et al. |
| 2004/0186582 A1 | 9/2004 | Yasuda et al. |
| 2004/0243244 A1 | 12/2004 | Otto et al. |
| 2005/0055102 A1 | 3/2005 | Tornier et al. |
| 2005/0096747 A1 | 5/2005 | Tuttle et al. |
| 2005/0197710 A1 | 9/2005 | Naegerl |
| 2005/0209701 A1 | 9/2005 | Suguro et al. |
| 2006/0004460 A1 | 1/2006 | Engh et al. |
| 2006/0265080 A1 | 11/2006 | McMinn |
| 2007/0185581 A1 | 8/2007 | Akizuki et al. |
| 2007/0233269 A1 | 10/2007 | Steines et al. |
| 2008/0119940 A1 | 5/2008 | Otto et al. |
| 2008/0161918 A1 | 7/2008 | Fankhauser et al. |
| 2008/0243258 A1 | 10/2008 | Sancheti |
| 2008/0288080 A1 | 11/2008 | Sancheti |
| 2008/0300689 A1 | 12/2008 | Mc Kinnon et al. |
| 2008/0300690 A1 | 12/2008 | Burstein et al. |
| 2009/0043395 A1 | 2/2009 | Hotokebuchi et al. |
| 2009/0204222 A1* | 8/2009 | Burstein .............. A61B 17/157 623/20.34 |
| 2009/0210066 A1 | 8/2009 | Jasty |
| 2009/0222103 A1 | 9/2009 | Fitz et al. |
| 2009/0265011 A1 | 10/2009 | Mandell |
| 2009/0265013 A1 | 10/2009 | Mandell |
| 2009/0319047 A1 | 12/2009 | Walker |
| 2009/0319048 A1 | 12/2009 | Shah et al. |
| 2009/0319049 A1 | 12/2009 | Shah et al. |
| 2009/0326663 A1 | 12/2009 | Dun |
| 2009/0326665 A1 | 12/2009 | Wyss et al. |
| 2009/0326666 A1 | 12/2009 | Wyss et al. |
| 2009/0326668 A1 | 12/2009 | Dun |
| 2010/0016976 A1 | 1/2010 | Siebel |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0191341 A1 | 7/2010 | Byrd |
| 2010/0262253 A1 | 10/2010 | Cipolletti et al. |
| 2010/0286788 A1 | 11/2010 | Komistek |
| 2010/0305708 A1 | 12/2010 | Lang |
| 2010/0329530 A1 | 12/2010 | Lang et al. |
| 2011/0022179 A1 | 1/2011 | Andriacchi et al. |
| 2011/0029091 A1 | 2/2011 | Bojarski et al. |
| 2011/0082558 A1 | 4/2011 | Kim et al. |
| 2011/0125278 A1 | 5/2011 | Bercovy et al. |
| 2011/0144760 A1 | 6/2011 | Wong et al. |
| 2011/0251695 A1 | 10/2011 | Lenz et al. |
| 2012/0185054 A1 | 7/2012 | Maloney et al. |
| 2013/0131816 A1 | 5/2013 | Parisi et al. |
| 2013/0131817 A1 | 5/2013 | Parisi et al. |
| 2013/0131818 A1 | 5/2013 | Parisi et al. |
| 2013/0131819 A1 | 5/2013 | Parisi et al. |
| 2014/0163687 A1 | 6/2014 | Parisi et al. |
| 2014/0257505 A1 | 9/2014 | Parisi et al. |
| 2015/0005890 A1 | 1/2015 | Parisi et al. |
| 2015/0282936 A1 | 10/2015 | Parisi et al. |
| 2016/0038294 A1 | 2/2016 | Parisi et al. |
| 2016/0045322 A1 | 2/2016 | Parisi et al. |

FOREIGN PATENT DOCUMENTS

| | | |
|---|---|---|
| CN | 104066402 A | 9/2014 |
| EP | 0636353 A1 | 2/1995 |
| EP | 0592750 B1 | 1/1999 |
| EP | 1025818 A2 | 8/2000 |
| EP | 1378216 A2 | 1/2004 |
| EP | 1477143 A1 | 11/2004 |
| EP | 1568336 A1 | 8/2005 |
| EP | 1719478 A2 | 11/2006 |
| EP | 1722721 A1 | 11/2006 |
| EP | 1354571 B1 | 6/2007 |
| EP | 1604623 B1 | 6/2008 |
| EP | 0927009 B1 | 1/2009 |
| EP | 1696835 B1 | 2/2009 |
| EP | 1591082 B1 | 9/2009 |
| EP | 2140838 A2 | 1/2010 |
| EP | 2143403 A1 | 1/2010 |
| EP | 1555962 B1 | 2/2011 |
| EP | 2324799 A2 | 5/2011 |
| EP | 2335654 A1 | 6/2011 |
| FR | 2852819 A1 | 10/2004 |
| JP | 06203576 A | 7/1994 |
| JP | 2004166802 A | 6/2004 |
| JP | 2007509709 A | 4/2007 |
| JP | 2010188051 A | 9/2010 |
| JP | 2012531265 A | 12/2012 |
| JP | 2015502203 A | 1/2015 |
| WO | WO-9514446 A1 | 6/1995 |
| WO | WO-2004058108 A1 | 7/2004 |
| WO | WO-2005051240 A1 | 6/2005 |
| WO | WO-2005122967 A1 | 12/2005 |
| WO | WO-2006058057 A2 | 6/2006 |
| WO | WO-2006092167 A1 | 9/2006 |
| WO | WO-2007109641 A2 | 9/2007 |
| WO | WO-2009088235 A2 | 7/2009 |
| WO | WO-2009088236 A2 | 7/2009 |
| WO | WO-2009088238 A2 | 7/2009 |
| WO | WO-2009105495 A1 | 8/2009 |
| WO | WO-2010001010 A1 | 1/2010 |
| WO | WO-2011072235 A2 | 6/2011 |
| WO | WO-2012112698 A2 | 8/2012 |
| WO | WO-2013074142 A1 | 5/2013 |
| WO | WO-2013074143 A1 | 5/2013 |
| WO | WO-2013074144 A1 | 5/2013 |
| WO | WO-2013074145 A1 | 5/2013 |

OTHER PUBLICATIONS

"U.S. Appl. No. 14/926,281, Preliminary Amendment filed Oct. 30, 2015", 8 pgs.

"Chinese Application Serial No. 201280067481.7, Office Action mailed Sep. 30, 2015", (W/ English Translation), 7 pgs.

"European Application Serial No. 12718883.7, Communication Pursuant to Article 94(3) EPC mailed Dec. 2, 2015", 4 pgs.

(56) References Cited

OTHER PUBLICATIONS

"European Application Serial No. 12718883.7, Communication Pursuant to Rules 161(1) and 162 EPC mailed Jul. 31, 2014", 2 pgs.
"Japanese Application Serial No. 2014-542297, Office Action mailed Nov. 24, 2015", (W/ English Translation) 10 pgs.
"U.S. Appl. No. 13/459,037, Final Office Action mailed Sep. 23, 2013", 9 pgs.
"U.S. Appl. No. 13/459,037, Non Final Office Action mailed Apr. 23, 2013", 10 pgs.
"U.S. Appl. No. 13/459,037, Notice of Allowance mailed Jun. 13, 2014", 9 pgs.
"U.S. Appl. No. 13/459,037, Preliminary Amendment filed Apr. 27, 2012", 3 pgs.
"U.S. Appl. No. 13/459,037, Response filed Mar. 21, 2014 to Final Office Action mailed Sep. 23, 2013", 15 pgs.
"U.S. Appl. No. 13/459,037, Response filed Mar. 28, 2013 to Restriction Requirement mailed Feb. 26, 2013", 9 pgs.
"U.S. Appl. No. 13/459,037, Response filed Jul. 23, 2013 to Non Final Office Action mailed Apr. 23, 2013", 19 pgs.
"U.S. Appl. No. 13/459,037, Restriction Requirement mailed Feb. 26, 2013", 6 pgs.
"U.S. Appl. No. 13/459,041, Non Final Office Action mailed Jan. 15, 2014", 16 pgs.
"U.S. Appl. No. 13/459,041, Non Final Office Action mailed Sep. 9, 2014", 14 pgs.
"U.S. Appl. No. 13/459,041, Notice of Allowance mailed Apr. 2, 2015", 10 pgs.
"U.S. Appl. No. 13/459,041, Preliminary Amendment mailed Apr. 27, 2012", 7 pgs.
"U.S. Appl. No. 13/459,041, PTO Response to Rule 312 Communication mailed Jun. 9, 2015", 2 pgs.
"U.S. Appl. No. 13/459,041, Response filed May 15, 2014 to Non-Final Office Action dated Jan. 15, 2014", 24 pgs.
"U.S. Appl. No. 13/459,041, Response filed Sep. 23, 2013 to Restriction Requirement mailed Jul. 25, 2013", 18 pgs.
"U.S. Appl. No. 13/459,041, Response filed Dec. 9, 2014 to Non-Final Office Action mailed Sep. 9, 2014", 23 pgs.
"U.S. Appl. No. 13/459,041, Restriction Requirement mailed Jul. 25, 2013", 9 pgs.
"U.S. Appl. No. 13/459,048, Non Final Office Action mailed Jul. 11, 2013", 6 pgs.
"U.S. Appl. No. 13/459,048, Notice of Allowance mailed Nov. 26, 2013", 10 pgs.
"U.S. Appl. No. 13/459,048, Preliminary Amendment filed Apr. 27, 2012", 7 pgs.
"U.S. Appl. No. 13/459,048, Response filed Nov. 11, 2013 to Non-Final Office Action mailed Jul. 11, 2013", 16 pgs.
"U.S. Appl. No. 13/459,056, Examiner Interview Summary mailed Dec. 26, 2013", 3 pgs.
"U.S. Appl. No. 13/459,056, Non Final Office Action mailed Jul. 25, 2013", 11 pgs.
"U.S. Appl. No. 13/459,056, Notice of Allowance mailed Feb. 20, 2014", 5 pgs.
"U.S. Appl. No. 13/459,056, Preliminary Amendment filed Apr. 27, 2012", 7 pgs.
"U.S. Appl. No. 13/459,056, PTO Response to Rule 312 Communication mailed May 22, 2014", 2 pgs.
"U.S. Appl. No. 13/459,056, Response filed Jan. 24, 2014 to Non-Final office Action mailed Jul. 25, 2013", 27 pgs.
"U.S. Appl. No. 13/459,056, Response filed Apr. 8, 2013 to Restriction Requirement mailed Mar. 6, 2013", 15 pgs.
"U.S. Appl. No. 13/459,056, Restriction Requirement mailed Mar. 6, 2013", 6 pgs.
"U.S. Appl. No. 14/181,033, Non Final Office Action mailed May 1, 2015", 5 pgs.
"U.S. Appl. No. 14/181,033, Notice of Allowance mailed Jul. 17, 2015", 10 pgs.
"U.S. Appl. No. 14/181,033, Response filed Jun. 22, 2015 to Non-Final Office Action mailed May 1, 2015", 11 pgs.
"U.S. Appl. No. 14/284,028, Non Final Office Action mailed Jul. 7, 2015", 17 pgs.
"U.S. Appl. No. 14/284,028, Notice of Allowance mailed Nov. 6, 2015", 5 pgs.
"U.S. Appl. No. 14/284,028, Response filed Oct. 6, 2015 to Non Final Office Action mailed Jul. 7, 2015", 15 pgs.
"U.S. Appl. No. 14/284,028, Supplemental Preliminary Amendment filed Jul. 8, 2014", 13 pgs.
"U.S. Appl. No. 14/490,153, Final Office Action mailed Apr. 15, 2015", 18 pgs.
"U.S. Appl. No. 14/490,153, Non Final Office Action mailed Nov. 12, 2014", 9 pgs.
"U.S. Appl. No. 14/490,153, Notice of Allowance mailed Aug. 14, 2015", 10 pgs.
"U.S. Appl. No. 14/490,153, Preliminary Amendment filed Sep. 18, 2014", 3 pgs.
"U.S. Appl. No. 14/490,153, Response filed Feb. 18, 2015 to Non-Final Office Action mailed Nov. 12, 2014", 14 pgs.
"U.S. Appl. No. 14/490,153, Response filed Jul. 7, 2015 to Final Office Action mailed Apr. 15, 2015", 14 pgs.
"Bi-Cruciate Stabilized Knee System", Design Rationale, Smith & Nephew Journal, (2006), 20 pgs.
"Canadian Application Serial No. 2,856,070, Preliminary Amendment filed May 25, 2015", 27 pgs.
"Complete Knee Solution Surgical Technique for the CR-Flex Fixed Bearing Knee", Zimmer Nexgen, (2003), 22 pgs.
"European Application Serial No. 12718882.9 Response filed Feb. 10, 2015 to Communication Pursuant to Rules 161(1) and 162 EPC mailed Jul. 31, 2014", 11 pgs.
"European Application Serial No. 127188837, Response filed Feb. 10, 2015 to Communication Pursuant to Rules 161(1) and 162 EPC mailed Jul. 31, 2014", 16 pgs.
"European Application Serial No. 12719236.7 Response filed Feb. 9, 2015 to Communication Pursuant to Rules 161(1) and 162 EPC mailed Jul. 30, 2014", 10 pgs.
"European Application Serial No. 12720352.9 Response filed Feb. 9, 2015 to Communication Pursuant to Rules 161(1) and 162 EPC mailed Jul. 30, 2014", 10 pgs.
"Extramedullary/Intramedullary Tibial Resector: Surgical Technique", Nexgen Complete Knee Solution, Zimmer, Inc. 97-5997-02 Rev 1, (2000, 2002), 25 pgs.
"Extramedullary/Intramedullary Tibial Resector: Surgical Technique", Nexgen Complete Knee Solution, Zimmer, Inc. 97-5997-002-00 Rev. 2, (2000, 2008, 2009), 28 pgs.
"Gender Solutions Natural Knee Flex System: Because Men and Women are Different", Zimmer, Inc., (2007, 2009), 6 pg.
"Gender Solutions Natural Knee Flex System: Surgical Technique", Zimmer, Inc., (2007, 2008, 2009), 36 pgs.
"International Application Serial No. PCT/US2012/035679, International Preliminary Report on Patentability mailed May 30, 2014", 8 pgs.
"International Application Serial No. PCT/US2012/035679, International Search Report mailed Jun. 8, 2012", 4 pgs.
"International Application Serial No. PCT/US2012/035679, Written Opinion mailed Jun. 8, 2012", 7 pgs.
"International Application Serial No. PCT/US2012/035680, International Preliminary Report on Patentability mailed May 30, 2014", 13 pgs.
"International Application Serial No. PCT7US2012/035680, Search Report mailed Oct. 9, 2012", 7 pgs.
"International Application Serial No. PCT/US2012/035680, Written Opinion mailed Oct. 9, 2012", 11 pgs.
"International Application Serial No. PCT/US2012/035683, International Preliminary Report on Patentability mailed May 30, 2014", 9 pgs.
"International Application Serial No. PCT/US2012/035683, International Search Report and Written Opinion mailed Jun. 5, 2012", 12 pgs.
"International Application Serial No. PCT/US2012/035684, International Preliminary Report on Patentability mailed May 30, 2014", 14 pgs.
"International Application Serial No. PCT/US2012/035684, International Search Report mailed Aug. 8, 2012", 9 pgs.

(56) References Cited

OTHER PUBLICATIONS

"International Application Serial No. PCT/US2012/035684, Written Opinion mailed Jun. 8, 2012", 12 pgs.
"Intramedullary Instrumentation Surgical Technique for the NexGen Cruciate Retaining & Legacy Posterior Stabilized Knee", Zimmer, Inc. Nexgen Complete Knee Solution, 97-5973-102, Rev. 1, (1995,1997,1998), 36 pgs.
"Japanese Application Serial No. 2014-542297, Office Action mailed Jun. 30, 2015", (W/ English Translation), 10 pgs.
"Legacy Implant Options", Nexgen Complete Knee Solution, (2002), 8 pgs.
"LPS-Flex Fixed Bearing Knee: Surgical Technique", Zimmer, Inc., (2004, 2007, 2008), 16 pgs.
"MIS Minimally Invasive Solution, The M/G Unicompartmental Knee Minimally Invasive Surgical Technique", Zimmer, Inc. Nexgen Complete Knee Solution, 97-5791-02, (Aug. 14, 2008), 27 pgs.
"Multi-Reference 4-in-1 Femoral Instrumentation Surgical Technique for NexGen Cruciate Retaining & NexGen Legacy Posterior Stabilized Knees", Zimmer, Inc. Nexgen Complete Knee Solution, 97-5973-402 Rev. 1, (1998, 2000), 18 pgs.
"Natural-Knee II Primary System Surgical Technique", Zimmer, Inc., (2005), 48 pgs.
"Nexgen Complete Knee Solution for the Legacy Knee LPS-Flex Fixed Bearing Knee", Zimmer Surgical Technique, 97-5964-102-00, (2004, 2007), 12 pgs.
"NexGen Complete Knee Solution, Intramedullary Instrumentation Surgical Technique for the NexGen Cruciate Retaining & Legacy Posterior Stabilized Knee", Zimmer, Inc., (1995, 1997, 1998), 1-33.
"NexGen Implant Options Surgeon-Specific", Zimmer Inc., (2000), 16 pgs.
"NexGen LPS Fixed Knee: Surgical Technique", Zimmer Inc., (2002, 2008), 44 pgs.
"NexGen LPS-Flex Mobile and LPS-Mobile Bearing Knees", Zimmer, Inc., (2007, 2008), 4 pgs.
"NexGen Trabecular Metal Modular Plates", Zimmer Inc., (2007), 19 pgs.
"Primary/Revision Surgical Technique for NexGen Rotating Hinge Knee (RHK)", Zimmer, Inc, Nexgen Complete Knee Solution, 97-5880-02, (2002), 116 pgs.
"Revision Instrumentation Surgical Technique for Legacy Knee Constrained Condylar Knee", Zimmer, Inc. Nexgen Complete Knee Solution, 97-5994-202, (2001), 61 pgs.
"Surgical Technique for Cruciate Retaining Knees and Revision Instrumentation Surgical Technique for Cruciate Retaining Augmentable Knees", Zimmer, Inc. Nexgen Complete Knee Solution, 97-5970-202, (2002), 130 pgs.
"Surgical Technique for the CR-Flex Fixed Bearing Knee", NexGen Complete Knee Solution, Zimmer, Inc., (2003), 22 pgs.
"Surgical Technique for the Legacy Knee LPS-Flex Bearing Knee", Zimmer, Inc. Nexgen Complete Knee Solution, 97-5964-02, Rev. 1, (2000, 2002), 15 pgs.
"Surgical Technique for the Legacy Posterior Stabilized Knees", Zimmer, Inc. Nexgen Complete Knee Solution, 97-5996-02, (2002), 43 pgs.
"Surgical Technique—Nexgen Complete Knee Solution for the Legacy Knee LPS-Flex Fixed Bearing Knee", Zimmer, Inc., (2004, 2007), 12 pgs.
"The Zimmer Institute Surgical Technique MIS Quad-Sparing Surgical Technique for Total Knee Arthroplasty", NExGen Complete Knee Solution, (2004), 55 pgs.
"Trabecular Metal Monoblock Tibial Components Surgical Technique Addendum", Nexgen Zimmer, Inc., (2005, 2007), 12 pgs.
"Trabecular Metal Tibial Tray: Surgical Technique", NexGen Zimmer, Inc., (2007, 2009), 16 pgs.
"Zimmer MIS Intramedullary Instrumentation Surgical Technique for NexGen Cruciate Retaining & NexGen Legacy Posterior Stabilized Knees", printed 2005, 2009, Zimmer, Inc., (2009), 45 pgs.
"Zimmer Nexgen Cruciate Retaining (CR) and Legacy Knee Posterior Stabilized (LPS) Trabecular Metal Monoblock Tibias", Zimmer, Inc Surgical Technique Addendum, 97-7253-34, Rev. 3, (2004), 11 pgs.
"Zimmer NexGen CR-Flex and LPS-Flex Knees Surgical Technique with posterior Referencing Instrumentation,", Zimmer Inc., (2010, 2011), 48 pgs.
"Zimmer NexGen LCCK Surgical Technique for use with LCCK 4-in-1 Instrumentation", Zimmer, Inc.; copyright 2009, 2010, 2011, (May 2011), 52 pgs.
"Zimmer NexGen MIS Modular Tibial Plate and Keel Cemented Surgical Technique", Zimmer Inc., (2006, 2011), 26 pgs.
"Zimmer NexGen MIS Tibial Component", Brochure-97-5950-001-00 7.5mm, (2005, 2006), 8 pgs.
"Zimmer NexGen MIS Tibial Component Cemented Surgical Technique", Zimmer, Inc, #97-5950-002-00 Rev.1 1.5ML, (2005), 14 pgs.
"Zimmer NexGen MIS Tibial Component Cemented Surgical Technique", Zimmer Inc., (2005, 2006, 2008, 2009, 2010), 16 pgs.
"Zimmer NexGen Trabecular Metal Augments—Abbreviated Surgical Technique", Zimmer, Inc., (2004, 2006), 6 pgs.
"Zimmer NexGen Trabecular Metal Augments Surgical Technique for LCCK & Rotating Hing Knee Trabecular Metal Augments". Zimmer. Inc. 97-5448-02, Rev. 1, (2004), 6 pgs.
"Zimmer NexGen Trabecular Metal Primary Patella Surgical Technique", Zimmer. Inc., 97-7255-112-00, (2005), 10 pgs.
"Zimmer NexGen Trabecular Metal Tibial Tray", Surgical Technique, Zimmer, Inc., (2007, 2009), 16 pgs.
"Zimmer Patient Specific Instruments", Surgical Techniques for NexGen Complete Knee Solution Zimmer, Inc., (2010), 16 pgs.
Hofmann, Aaron A, et al., "Posterior Stabilization in Total Knee Arthroplasty with Use of an Ultracongruent Polyethylene", The Journal of Arthroplasty vol. 15, No. 5, (2000), 576-583.
Partovi, Hamid, "Flow-Through Latch and Edge-Triggered Flip-Flop Hybrid Elements", Proceedings of the IEEE International Solid-State Circuits Conference, Digest of Technical Papers and Slide Supplement, NexGen Inc., Milpitas, CA, (1996), 40 pgs.
"U.S. Appl. No. 14/918,721, Final Office Action mailed Oct. 20, 2016", 5 pgs.
"U.S. Appl. No, 14/918,721, Non Final Office Action mailed Jun. 16, 2016", 6 pgs.
"U.S. Appl. No. 14/918,721, Response filed Sep. 12, 2016 to Non Final Office Action mailed Jun. 16, 2016", 12 pgs.
"European Application Serial No. 12718882.9, Response filed Apr. 11, 2016 to Communication Pursuant to Article 94(3) EPC mailed Dec. 1, 2015", 12 pgs.
"European Application Serial No. 12718882.9, Communication Pursuant to Article 94(3) EPC mailed Dec. 1, 2015", 11 pgs.
"European Application Serial No. 12718883.7, Response filed Apr. 12, 2016 to Communication Pursuant to Article 94(3) EPC mailed Dec. 2, 2015", 30 pgs.
"European Application Serial No. 12718883.7, Intention to Grant mailed May 20, 2016", 5 pgs.
"European Application Serial No. 12719236.7, Decision to Grant mailed Feb. 18, 2016", 3 pgs.
"European Application Serial No. 12719236.7, Office Action mailed Aug. 27, 2015", 7 pgs.
"Japanese Application Serial No. 2014-542297, Office Action mailed May 31, 2016", W/ English Translation of Claims, 6 pgs.
"Japanese Application Serial No. 2014-542297, Response filed Feb. 23, 2016 to Office Action mailed Nov. 24, 2015", W/ English Translation Of Claims, 15 pgs.
"Japanese Application Serial No. 2014-542297, Response filed Jun. 8, 2016 to Office Action mailed May 31, 2016", W/ English Translation Of Claims, 14 pgs.
"Japanese Application Serial No. 2014-542297, Response filed Sep. 28, 2015 to Office Action mailed Jun. 30, 2015", W/ English Translation of Claims, 16 pgs.

\* cited by examiner

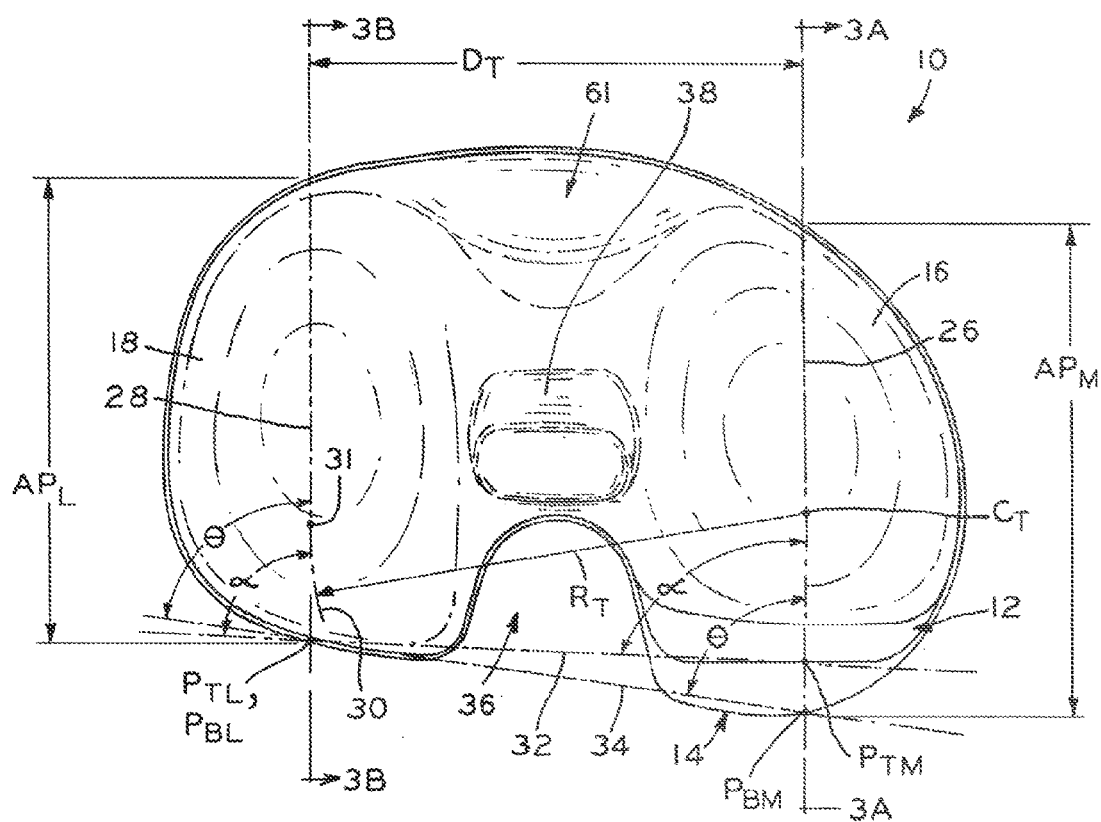
FIG_1A

TIBIAL BEARING COMPONENT FOR A KNEE PROSTHESIS WITH IMPROVED ARTICULAR CHARACTERISTICS

CROSS-REFERENCE TO RELATED APPLICATIONS

This application is a continuation of U.S. patent application Ser. No. 14/284,028 filed May 21, 2014, which is a continuation of U.S. patent application Ser. No. 13/459,056 filed Apr. 27, 2012, now issued as U.S. Pat. No. 8,764,838, which claims the benefit under Title 35, U.S.C. §119(e) of U.S. Provisional Patent Application Ser. No. 61/561,657 filed Nov. 18, 2011, U.S. Provisional Patent Application Ser. No. 61/577,293 filed Dec. 19, 2011, U.S. Provisional Patent Application Ser. No. 61/592,576 filed Jan. 30, 2012, U.S. Provisional Patent Application Ser. No. 61/621,361 filed Apr. 6, 2012, U.S. Provisional Patent Application Ser. No. 61/621,363 filed Apr. 6, 2012, U.S. Provisional Patent Application Ser. No. 61/621,364 filed Apr. 6, 2012, and U.S. Provisional Patent Application Ser. No. 61/621,366 filed Apr. 6, 2012, each entitled TIBIAL BEARING COMPONENT FOR A KNEE PROSTHESIS WITH IMPROVED ARTICULAR CHARACTERISTICS, the entire disclosures of which are hereby expressly incorporated by reference herein.

BACKGROUND

1. Technical Field

The present disclosure relates to orthopaedic prostheses and, specifically, to articular tibial components in a knee prosthesis.

2. Description of the Related Art

Orthopaedic prostheses are commonly utilized to repair and/or replace damaged bone and tissue in the human body. For a damaged knee, a knee prosthesis may be implanted using a tibial baseplate, a tibial bearing component, and a distal femoral component. The tibial baseplate is affixed to a proximal end of the patient's tibia, which is typically resected to accept the baseplate. The femoral component is implanted on a distal end of the patient's femur, which is also typically resected to accept the femoral component. The tibial bearing component is placed between the tibial baseplate and femoral component, and may be fixed upon or slidably coupled to the tibial baseplate.

The tibial bearing component, which may also be referred to as a tibial insert or meniscal component, provides an articular surface which interacts with the adjacent femur or femoral component during extension and flexion of the knee. The features and geometry of the articular surface influences the articular characteristics of the knee, such as by defining maximum knee flexion, internal/external rotation, femoral rollback, and behavior of the knee prosthesis in hyperextension, for example. Accordingly, substantial design efforts have previously focused on providing knee prosthesis components which preserve flexion range and promote a desired kinematic motion profile for the widest possible range of prospective knee replacement patients.

SUMMARY

The present disclosure provides an orthopaedic knee prosthesis including a tibial bearing component with articular features which operate to protect adjacent soft tissues of the natural knee, promote and/or accommodate desired articulation with an abutting femoral component, and facilitate expedient and effective implantation by a surgeon.

Features which accommodate and protect soft tissues of the knee include 1) a relief or scallop formed in the proximal peripheral edge of the bearing component near an anterior/lateral corner thereof; and 2) a bulbous, convex flare protruding from the tibial bearing component sidewall at an anterior/medial portion thereof.

Features which facilitate and/or promote improved articular characteristics include: 1) medial and lateral articular tracks, defined by respective dished articular compartments of the tibial bearing component, which are angled or "clocked" with respect to the posterior edge of the tibial bearing component; 2) a lateral articular compartment which defines a low conformity with the corresponding condyle of the abutting femoral component, and a medial articular compartment which defines a high conformity with the corresponding medial condyle of the femoral component; 3) medial and lateral articular tracks which, when viewed in respective sagittal planes, define a distal-most point which is anteriorly shifted with respect to predicate devices; 4) a lateral articular track which transitions from an early- and mid-flexion path that is generally linear along an anterior/posterior path as viewed in a transverse plane, to an arcuate path at the deep-flexion, posterior end of the articular track; 5) a lateral articular compartment which defines a relatively "flattened" posterior edge profile as compared to the posterior edge profile of the medial articular compartment to define a differential "jump height" therebetween; 6) for posterior-stabilized (PS) prostheses, a spine defining a posterior face which transitions from symmetrical in a proximal portion (i.e., a portion contacted by a femoral cam in early flexion) to an angled configuration in a distal portion (i.e., a portion contacted by the femoral cam in mid- to deep flexion); and 7) for ultra-congruent (UC) knee prostheses, a posterior eminence disposed between medial and lateral articular compartments that is sized and shaped to smoothly transition into a position within the intercondylar notch of an abutting femoral component when the knee prosthesis is hyperextended.

Features which facilitate surgical implantation include provision of families of tibial bearing components from winch the surgeon may choose intraoperatively. These families may include a range of component sizes, multiple components within a given size, and different component designs. For example, within a range of sizes, different components may feature varying clocking angles and/or levels of posterior "flattening" in the lateral articular compartment, as noted above. Within a given size, multiple components may feature differing thickness profiles, as viewed from a sagittal and/or coronal perspective, in order to selectively tilt or cant the articular surface. Moreover, various combinations of the design features described herein may be provided across several tibial bearing component designs, such as posterior-stabilized, ultra-congruent and cruciate-retaining designs.

According to one embodiment thereof, the present invention provides a tibial bearing component for articulation with medial and lateral femoral condyles, the tibial bearing component defining a tibial bearing component coordinate system comprising: a bearing component transverse plane extending along a medial/lateral direction and an anterior/posterior direction; a bearing component coronal plane extending along a proximal/distal direction and the medial/lateral direction, the bearing component coronal plane perpendicular to the bearing component transverse plane; and a bearing component sagittal plane extending along the anterior/posterior direction and the proximal/distal direction, the bearing component sagittal plane perpendicular to the bearing component transverse plane and the bearing component coronal plane, the tibial bearing component comprising: an articular surface and an opposing distal surface, the distal surface parallel to the bearing component transverse plane, the articular surface including medial and lateral dished articular compartments sized and shaped for articulation with the medial and lateral femoral condyles respectively, the medial and lateral dished articular compartments separated from one another by the bearing component sagittal plane, the articular and distal surfaces bounded by a tibial bearing periphery, the medial and lateral dished articular compartments having medial and lateral distal-most points defined as the points in the medial and lateral dished articular compartments, respectively, that are closest to the distal surface, and a posterior eminence extending proximally from the articular surface to define an eminence height of between 3.8 mm and 10 mm as measured from the distal-most points along the proximal/distal direction, the posterior eminence disposed between the medial and lateral dished articular compartments and extending anteriorly from a posterior edge of the tibial bearing periphery to define an anterior/posterior eminence extent equal to less than 30% of an overall anterior/posterior extent of the tibial bearing component, the posterior eminence comprising an eminence articular surface having a rounded shape in which a smallest radius of curvature defined by the eminence articular surface is greater than 1 mm.

According to another embodiment thereof, the present invention provides a tibial prosthesis for articulation with femoral condyles, the tibial prosthesis defining a tibial bearing component coordinate system comprising: a bearing component transverse plane extending along a medial/lateral direction and an anterior/posterior direction; a bearing component coronal plane extending along a proximal/distal direction and the medial/lateral direction, the bearing component coronal plane perpendicular to the bearing component transverse plane; and a bearing component sagittal plane extending along the anterior/posterior direction and the proximal/distal direction, the bearing component sagittal plane perpendicular to the bearing component transverse plane and the bearing component coronal plane, the tibial prosthesis comprising: a tibial baseplate comprising a bone-contacting surface and an opposed tibial bearing mounting surface, the bone-contacting surface and the tibial bearing mounting surface bounded by a baseplate periphery; and a tibial bearing component fixable to the tibial baseplate, the tibial bearing component comprising: an articular surface including medial and lateral dished articular compartments sized and shaped for articulation with the femoral condyles, the medial and lateral dished articular compartments separated from one another by the bearing component sagittal plane; a distal surface opposite the articular surface and parallel to the bearing component transverse plane; and a peripheral wall extending between the articular surface and the distal surface, the peripheral wall defining a tibial bearing periphery bounding the articular and distal surfaces, the peripheral wall of the tibial bearing component including an outwardly extending anterior/medial flared portion, such that the tibial bearing periphery extends beyond the baseplate periphery in the region of the anterior/medial flared portion when the tibial bearing component is fixed to the tibial baseplate, the anterior/medial flared portion of the peripheral wall comprising a convex curvature in which a smallest radius of curvature defined by the flared portion is at least 10 mm.

According to yet another embodiment thereof, the present invention provides a tibial prosthesis for articulation with femoral condyles, the tibial prosthesis defining a prosthesis coordinate system comprising: a prosthesis transverse plane extending along a medial/lateral direction and an anterior/posterior direction; a prosthesis coronal plane extending along a proximal/distal direction and the medial/lateral direction, the prosthesis coronal plane perpendicular to the prosthesis transverse plane; and a prosthesis sagittal plane extending along the anterior/posterior direction and the proximal/distal direction, the prosthesis sagittal plane perpendicular to the prosthesis transverse plane and the prosthesis coronal plane, the tibial prosthesis comprising: a tibial baseplate comprising a bone-contacting surface and an opposed tibial bearing mounting surface, the bone-contacting surface and the tibial bearing mounting surface bounded by a baseplate periphery; and a tibial bearing component fixable to the tibial baseplate, the tibial bearing component comprising: an articular surface including medial and lateral dished articular compartments sized and shaped for articulation with the femoral condyles, the medial and lateral dished articular compartments separated from one another by the prosthesis sagittal plane; a distal surface opposite the articular surface and parallel to the prosthesis transverse plane; and a peripheral wall extending between the articular surface and the distal surface, the peripheral wall defining a tibial bearing periphery bounding the articular and distal surfaces, the peripheral wall of the tibial bearing component including an outwardly extending anterior/medial flared portion, such that the tibial bearing periphery extends beyond the baseplate periphery in the region of the anterior/medial flared portion when the tibial bearing component is fixed to the tibial baseplate, the peripheral wall defining a proximal/distal thickness between the distal surface and the articular surface at the anterior/medial flared portion, the anterior/medial flared portion comprising a convex curvature occupying at least 80% of the proximal/distal thickness of the peripheral wall.

According to still another embodiment thereof, the present invention provides a high-flexion, ultra-congruent tibial prosthesis for articulation with femoral condyles, the tibial prosthesis defining a tibial prosthesis coordinate system comprising: a prosthesis transverse plane extending along a medial/lateral direction and an anterior/posterior direction, such that a proximal/distal direction is defined as a direction normal to the prosthesis transverse plane; a prosthesis coronal plane extending along the proximal/distal direction and the medial/lateral direction, the prosthesis coronal plane perpendicular to the prosthesis transverse plane; and a prosthesis sagittal plane extending along the anterior/posterior direction and the proximal/distal direction, the prosthesis sagittal plane perpendicular to the prosthesis transverse plane and the prosthesis coronal plane, the high-flexion, ultra-congruent tibial prosthesis comprising a tibial bearing component comprising: an articular surface and an opposing distal surface bounded by a peripheral wall defining a tibial bearing periphery, the articular surface including medial and lateral dished articular compartments sized and shaped for articulation with the femoral condyles through a range of flexion of at least 130 degrees, the medial and lateral dished articular compartments separated from one another by the prosthesis sagittal plane, the distal surface defining an anteroposterior slope angle of 5 degrees with the prosthesis transverse plane, the anteroposterior slope angle measured in the prosthesis sagittal plane along the anterior/posterior direction such that an anterior edge of the tibial bearing component is elevated with respect to a posterior edge thereof when the anteroposterior slope angle is greater than zero; the lateral articular compartment comprising a plurality of coronal cross-sectional profiles defining a lateral set of coronal distal-most points spanning a lateral anterior/posterior extent, the lateral set of coronal distal-most points defining a lateral articular track having a lateral sagittal distal-most point, the medial articular compartment comprising a plurality of coronal cross-sectional profiles defining a medial set of coronal distal-most points spanning a medial anterior/posterior extent, the medial set of coronal distal-most points defining a medial articular track having a medial sagittal distal-most point, a posterior eminence extending proximally from the articular surface and defining an eminence height of between 3.8 mm and 10 mm as measured from one of the medial and lateral sagittal distal-most points along the proximal/distal direction, the posterior eminence extending anteriorly from a posterior edge of the tibial bearing periphery to define an anterior/posterior eminence extent equal to less than 30% of an overall anterior/posterior extent of the tibial bearing component, the posterior eminence disposed between the medial and lateral dished articular compartments; and means for enabling flexion of at least 130 degrees with the femoral condyles; and a tibial baseplate comprising: a bone-contacting surface and an opposed tibial bearing mounting surface, the bone-contacting surface and the tibial bearing mounting surface bounded by a baseplate periphery, the tibial bearing component fixable to the tibial bearing mounting surface of the tibial baseplate to form a fixed-bearing prosthesis, the lateral articular track extrapolated posteriorly to define a posterior lateral baseplate intersection point with the baseplate periphery, and an anterior portion of the lateral articular track extrapolated anteriorly to define an anterior lateral baseplate intersection point with the baseplate periphery, a lateral anterior/posterior baseplate extent defined as the distance between the posterior lateral baseplate intersection point and the anterior lateral baseplate intersection point, the medial articular track extrapolated posteriorly to define a posterior medial baseplate intersection point with the baseplate periphery, and the medial articular track extrapolated anteriorly to define an anterior medial baseplate intersection point with the baseplate periphery, a medial anterior/posterior baseplate extent defined as the distance between the posterior medial baseplate intersection point and the anterior medial baseplate intersection point, the lateral sagittal distal-most point spaced from the anterior lateral baseplate intersection point by a distance equal to between 68% and 74% of the lateral anterior/posterior baseplate extent, and the medial sagittal distal-most point spaced from the anterior medial baseplate intersection point by a distance equal to between 59% and 63% of the medial anterior/posterior baseplate extent, whereby the high-flexion, ultra-congruent tibial prosthesis is configured to inhibit paradoxical movement while enabling high flexion.

BRIEF DESCRIPTION OF THE DRAWINGS

The above mentioned and other features and advantages of this disclosure, and the manner of attaining them, will become more apparent and the invention itself will be better understood by reference to the following description of embodiments of the invention taken in conjunction with the accompanying drawings, wherein:

FIG. 1A is a top plan view of a posterior stabilized (PS) tibial bearing component and baseplate in accordance with the present disclosure;

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

The present disclosure provides tibial bearing components for a knee prosthesis in which the bearing components have various features which enhance articular characteristics throughout a range of motion while also protecting the soft tissues of the knee after implantation.

In order to prepare the tibia and femur for receipt of a knee joint prosthesis of the present disclosure, any suitable methods or apparatuses for preparation of the knee joint may be used. Exemplary surgical procedures and associated surgical instruments are disclosed in "Zimmer LPS-Flex Fixed Bearing Knee, Surgical Technique", "NEXGEN COMPLETE KNEE SOLUTION, Surgical Technique for the CR-Flex Fixed Bearing Knee" and "Zimmer NexGen Complete Knee Solution Extramedullary/Intramedullary Tibial Resector, Surgical Technique" (collectively, the "Zimmer Surgical Techniques"), the entireties of which are hereby expressly incorporated herein by reference, copies of which are filed in an information disclosure statement on even date herewith.

As used herein, "proximal" refers to a direction generally toward the torso of a patient, and "distal" refers to the opposite direction of proximal, i.e., away from the torso of a patient. "Anterior" refers to a direction generally toward the front of a patient or knee, and "posterior" refers to the opposite direction of anterior, i.e., toward the back of the patient or knee. In the context of a prosthesis alone, such directions correspond to the orientation of the prosthesis after implantation, such that a proximal portion of the prosthesis is that portion which will ordinarily be closest to the torso of the patient, the anterior portion closest to the front of the patient's knee, etc.

Figure 3A:
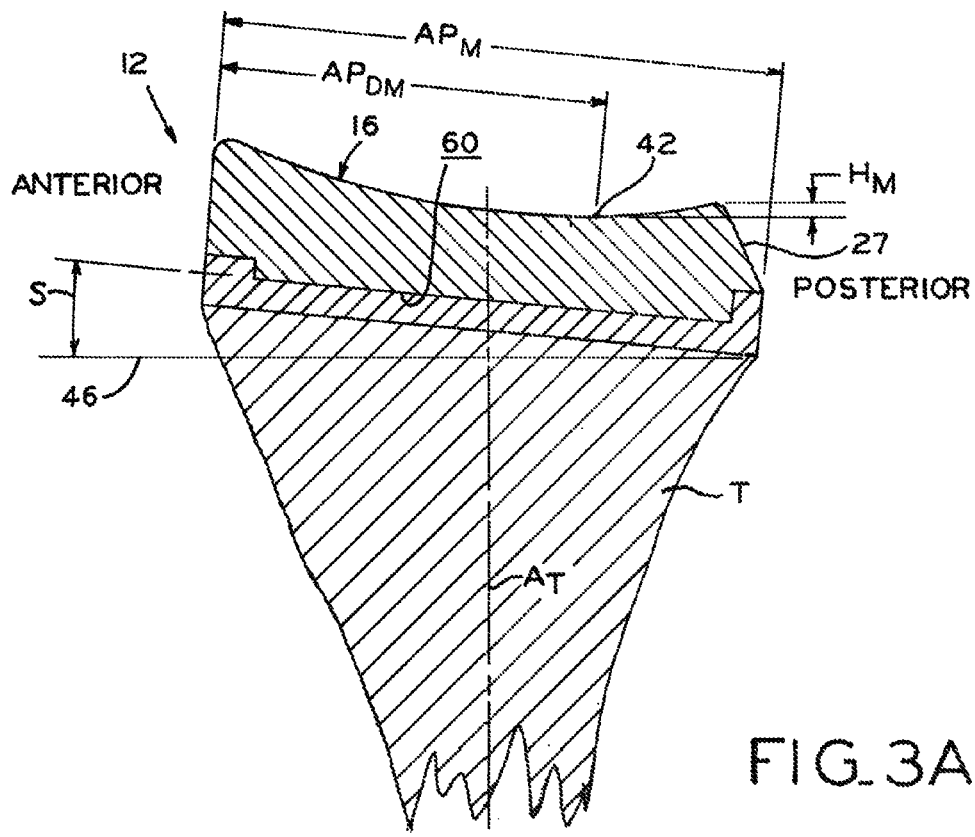
FIG. 3A is a sagittal, cross-sectional view of a tibial bearing component in accordance with the present disclosure, taken through a medial articular compartment along line 3A-3A of FIG. 1A.
Figure 3B:
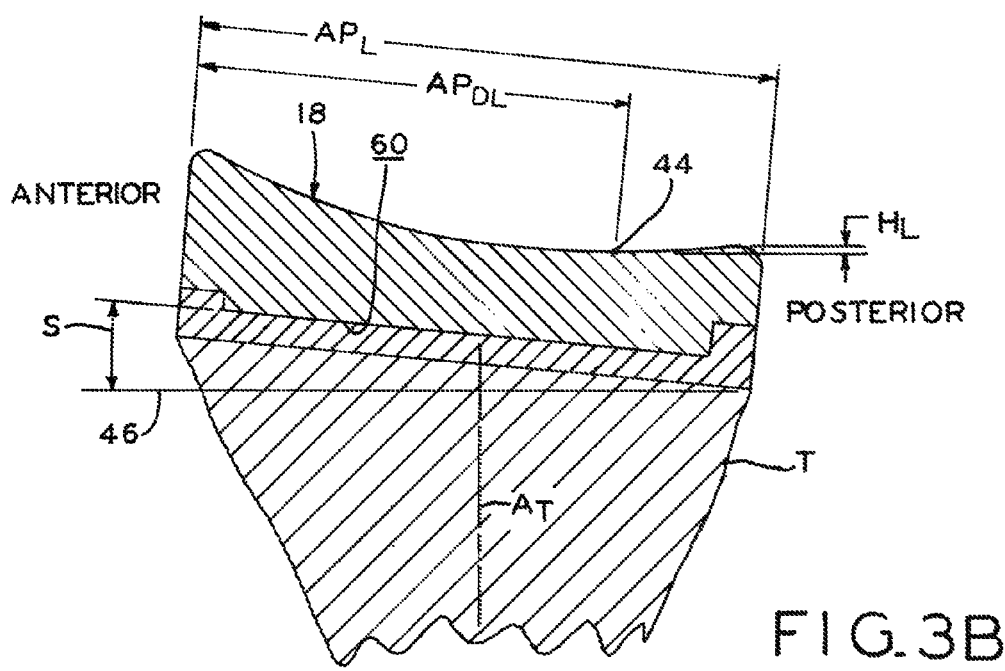
FIG. 3B is a sagittal, cross-sectional view of a tibial bearing component in accordance with the present disclosure, taken through a lateral articular compartment along line 3B-3B of FIG. 1A.

Similarly, knee prostheses in accordance with the present disclosure may be referred to in the context of a coordinate system including transverse, coronal and sagittal planes of the component. Upon implantation of the prosthesis and with a patient in a standing position, a transverse plane of the knee prosthesis is generally parallel to an anatomic transverse plane, i.e., the transverse plane of the knee prosthesis is inclusive of imaginary vectors extending along medial/lateral and anterior/posterior directions. However, in some instances the bearing component transverse plane may be slightly angled with respect to the anatomic transverse plane, such as when the proximal surface of the resected tibia T (FIGS. 3A and 3B) defines anteroposterior slope S (described in detail below). In FIGS. 3A and 3B, tibia T is shown with a positive anteroposterior slope, in that the proximal resected surface of tibia T is not normal to anatomic axis $A_T$ of tibia T. Where such anteroposterior slope S is non-zero, the bearing component transverse plane will be angled with respect to the anatomic transverse plane, with the magnitude of such angle being approximately equal to the magnitude of the anteroposterior slope S.

Coronal and sagittal planes of the knee prosthesis are also generally parallel to the coronal and sagittal anatomic planes in a similar fashion. Thus, a coronal plane of the prosthesis is inclusive of vectors extending along proximal/distal and medial/lateral directions, and a sagittal plane is inclusive of vectors extending along anterior/posterior and proximal/distal directions. As with the relationship between the anatomic and bearing component transverse planes discussed above, it is appreciated that small angles may be formed between the bearing component sagittal and coronal planes and the corresponding anatomic sagittal and coronal planes depending upon the surgical implantation method. For example, creation of anteroposterior slope S (FIGS. 3A and 3B) will angle the bearing component coronal plane with respect to the anatomic coronal plane, while alteration of the resected surface S for correction of a varus or valgus deformity will angle the bearing component sagittal plane with respect to the anatomic sagittal plane.

As with anatomic planes, the sagittal, coronal and transverse planes defined by the knee prosthesis are mutually perpendicular to one another. For purposes of the present disclosure, reference to sagittal, coronal and transverse planes is with respect to the present knee prosthesis unless otherwise specified.

The embodiments shown and described herein illustrate components for a left knee prosthesis. Right and left knee prosthesis configurations are mirror images of one another about sagittal plane. Thus, it will be appreciated that the aspects of the prosthesis described herein are equally applicable to a left or right knee configuration.

A tibial bearing component made in accordance with the present disclosure provides an articular surface with features and geometry which promote and accommodate an articular profile similar to a healthy natural knee. As described in detail below, features incorporated into the tibial bearing component articular surface advantageously provide an optimal level of constraint and motion guidance throughout a wide range of knee flexion.

Prosthesis designs in accordance with the present disclosure may include posterior stabilized (PS) prostheses and mid level constraint (MLC) prostheses, each of which includes spine 38 (FIG. 1A) and femoral cam 40 (FIG. 2) designed to cooperate with one another to stabilize femoral component 20 with respect to tibial bearing component 12 in lieu of a resected posterior cruciate ligament (PCL). For purposes of the present disclosure, PS and MLC prostheses are both of a "posterior-stabilized" design, which includes spine 38 extending proximally from the articular surface, in which the spine is spaced posteriorly from an anterior edge of the periphery of tibial bearing component 12 (FIG. 1A). Spine 38 is disposed between medial and lateral dished articular compartments 16, 18.

Figure 4A:
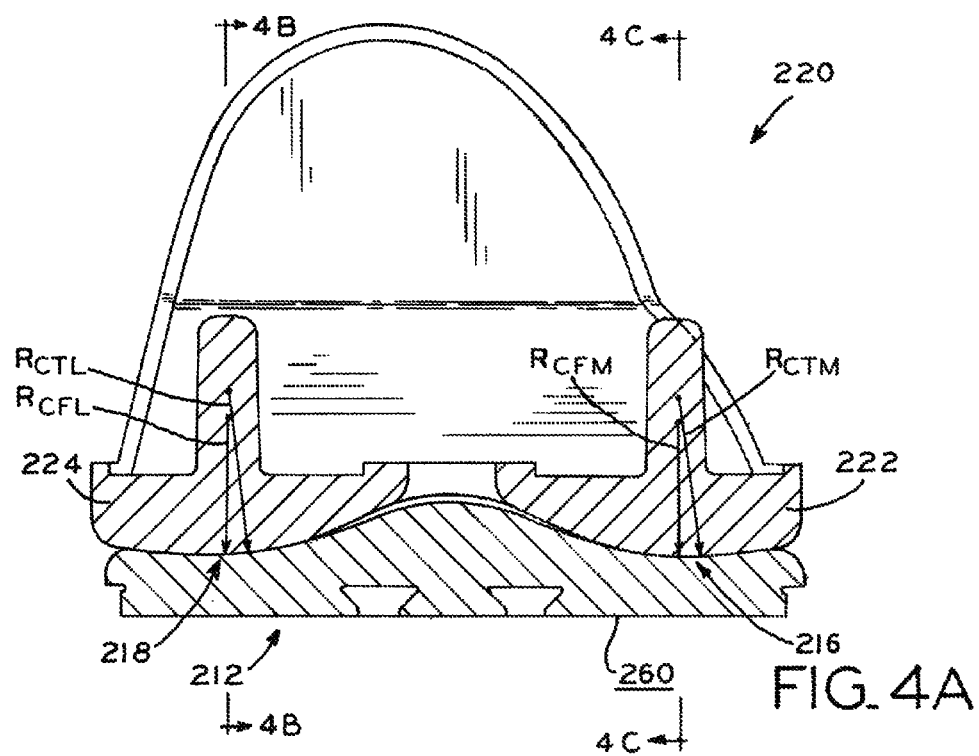
FIG. 4A is an elevation, cross-sectional view of the tibial bearing shown in FIG. 1A, together with a femoral component made in accordance with the present disclosure, taken in a coronal plane.
Figure 4B:
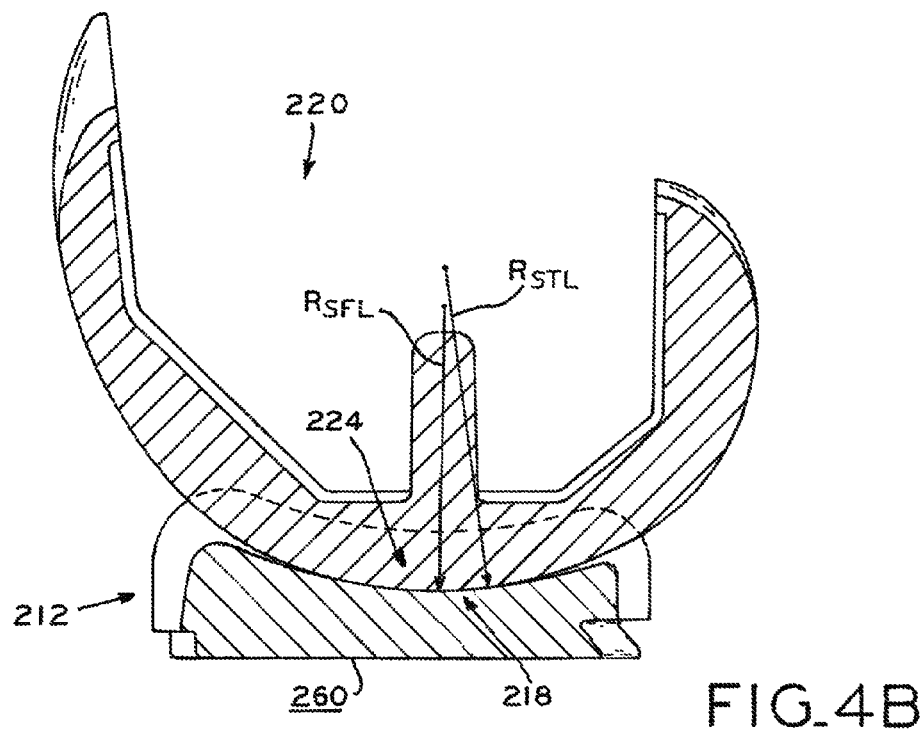
FIG. 4B is an elevation, cross-sectional view of the tibial bearing and femoral components shown in FIG. 4A, taken in a sagittal plane through the lateral articular condyle and articular compartment thereof.
Figure 7A:
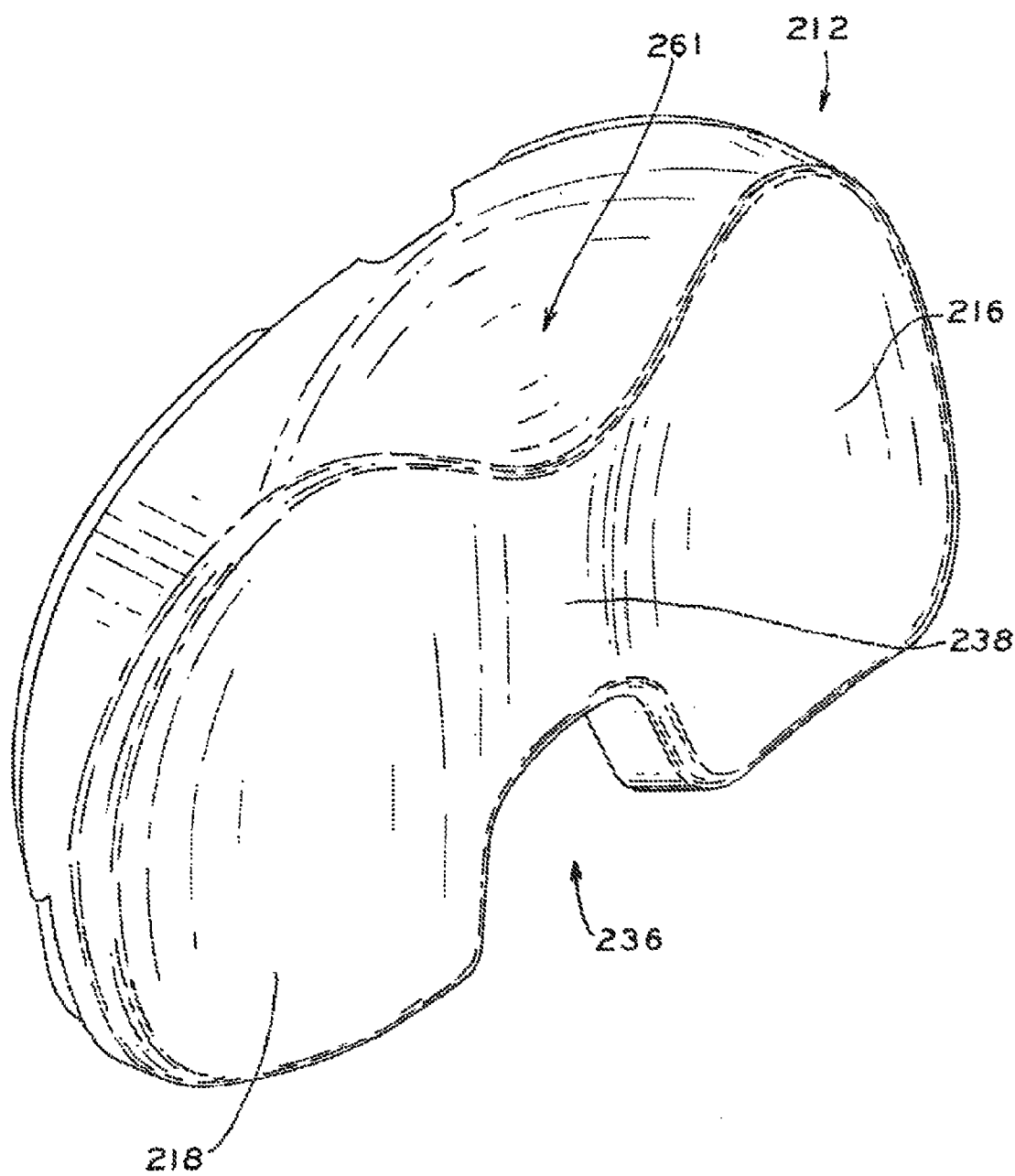
FIG. 7A is a top, perspective view of a cruciate-retaining (CR) tibial bearing component made in accordance with the present disclosure.
Figure 7B:
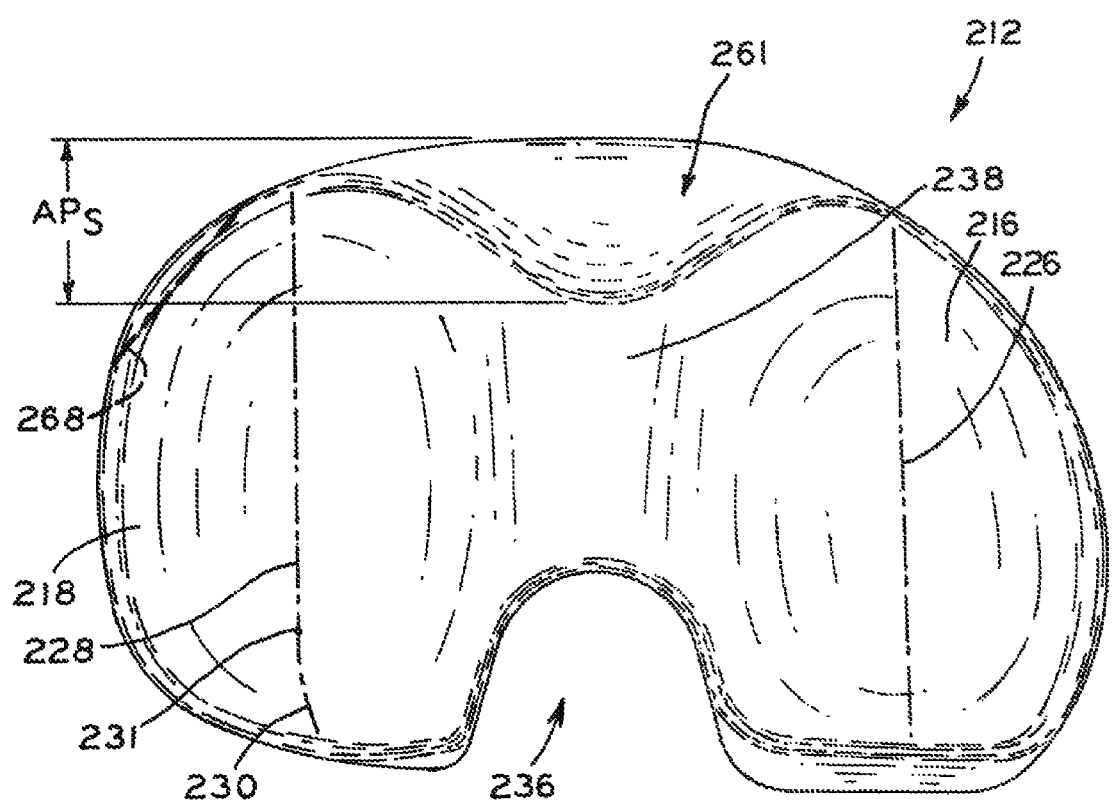
FIG. 7B is a top plan view of the tibial bearing component shown in FIG. 7A.

Another contemplated design includes "cruciate retaining" (CR) prostheses, such as those using components configured as shown in FIGS. 4A and 4B. CR designs omit spine 38 and femoral cam 40, such that femoral component 220 defines an intercondylar space between medial and lateral condyles 222, 224 that is entirely open and uninterrupted by femoral cam 40. CR tibial components are generally used in surgical procedures which retain the PCL. Cruciate-retaining (CR) type tibial bearing component 212 is illustrated in FIGS. 7A and 7B. Tibial bearing component 212 and femoral component 220 are substantially similar to tibial bearing component 12 and femoral component 20 described herein respectively, with reference numerals of components 212, 220 analogous to the reference numerals used in component 12, 20 except with 200 added thereto. Structures of tibial bearing component 212 and femoral component 220 correspond to similar structures denoted by corresponding reference numerals of tibial bearing component 12 and femoral component 20, except as otherwise noted.

Referring to FIG. 7A, posterior cutout 236 is sized and positioned to accommodate a posterior cruciate ligament upon implantation of tibial bearing component 212. Intercompartmental eminence 238 comprises an intercondylar ridge disposed between medial and lateral articular compartments 216, 218 and extending anteroposteriorly from posterior 236 cutout to anterior relief space 261. Thus, the intercondylar ridge defined by intercompartmental eminence 238 is disposed between the medial and lateral dished articular compartments and occupies the available anterior/posterior space therebetween.

Anterior relief space 261 is also disposed generally between medial and lateral articular compartments 216, 218, anterior of intercondylar eminence 238, and extending posteriorly from an anterior edge of the periphery of tibial bearing component 212. An exemplary embodiment of relief space 261 is described in U.S. Provisional Patent Application Ser. No. 61/621,361, entitled TIBIAL BEARING COMPONENT FOR A KNEE PROSTHESIS WITH IMPROVED ARTICULAR CHARACTERISTICS and filed on Apr. 6, 2012, and is U.S. patent application Ser. No. 13/459,037, entitled TIBIAL BEARING COMPONENT FOR A KNEE PROSTHESIS WITH IMPROVED ARTICULAR CHARACTERISTICS and filed on Apr. 27, 2012, now issued as U.S. Pat. No. 8,858,643, the entire disclosure of which is hereby expressly incorporated herein by reference.

Figure 6A:
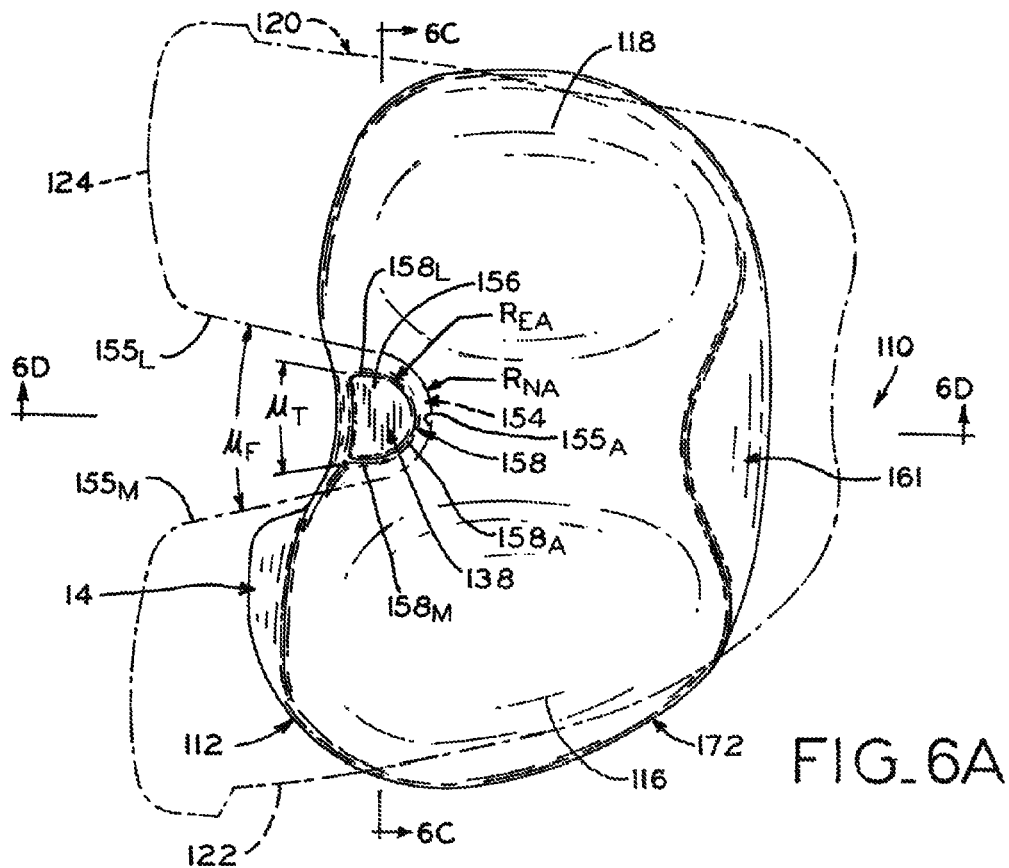
FIG. 6A is a top plan view of an ultracongruent (UC) tibial bearing component made in accordance with the present disclosure.
Figure 6B:
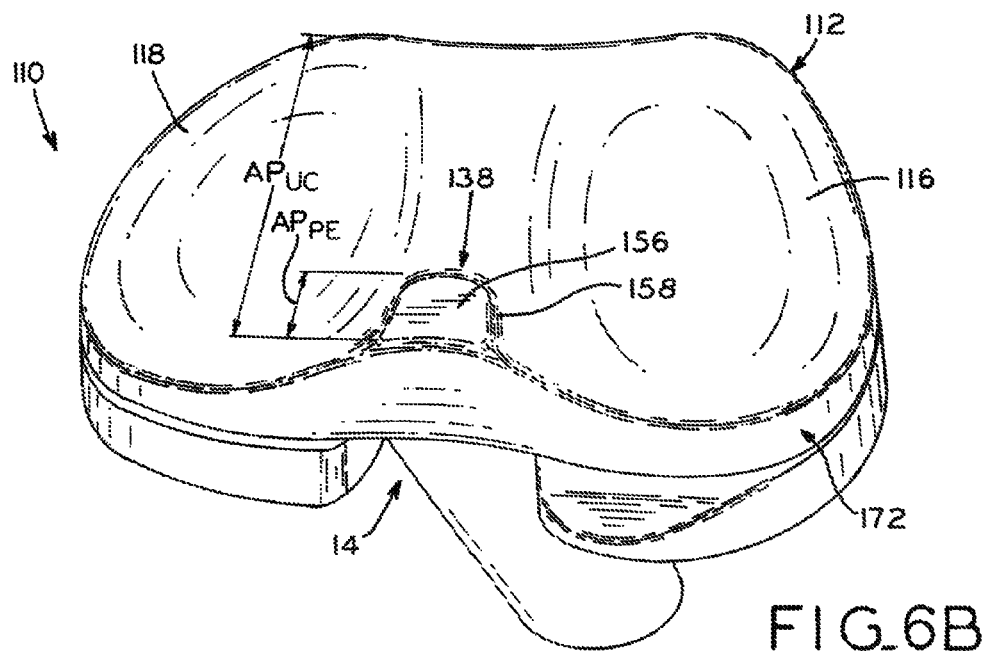
FIG. 6B is a perspective view of the tibial bearing component shown in FIG. 6A, shown positioned atop a tibial baseplate.

Yet another design includes "ultra congruent" (UC) prostheses, shown in FIGS. 6A, 6B, 8A and 8B, which also omits spine 38 and femoral cam 40 but is designed for use with a patient whose PCL is resected. Referring to FIGS. 6A and 6B, for example, ultra-congruent tibial bearing component 112 is illustrated which includes posterior eminence 138. Posterior eminence 138 extends proximally from the articular surface of tibial bearing component 112, by a distance more than intercondylar eminence 238 and less than spine 38. Posterior eminence 138 also extends anteriorly from a posterior edge of the tibial bearing periphery, in the area normally occupied by posterior cutout 36 (FIG. 1A). Thus, posterior eminence 138 is distinguished from spine 38 in that posterior eminence 138 resides at the posterior edge of tibial bearing component 112, and in that it defines an intermediate height above the surrounding articular surface. Like spine 38 and intercompartmental eminence 238, posterior eminence 138 is disposed between the medial and lateral dished articular compartments 116, 118.

"Congruence," in the context of knee prostheses, refers to the similarity of curvature between the convex femoral condyles and the correspondingly concave tibial articular compartments. A detailed discussion of congruence appears below. UC designs utilize very high congruence between the tibial hearing compartments and femoral condyles to provide prosthesis stability, particularly with respect to anterior/posterior relative motion.

Figure 11:
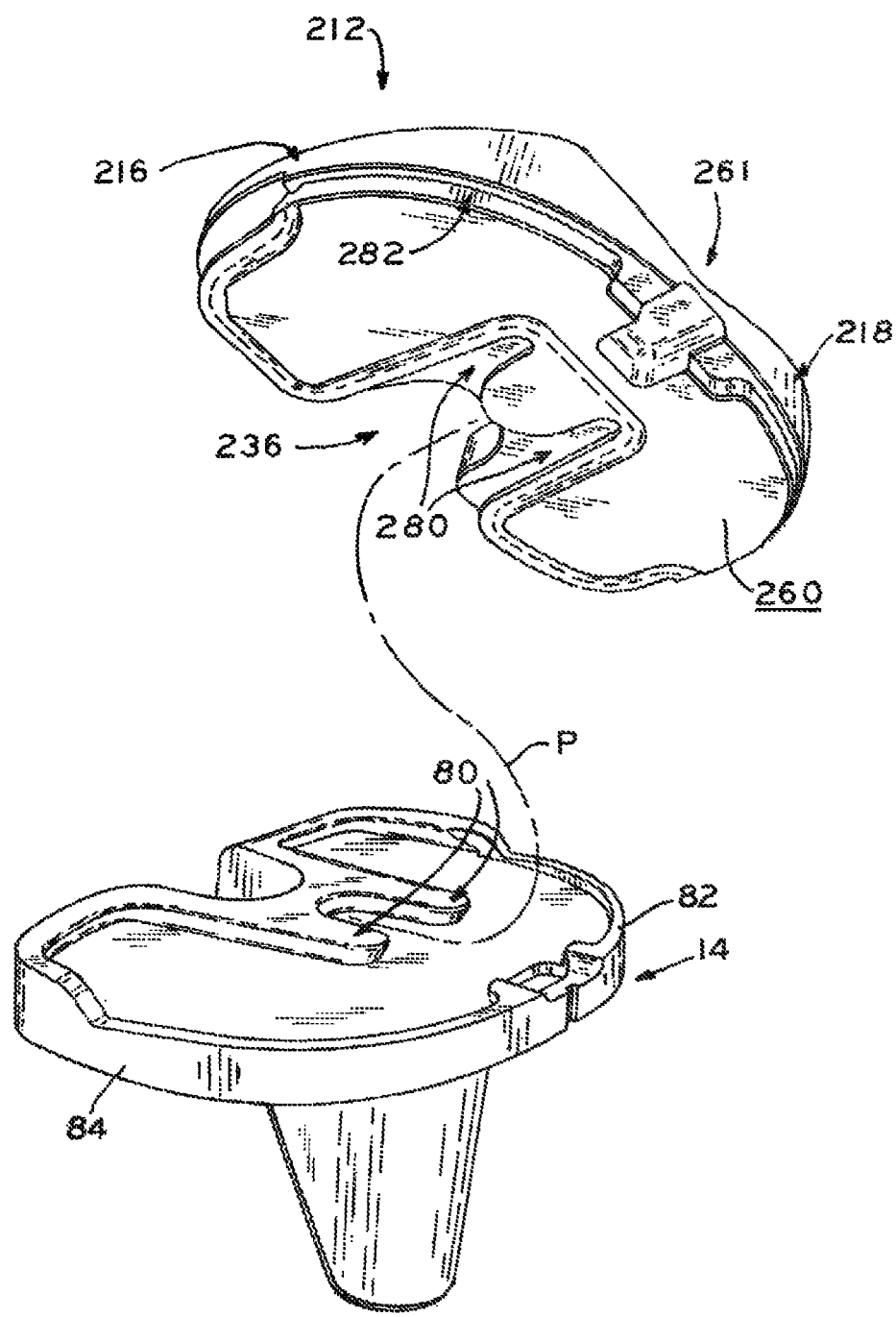
FIG. 11 is a perspective, exploded view illustrating assembly of a tibial bearing component and tibial baseplate made in accordance with the present disclosure.

In the exemplary embodiments described below, tibial bearing components 12, 112, 212 are each adapted to fixedly attach to tibial baseplate 14, such that the resulting tibial prosthesis is a "fixed-bearing" design. For purposes of illustration, tibial bearing component 212 is shown in FIG. 11. As shown in FIG. 11, distal surface 260 of tibial bearing component 212 includes a two-pronged recess 280 which cooperates with a correspondingly shaped two-prong boss 80 protruding proximally from tray 84 of tibial baseplate 14. Further, a peripheral undercut 282 formed around the periphery of distal surface 260 of tibial bearing component 212 is sized and shaped to receive peripheral wall 82. Upon assembly, tibial bearing component 212 is advanced along path P, such that tibial bearing component moves along a generally anterior-to-posterior path as recess 280 begins to engage with boss 80. Further posterior movement of tibial bearing component 212 causes a tight interfitting engagement between recess 280 and boss 80, and eventually aligns peripheral undercut 282 with peripheral wall 82. When so aligned, tibial bearing component 212 "snaps" into fixed engagement with tibial baseplate 14. Posterior-stabilized tibial bearing component 12 and ultra-congruent tibial bearing component 112 may fixedly engage with tibial baseplate in a similar fashion.

Once such fixed engagement takes place, tibial bearing component 212 (or components 12 or 112) is immovable with respect to tibial baseplate 14. As used herein, a "fixed bearing" tibial prosthesis is a prosthesis in which a bearing component is seated atop a tibial baseplate in a final, locked position such as the arrangement described above. In this locked position, lift-off of bearing components 12, 112, 212 from tibial baseplate 14, as well as transverse movement of bearing components 12, 112, 212 relative to tibial baseplate 14, is prevented during natural articulation of the knee. While some very small amount of motion (sometimes referred to as micromotion) may occur between tibial bearing components 12, 112, 212 and tibial baseplate 14 in a fixed bearing prosthesis, no such motion occurs by design along a designated path.

Exemplary fixed-bearing securement designs are described in U.S. Patent Application Publication No. 2012/0035737, filed Jul. 22, 2011 and entitled TIBIAL PROSTHESIS, and in U.S. Patent Application No. 2012/0035735, filed Jul. 22, 2011 and entitled TIBIAL PROSTHESIS, the entire disclosures of which are hereby expressly incorporated herein by reference. Other types of fixed bearing prostheses include "monoblock" type designs, in which the tibial bearing component is permanently molded over the tibial baseplate to create a unitary tibial prosthesis. However, it is also contemplated that the features of a tibial bearing component described herein may be used on a "mobile bearing" prosthesis design in which the tibial bearing component is allowed to move relative to the tibial baseplate during articulation.

Except as otherwise specified herein, all features described below may be used with any potential prosthesis design. While a particular design may potentially include all the features described herein, it is contemplated that some prosthesis designs may include selected features described herein but omit other such features, as required or desired for a particular application.

Figure 1B:
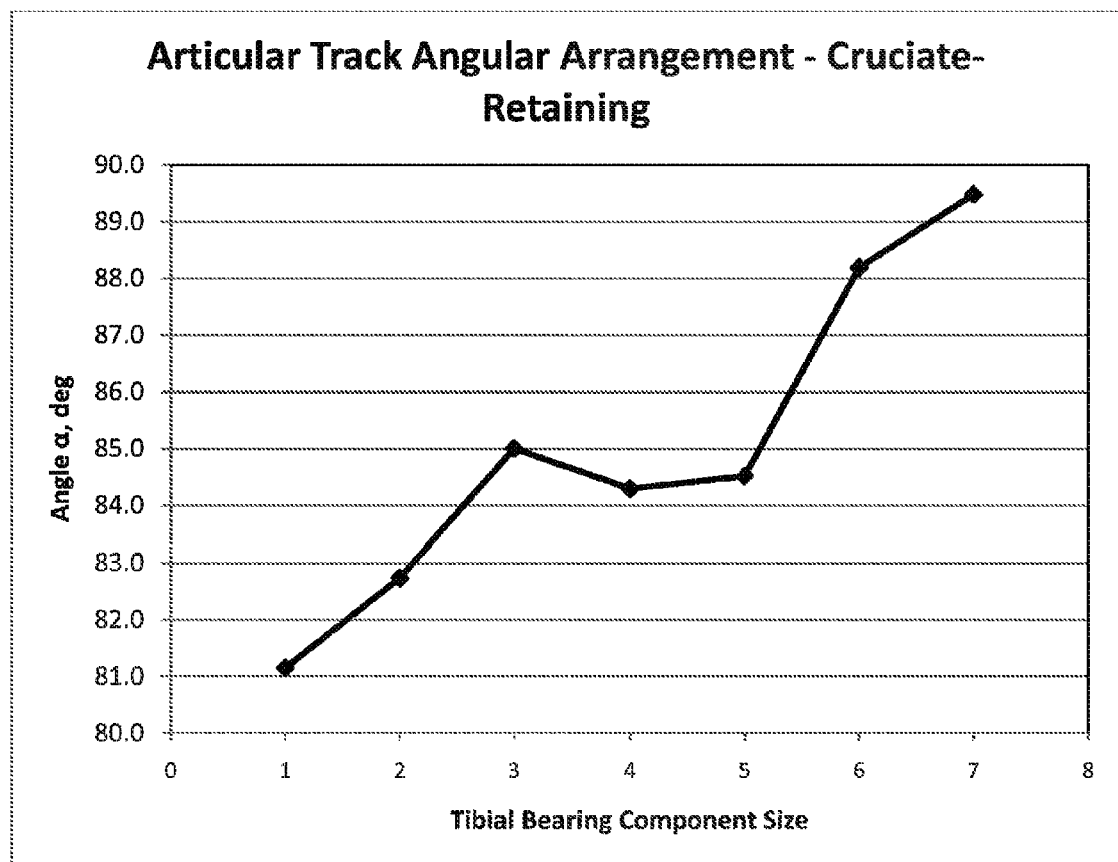
FIG. 1B is a graph plotting the angular arrangement of articular tracks of various sizes of ultra-congruent tibial bearing components in accordance with the present disclosure.
Figure 2:
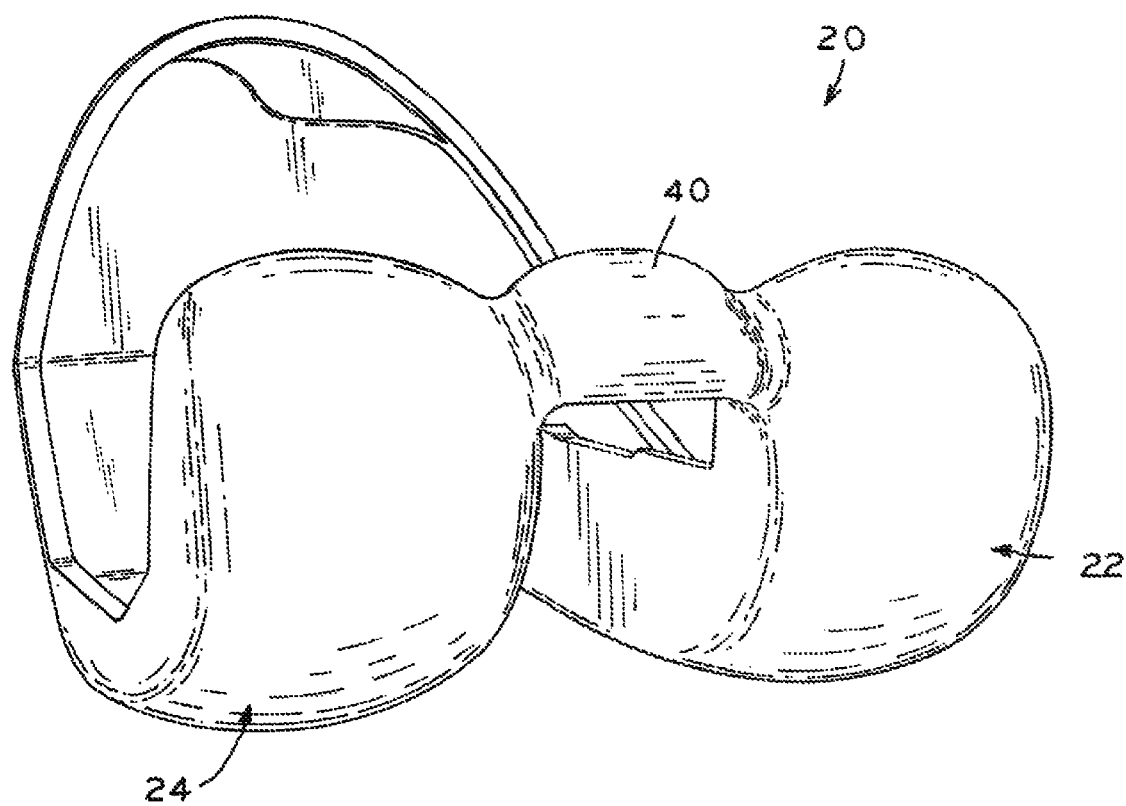
FIG. 2 is a perspective view of a femoral component in accordance with the present disclosure.

1. Articular Tracks: Arcuate Posterior/Lateral Bearing Path for Deep Flexion Rollback FIG. 1A illustrates tibial prosthesis 10 having tibial bearing component 12 and tibial baseplate 14. The perspective of FIG. 1A is a transverse-plane view of tibial prosthesis 10, looking down upon the proximally facing articular surface of bearing component 12, such that distal surface 60 (FIG. 3A) is substantially parallel to the transverse plane. Bearing component 12 includes medial articular compartment 16 and lateral articular compartment 18, each defining concave dished articular surfaces sized and shaped to articulate with femoral condyles, e.g., prosthetic condyles such as medial and lateral condyles 22, 24 of femoral component 20 (FIG. 2). For purposes of the present disclosure, a central sagittal plane may be said to bisect tibial prosthesis 10 into a medial portion including medial articular compartment 16 and a lateral portion including lateral compartment 18.

During articulation from knee extension to flexion, the contact point between condyles 22, 24 and articular compartments 16, 18 moves posteriorly, thereby defining medial articular track 26 and lateral articular track 28, respectively. Articular tracks 26, 28 are also representative of the lowest points along the anterior/posterior extent of medial and lateral articular compartments 16, 18. More particularly, any given coronal cross-section of articular compartments 16, 18 (such as, for example, the corona cross-section shown in FIG. 4A) defines medial and lateral distal-most points in medial and lateral articular compartments 16, 18, respectively. These distal-most points are each coincident with medial and lateral articular tracks 26, 28, respectively. When the distal-most points of all possible coronal cross-sections (i.e., every coronal cross-section across the entire anterior/posterior extent of medial and lateral articular compartments 16, 18) are aggregated, the set of distal-most points form lines which define medial and lateral articular tracks 26, 28 respectively. As described in detail below, the location of distal-most points 42, 44 of articular compartments 16, 18 may be determined accounting for or ignoring the antero-posterior tibial slope S (FIGS. 3A and 3B), it being understood that the magnitude of slope S influences the anterior/posterior positions of distal-most points 42, 44. It is contemplated that either method of determining the locations of distal-most points 42, 44 may be appropriate in some instances, while in other instances a particular method is appropriate. For purposes of the present disclosure, both methods of determining the anterior/posterior positions of distal-most points 42, 44 may be used except where otherwise specified.

For convenience, the present discussion refers to "points" or "lines" of contact between tibial bearing component 12 and femoral component 20 along articular tracks 26, 28. However, it is of course appreciated that each potential point or line of contact (i.e., any of the points along one of articular tracks 26, 28) is not truly a point or line, but rather an area of contact. These areas of contact may be relatively larger or smaller depending on various factors, such as prosthesis materials, the amount of pressure applied at the interface between tibial bearing component 12 and femoral component 20, and the like. Moreover, it is appreciated that some of the factors affecting the size of the contact area may change dynamically during prosthesis use, such as the amount of applied pressure at the femoral/tibial interface during walking, climbing stairs or crouching, for example. For purposes of the present discussion, a "contact point" may be taken as the point at the geometric center of the area of contact. The "geometric center", in turn, refers to the intersection of all straight lines that divide a given area into two parts of equal moment about each respective line. Stated another way, a geometric center may be said to be the "average" (i.e., arithmetic mean) of all points of the given area. Similarly, a "contact line" is the central line of contact passing through and bisecting an elongate area of contact.

Referring still to FIG. 1A, medial articular track 26 defines a generally straight line extending along an anterior/posterior direction when viewed from above (i.e., when projected onto the transverse plane) as shown in FIG. 1A. Thus, as medial condyle 22 of femoral component 20 articulates with medial compartment 16 of tibial bearing component 12, the point of contact therebetween follows a generally straight anterior/posterior path as projected onto the transverse plane. For purposes of the present disclosure, a "straight" line or path defined by a component of a knee prosthesis refers to a nominally straight line or path, it being appreciated that manufacturing tolerances and circumstances of in vivo use may cause such straight lines or paths to deviate slightly from the nominal path. As used herein, a "nominal" quantity or feature refers to a feature as designed, notwithstanding variabilities arising from manufacturing and/or use.

On the other hand, lateral articular track 28 includes arcuate portion 30 near the posterior edge of lateral articular compartment 18. The contact point between lateral condyle 24 and lateral articular compartment 18 follows a generally straight-line anteroposterior path throughout early and mid flexion, such that an anterior portion of lateral articular track 28 is linear in a similar fashion to medial articular track 26. However, when prosthesis 10 reaches a deep flexion configuration and the contact point between lateral condyle 24 and lateral articular compartment 18 advances toward the posterior portion of lateral compartment 18, the corresponding posterior portion of articular track 28 curves or arcs inwardly to define a curved line forming arcuate portion 30.

In the exemplary embodiment of FIG. 1A, arcuate portion 30 of articular track 28 defines an arc having a radius $R_T$ defining radius center $C_T$, which is spaced medially from lateral articular track 28. In the illustrative embodiment of FIG. 1A, this medial spacing is equal to the medial/lateral separation distance $D_T$ (FIG. 1A) between the parallel linear portions of medial and lateral articular tracks 26, 28, such that radius center $C_T$ of radius $R_T$ is coincident with medial articular track 26. Radius $R_T$ may be between as little as 30 mm, 34 mm or 36 mm and as large as 48 mm, 52 mm or 60 mm, or may be any size within any range defined by any of the foregoing values. The magnitude of Radius $R_T$ generally grows larger as the size of tibial bearing component 12 increases across a range of prosthesis sizes.

In addition to the coronal distal-most points described above, each of medial and lateral articular tracks 26, 28 include an arcuate sagittal profile (shown in FIGS. 3A and 3B and described below) defining sagittal distal-most points 42, 44 respectively. Referring to FIG. 1A, the anterior/posterior position of radius center $C_T$ is, in an exemplary embodiment, coincident with distal-most point 42 thereof as viewed in the transverse plane perspective of FIG. 1A. Further discussion of distal-most point 42 appears below within the context of an implanted knee prosthesis. For purposes of the illustration of FIG. 1A, however, distal-most point 42 may be taken to be the point in lateral compartment 18 which is closest to distal surface 60 of tibial bearing component 12 (see FIG. 4B).

In addition, arcuate portion 30 defines a point of tangency with the anterior remainder of articular track 28 at transition point 31, such that transition point 31 represents the posterior terminus of such linear anterior portion and the anterior terminus of arcuate portion 30 of articular track 28. In the exemplary embodiment of FIG. 1A, radius center $C_T$ and transition point 31 of lateral articular track 28 lie in a common coronal plane. Stated another way, the linear/arcuate transition point 31 of lateral articular track 28 and radius center $C_T$ of medial articular track 26 share a common anteroposterior location along their respective articular tracks 26, 28.

Advantageously, setting the magnitude of radius equal to bearing spacing distance $D_T$ accommodates external rotation of the femur, which causes femoral component 20 (FIG. 2) to pivot in deep flexion about the contact point between medial condyle 22 and medial articular compartment 16. This contact point is coincident with radius center $C_T$, such that lateral condyle 24 follows the path of least resistance upon lateral articular compartment 18 even as external rotation and the associated femoral rollback occurs.

In an exemplary embodiment, arcuate portion 30 of lateral articular track 28 occupies as little as 20% or 25% and as much as 28%, 35% or 50% of the overall anterior/posterior extent of lateral articular compartment 18, or may occupy any percentage within any range defined by any of the foregoing values. This anterior/posterior location of transition point 31 cooperates with the articular surface geometry of lateral articular compartment 18 and the articular surface geometry of lateral condyle 24 of femoral component 20 to set the initial level of flexion for engagement of condyle 24 with arcuate portion 30 of articular track 28 at approximately 90 degrees of flexion, though it is appreciated that the actual initial engagement may vary substantially depending on, for example, unique patient anatomy and the particular conditions of articulation during prosthesis use.

As noted above, it is contemplated that articular tracks 26, 28 as described herein may be incorporated into ultra-congruent, posterior-stabilized and cruciate-retaining designs, and that the benefits and advantages conferred by the disclosed arrangement of articular tracks 26, 28 may be realized in any knee prosthesis design.

2. Articular Tracks: Rotational Orientation with Respect to Posterior Edge of the Tibial Prosthesis.

Articular tracks 26, 28 are angled with respect to the posterior edges of tibial bearing component 12 and tibial baseplate 14, which promotes a similarly angled orientation of articular track 26, 28 upon implantation to facilitate enhanced prosthesis articulation. Such angling may be defined in the context of tibial bearing component 12 alone, as described below, and/or when tibial bearing component 12 is attached to tibial baseplate 14.

Referring still to FIG. 1A, tibial bearing component 12 defines an acute angle α between posterior line 32 (described in detail below) and medial articular track 26. Because medial articular track 26 and the linear anterior portion of lateral articular track 28 are parallel to one another (as noted above), angle α is also defined between the linear anterior portion of lateral articular track 28 and posterior line 32.

Similarly, angle θ is defined between posterior line 34 of tibial baseplate 14 and articular tracks 26, 28. As described in detail below, the medial compartment of tibial baseplate 14 extends further posteriorly compared to the posterior/medial edge of tibial bearing component 12, but tibial bearing component 12 and tibial baseplate 14 define similar anteroposterior extents in their respective lateral sides. Therefore, as shown in FIG. 1A, angle θ is less than angle α.

To form posterior lines 32, 34 as shown in FIG. 1A, medial articular track 26 and the linear anterior portion of lateral articular track 28 are first extrapolated posteriorly to intersect with the outer peripheries defined by tibial bearing component 12 and tibial baseplate 14, respectively. Posterior line 32 of tibial bearing component 12 is then defined as the line which joins medial and lateral intersection points $P_{TM}$, $P_{TL}$ between medial and lateral articular tracks 26, 28 and the periphery of tibial bearing component 12. Posterior line 34 of tibial baseplate 14 is the line which joins intersection points $P_{BM}$, $P_{HL}$ between medial and lateral articular tracks 26, 28 and the periphery of tibial baseplate 14.

In an exemplary embodiment, angle α defined by tibial bearing component 12 alone may be only slightly less than 90 degrees, such as by 0.5 degrees. In other embodiments and across various prosthesis sizes, angle α may be less than 90 degrees by as much as 9 degrees or more. For example, referring to FIG. 1B, angle α for various sizes of cruciate-retaining prosthesis designs are illustrated, with sizes 1 and 7 (on the horizontal axis) being the smallest and largest component sizes, respectively, and the intermediate sizes 2-6 growing progressively in size. For such cruciate-retaining designs, angle α ranges from 81 degrees to 89.5 degrees across the seven cruciate-retaining component sizes.

Figure 1C:
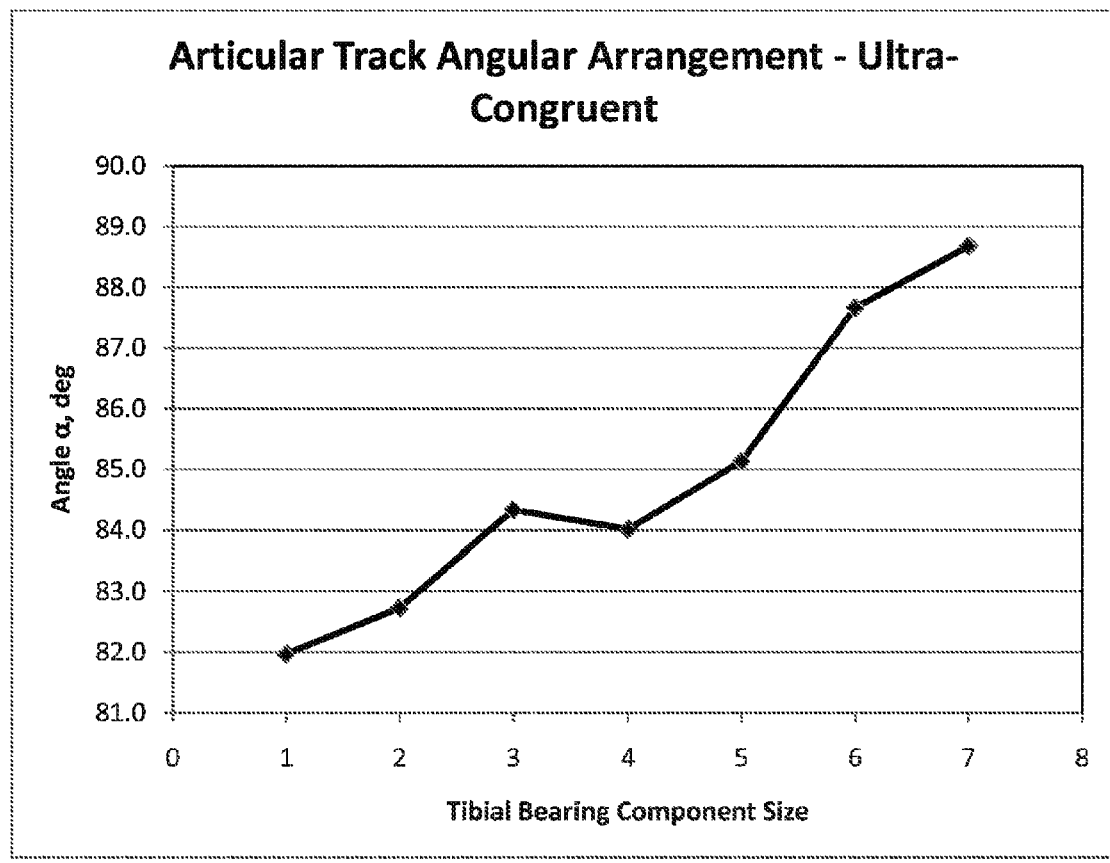
FIG. 1C is a graph plotting the angular arrangement of articular tracks of various sizes of posterior-stabilized tibial bearing components in accordance with the present disclosure.

Referring to FIG. 1C angle α for seven sizes again shown on the horizontal axis) is illustrated for an ultra-congruent prosthesis design. Angle α, as shown on the vertical axis, ranges from 82 degrees to 88.7 degrees across the seven ultra-congruent component sizes.

Figure 1D:
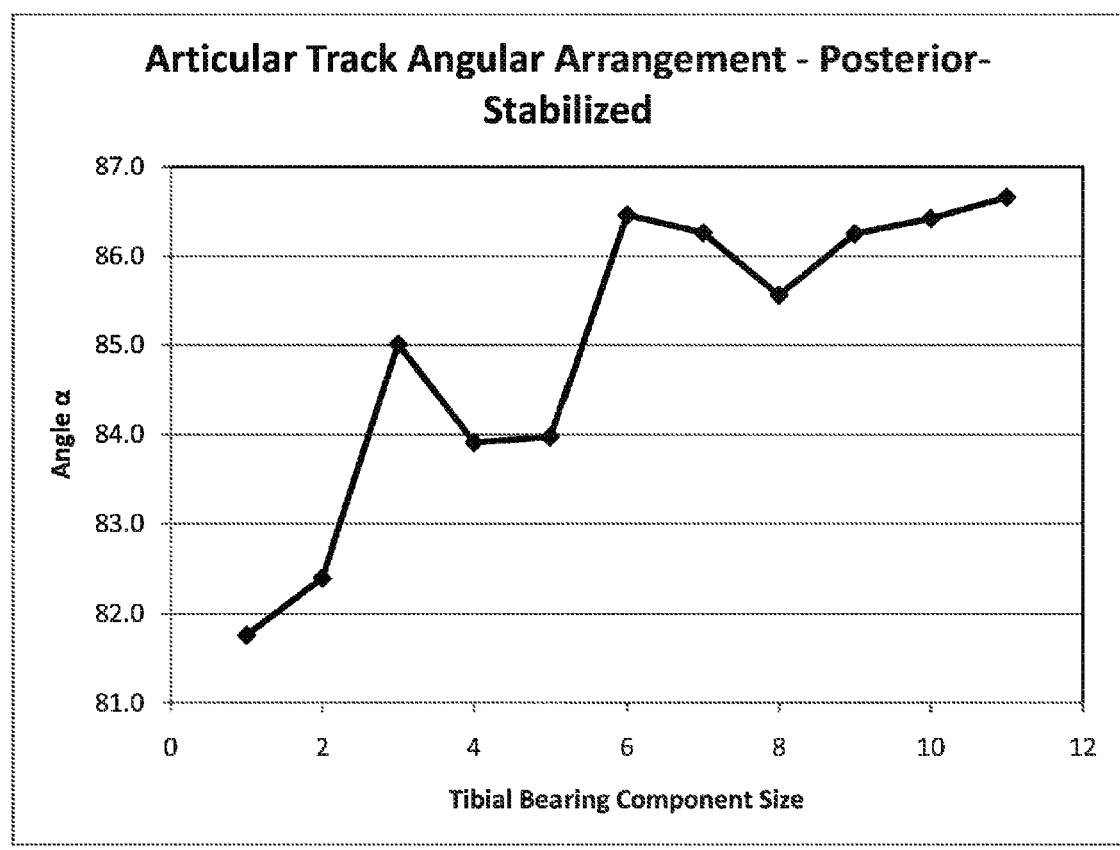
FIG. 1D is a graph plotting the angular arrangement of articular tracks of various sizes of cruciate retaining tibial bearing components in accordance with the present disclosure.

Referring to FIG. 1D, angle α for eleven sizes of posterior-stabilized prosthesis designs are illustrated, with sizes 1 and 11 (on the horizontal axis) being the smallest and largest component sizes, respectively, and the intermediate sizes 2-10 growing progressively in size. Angle α, again on the vertical axis, ranges from 81.7 degrees to 86.7 degrees across the eleven posterior-stabilized component sizes.

FIGS. 1B-1D all illustrate a family of tibial bearing components within a given design class (i.e., posterior-stabilized, ultra-congruent or cruciate-retaining), in which each family exhibits an upward trend in angle α as the prosthesis size grows larger. Generally speaking, angle α experiences a minimum value for the smallest component size and a largest value for the largest component size, with angle α in intermediate component sizes following an upward trend from smallest-to-largest. In some instances, the next-largest size will define a decreased angle α as compared to the next-smallest size, as illustrated in FIGS. 1B-1D. However, a substantial majority of sizes experience an increase in angle α from smaller to larger sizes, as well as the overall substantial increase exhibited by the overall change from the smallest to largest size. Therefore, it may be said that the trend in angle α is generally upward across the range of sizes.

Angle θ is less than angle α, and deviates from angle α by any amount greater than 0 degrees. In an exemplary embodiment, angle θ is less than angle α by as little as 0.01 degrees, 0.4 degrees or 1 degree and as large as 6 degrees, 8.8 degrees or 15 degrees, or may be any value within any range defined by any of the foregoing values. The difference between angle θ and angle α generally smaller for small prosthesis sizes and larger for large prosthesis sizes.

Advantageously, the rotation of articular tracks 26, 28 with respect to posterior lines 32, 34 rotates or "clocks" tibial bearing component 12 into a counterclockwise orientation, as viewed from above, as compared to a non-rotated or centered orientation (in which angles α and/or θ would be 90-degrees). Stated another way, such "clocking" can be thought of as rotation of the proximal, articular surface of a tibial bearing component while leaving the distal, baseplate-contacting surface non-rotated. Clocking in accordance with the present disclosure is therefore analogous to disconnecting articular compartments 16, 18 from distal surface 60, rotating articular compartments 16, 18 in a counterclockwise direction (as viewed from above), and reconnecting articular compartments 16, 18 to distal surface 60 in the new, rotated orientation. In this regard, the structure and arrangement of tibial bearing component 12 provides means for clocking articular tracks 26, 28.

Such clocking yields an improved articular profile which more closely mimics natural motion of the knee, reduces wear of the prosthesis components, and enhances prosthesis longevity. More particularly, tibial bearing component 12 promotes clinically successful prosthesis function by providing a correct orientation and position of the tibiofemoral "bearing couple" with respect to one another. The bearing couple is comprised of femoral component 20 and tibial bearing component 12. In prosthesis 10, articular compartments 16, 18 are fixed to tibial baseplate 14 and therefore the tibial component defines the articular surface orientation with respect to tibia T (see, e.g., FIG. 3A). Femoral component 20, which is mounted to the distal end of the femur F, is not mechanically coupled to tibial bearing component 12, but instead articulates therewith along an articular profile influenced by the mating articular surfaces of tibial bearing component 12 and femoral component 20. Thus, the placement and articular geometry of tibial bearing component 12 helps establish the lower (distal) half of the bearing couple.

The clocking of tibial articular tracks 26, 28, in cooperation with the asymmetric periphery of tibial baseplate 14, discourages implantation of tibial bearing component 12 such that tracks 26, 28 are relatively internally rotated. By preventing such internal rotation of tracks 26, 28, tibial bearing component 12 provides smooth cooperation with the knee's soft tissues during in vivo knee articulation by ensuring that the articular bearing motion is properly oriented relative to the femur to deliver desired knee kinematics, range of motion (ROM) and stability. Advantageously, this cooperation promotes decreased material wear in tibial bearing component 12, enhanced prosthesis stability, proper knee balance, and high ROM.

Further, the substantial coverage provided by tibial baseplate 14 and the clocked orientation of articular tracks 26, 28 with respect thereto encourages proper rotation of tibial bearing component 12 upon implantation. When a bone-contacting surface of a properly sized tibial baseplate 14 is mated with a resected tibia, the asymmetric periphery thereof results in substantial coverage of the resected proximal surface and largely controls the rotational orientation thereof. A detailed description of the periphery of tibial baseplate 14 and the attendant substantial coverage of a resected proximal tibia is described in U.S. Patent Application Publication No. 2012/0022659 filed Jul. 22, 2011 and entitled "ASYMMETRIC TIBIAL COMPONENTS FOR A KNEE PROSTHESIS", the entire disclosure of which is hereby expressly incorporated by reference herein. With tibial baseplate 14 properly oriented, fixing tibial bearing component 12 thereto will set the location and orientation of bearing component 12, which will then be automatically "clocked" in the advantageous manner described above.

The amount of rotation or "clocking" of articular tracks 26, 28 may vary depending on prosthesis design and/or prosthesis size (as described above). For any given prosthesis design in a particular style and for a particular sized tibia, it is contemplated that a second tibial bearing component 12 may be provided which defines a different magnitude of clocking but is otherwise identical to the first tibial bearing component 12. Thus, two tibial bearing components 12 useable with a common tibial baseplate 14 and femoral component 20—but each with different levels of clocking—may be provided and chosen by a surgeon preoperatively or intraoperatively. Similarly, a net of three or more tibial bearing components 12 may be provided, each sharing a common size and prosthesis design, but all having different levels of clocking.

3. Articular Tracks: Anterior Shift of Bearing Compartment Distal-Most Points.

Referring now to FIGS. 3A and 3B, medial and lateral articular compartments 16, 18 define distal-most points 42, 44, respectively. Distal-most points 42, 44 are coincident with medial and lateral articular tracks 26, 28, respectively, and represent the distal-most points from a sagittal perspective on articular tracks 26, 28 when tibial bearing component 12 is implanted upon tibia T with an anteroposterior slope S of 5 degrees. Tibial baseplate 14, having a constant thickness across its anterior/posterior extent, does not affect the value of anteroposterior slope S. Anteroposterior slope S references a zero degree slope line 46, which is defined by a generally transverse reference plane normal to anatomic axis $A_T$ of tibia T. For purposes of the present disclosure, proximal and distal directions are directions normal to the reference plane (and, therefore, parallel to anatomic axis $A_T$ after implantation of tibial prosthesis 10).

Tibial bearing component 12 is a "high-flexion" prosthetic component, in that the geometry and configuration of articular compartments 16, 18 cooperate with a femoral component (e.g., femoral component 20 of FIGS. 4A and 4B) to allow a large total range of motion. For example, a high-flexion knee prosthesis may enable a flexion range of as little as 130 degrees, 135 degrees, or 140 degrees and as large as 150 degrees, 155 degrees or 170 degrees, or may enable any level of flexion within any range defined by any of the foregoing values. In the context of high-flexion components, enablement of high flexion refers to the ability of a prosthesis to reach a given level of flexion by articulation of condyles 22, 24 with articular compartments 16, 18 and without impingement of any prosthesis structures with non-articular prosthesis surfaces. While tibial bearing component 12 enables high prosthesis flexion as described below, it is of course appreciated that the actual level of flexion achievable for any given patient is also dependent upon various anatomical and surgical factors.

For tibial bearing component 12, high flexion may be enabled by one or both of two features. First, tibial bearing component 12 includes differential heights $H_L$, $H_M$, with $H_L$ less than $H_M$ to facilitate posterior rollback of lateral condyle 24 in deep flexion (as described in detail below). For purposes of the present disclosure, heights $H_L$, $H_M$ are measured normal to slope line 46. When lateral condyle 24 is allowed to roll back in this manner, potential impingement between the articular surface of condyle 24 and/or the adjacent femoral bone against the posterior/lateral periphery of tibial bearing component 12 is avoided. Second, the medial/posterior periphery of tibial bearing component 12 includes posterior chamfer surface 27 (disposed at the posterior periphery of medial articular compartment 16, as shown in FIG. 3A), which slopes in a posterior direction from proximal-to-distal. Chamfer 27 creates an absence of a vertical peripheral wall immediately posterior of medial articular compartment 16, thereby creating a corresponding space the adjacent femoral bone and/or adjacent soft tissues in deep flexion. An exemplary embodiment of posterior/medial chamfer 27 is described in detail in U.S. patent application Ser. No. 13/229,103, filed Sep. 9, 2011 and entitled MOTION FACILITATING TIBIAL COMPONENT FOR A KNEE PROSTHESIS, the entire disclosure of which is hereby expressly incorporated herein by reference.

High flexion is also accommodated by differential in curvature between medial and lateral condyles 22, 24. For example, lateral condyle 24 of femoral component 20 may have a larger radius of curvature than medial condyle 22 thereof. An exemplary femoral component is described in U.S. Pat. No. 6,770,099, filed Nov. 19, 2002, titled FEMORAL PROSTHESIS, the entire disclosure of which is expressly incorporated by reference herein. During flexion and extension, the larger lateral condyle 24 of femoral component 20 tends to travel a greater distance along lateral articular track 28 of tibial bearing component 12 as compared to the smaller medial condyle 22 of femoral component 20. This difference in distance traveled over a given range of knee flexion may be described as "big wheel/little wheel" movement, and is a feature which enables high flexion of the knee prosthesis by encouraging advancement of lateral condyle 24 toward the posterior edge of lateral articular compartment 18 at high levels of flexion.

In tibial bearing component 12, medial and lateral distal-most points 42, 44 are shifted anteriorly with respect to predicate prostheses which enable comparably high levels of flexion, as described below. For purposes of the present disclosure, the relative anterior/posterior location of distal-most points 42, 44 are measured by the distances $AP_{DM}$, $AP_{DL}$ of distal-most points 42, 44 from the anterior edge of the tibial prosthesis (FIGS. 3A and 3B). For purposes of comparison, distances $AP_{DM}$, $AP_{DL}$ may each be expressed as a percentage of the overall anteroposterior extent $AP_M$, $AP_L$, of medial and lateral prosthesis portions, which is inclusive tibial bearing component 12 and tibial baseplate 14 (FIGS. 1A, 3A and 3B) and is measured e extrapolated articular tracks 26, 28 (as shown in FIG. 1A and described herein). For example, if distal-most point 42 were located in the middle of overall anteroposterior extent $AP_M$ of medial articular compartment 16, then distal-most point 42 would be considered to be disposed at an anteroposterior location of approximately 50%. If distal-most point 42 were located near the posterior edge of articular compartment 16, then distal-most point would be near a 100% anteroposterior location. Conversely, if distal-most point 42 were located near the anterior edge of articular compartment 16, the distal-most point 42 would be near a 0% anteroposterior location.

For purposes of the present disclosure, medial anterior/posterior extent $AP_M$ (FIG. 1A) of the medial portion of tibial baseplate 14 is found by extrapolating medial articular track 26 anteriorly and posteriorly to intersect the periphery of baseplate 14 (in similar fashion to the intersection points used to define posterior line 34 described above), then measuring the distance between the resulting medial posterior and anterior intersection points. Similarly, lateral anterior/posterior extent $AP_L$ (FIG. 1A) of the lateral portion of tibial baseplate 14 is found by extrapolating the linear anterior portion of lateral articular track 28 anteriorly and posteriorly to intersect the periphery of baseplate 14, then measuring the distance between the resulting lateral posterior and anterior intersection points.

Figure 3C:
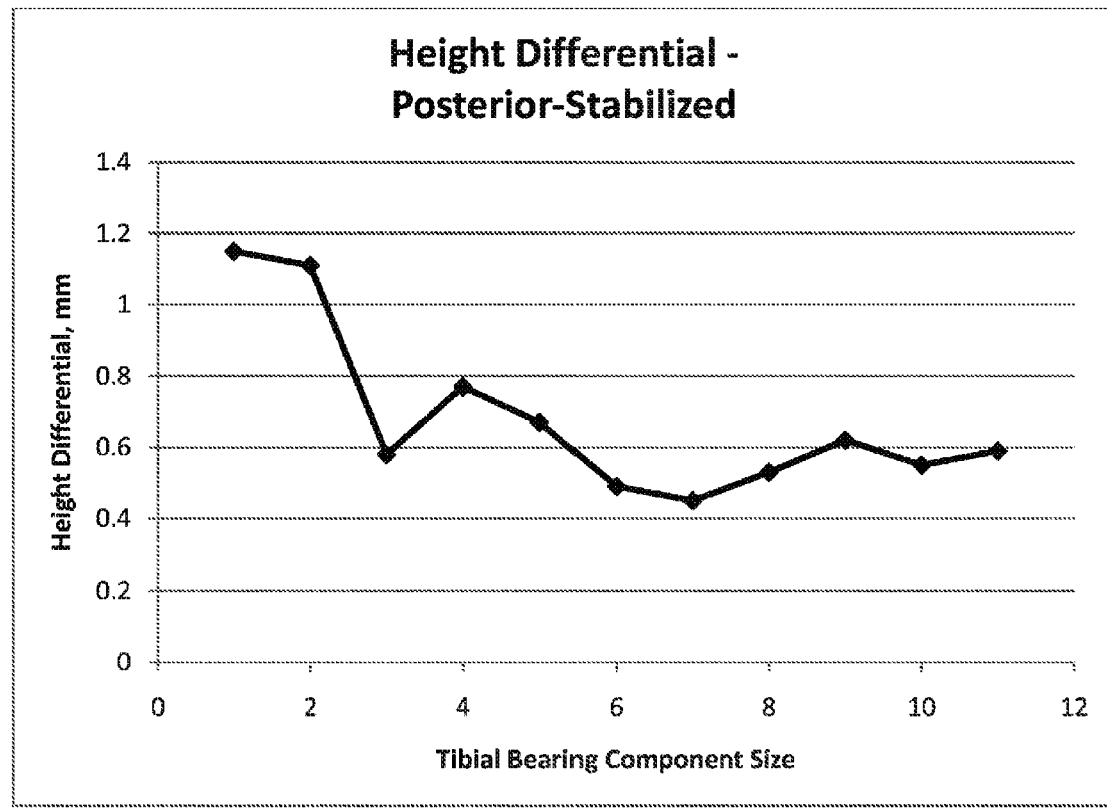
FIG. 3C is a graph plotting the height differential between medial and lateral posterior compartment edges for various sizes of posterior-stabilized tibial bearing components in accordance with the present disclosure.
Figure 3D:
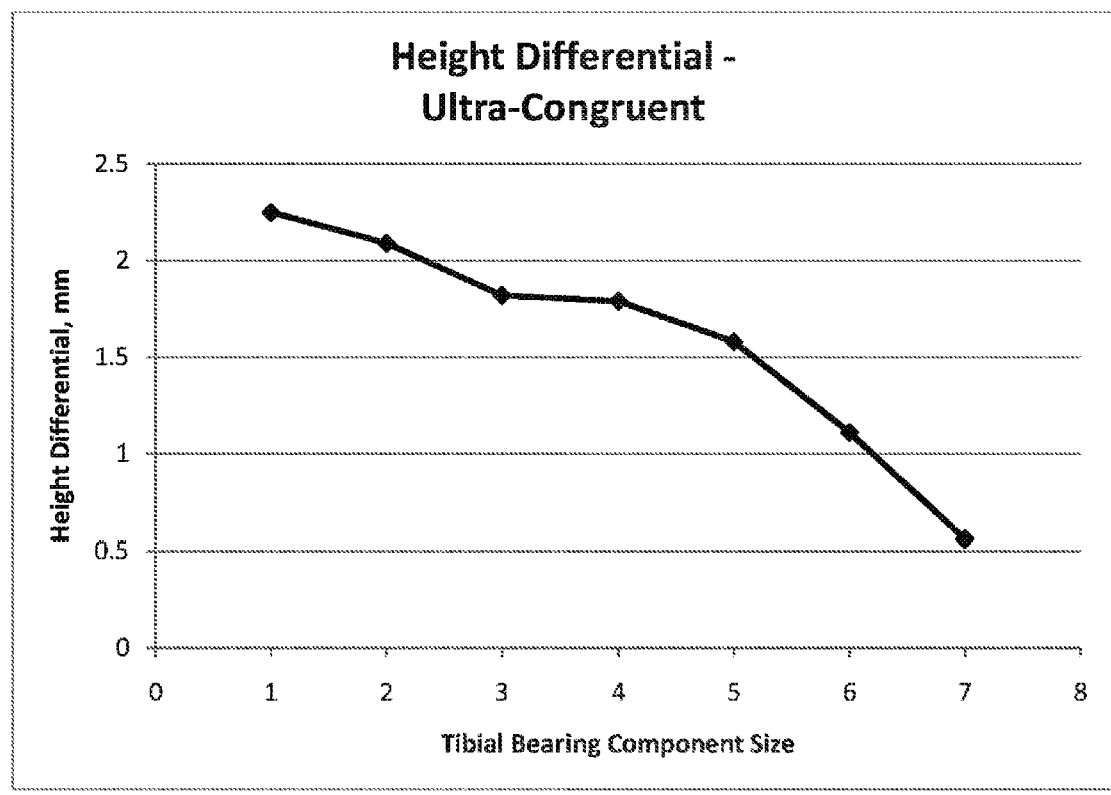
FIG. 3D is a graph plotting the height differential between medial and lateral posterior compartment edges for various sizes of ultra-congruent tibial bearing components in accordance with the present disclosure.
Figure 3E:
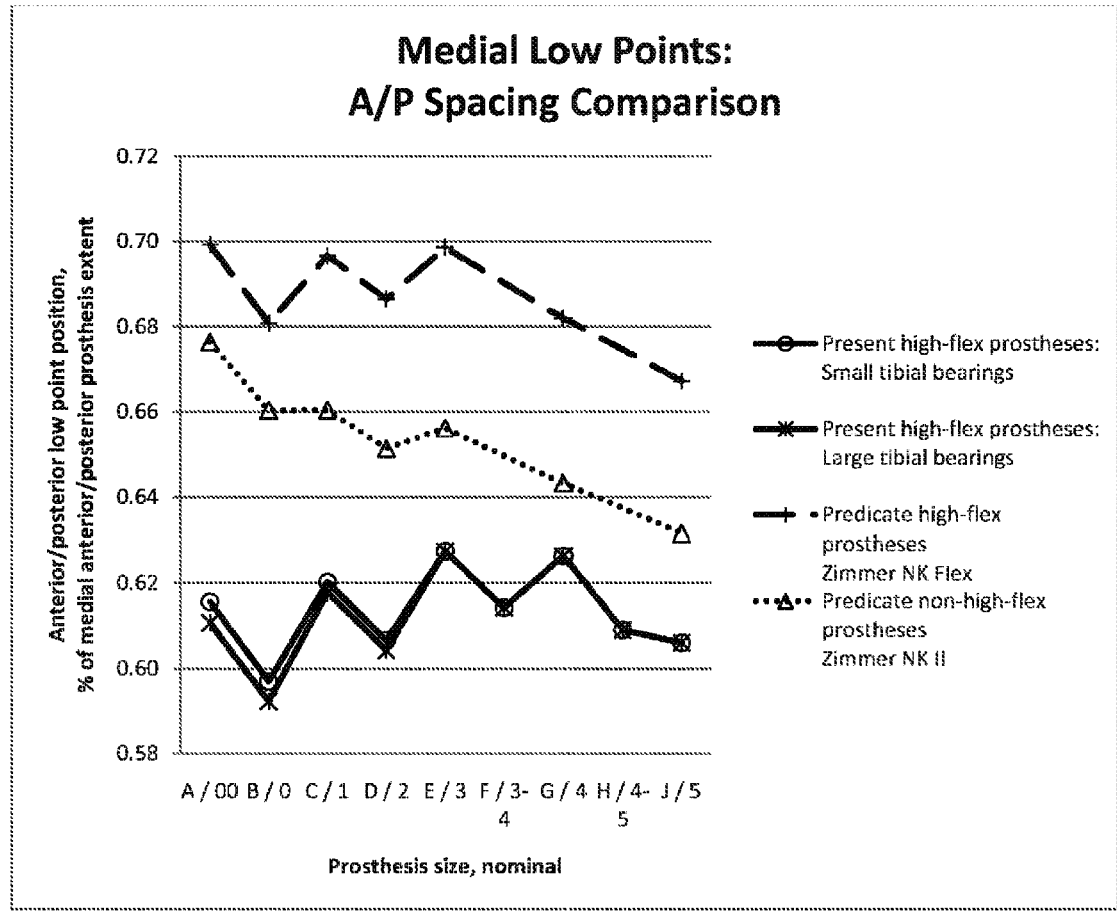
FIG. 3E is a graph plotting the anterior/posterior position of medial distal-most points of an articular surface for tibial bearing components in accordance with the present disclosure and prior art tibial bearing components (where prior art devices are listed as "predicate")

Turning to FIG. 3E, a graphical representation of the anterior/posterior position of medial distal-most point 42 (FIG. 3A) is illustrated as compared to predicate high-flexion and non-high-flexion prostheses. In tibial bearing component 12, the anterior/posterior position of medial distal-most point 42 (FIG. 3A) is in the range of 59% to 63% when implanted at an anterior/posterior slope S equal to 5 degrees. By comparison, one prior art high-flexion device is the Zimmer Natural Knee Flex Ultracongruent Tibial Bearing Component, which places its corresponding medial distal-most point in the range of 67% and 70% when implanted at a slope angle S of 5 degrees. Thus, the prior art Zimmer Natural Knee Flex Ultracongruent Tibial Bearing Component defines medial low points which are consistently posterior of medial distal-most point 42. On the other hand, the prior art Zimmer Natural Knee Ultracongruent Tibial Bearing Component places its corresponding medial distal-most point between 63% and 68% when implanted at a slope angle S of 5 degrees, but the Zimmer Natural Knee II Ultracongruent Tibial Bearing Component does not enable high flexion at least up to 130 degrees.

Figure 3F:
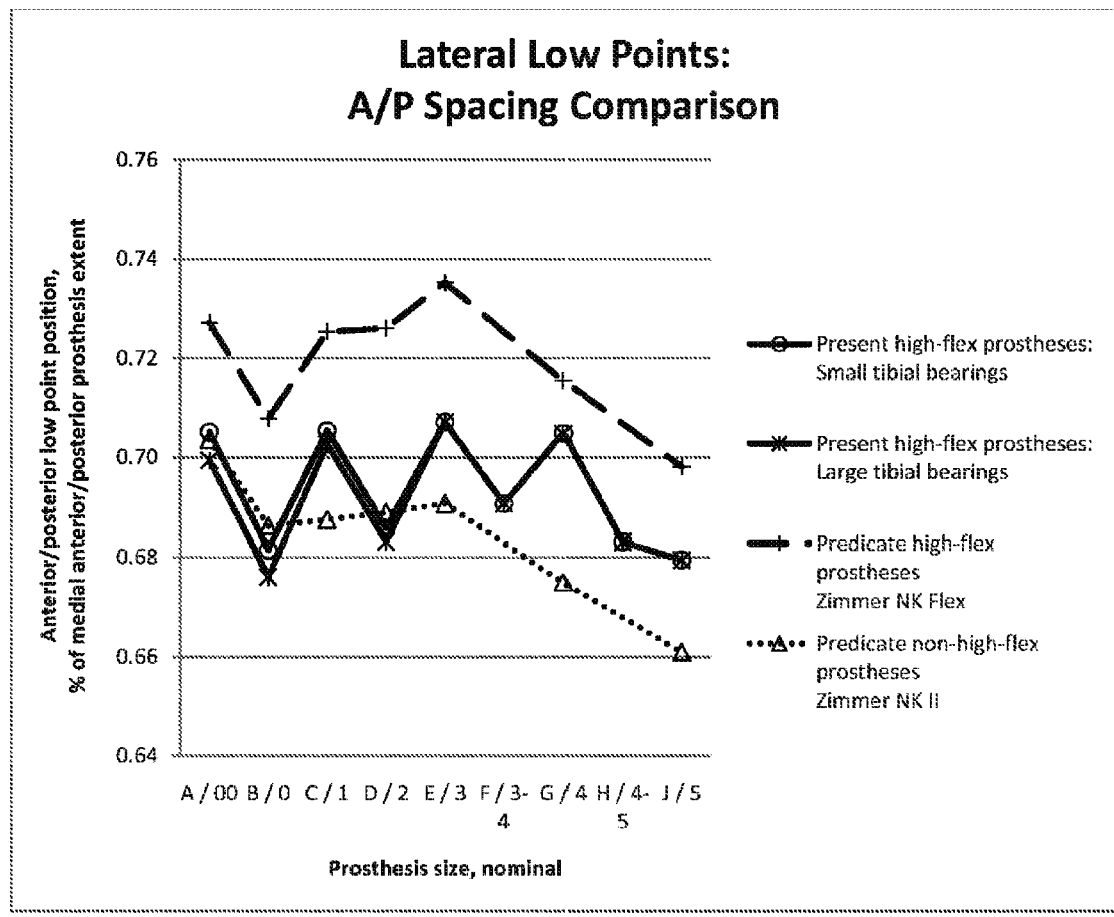
FIG. 3F is a graph plotting the anterior/posterior position of lateral distal-most points of an articular surface for tibial bearing components in accordance with the present disclosure and prior art tibial bearing components (where prior art devices are listed as "predicate")

As for lateral compartment 18 (FIGS. 3B and 3F) of tibial bearing component 12, distal-most point 44 has an anterior/posterior position of between 68% and 74%. The prior art high-flexion design, the Zimmer Natural Knee Flex Ultracongruent Tibial Bearing Component mentioned above, places such lateral distal-most points at between 70% and 73% when implanted at a slope angle S of 5 degrees. The non-high-flexion prior art design, the Zimmer Natural Knee II Ultracongruent Tibial Bearing Component mentioned above, places its distal-most point at between 66% and 70.5% when implanted at a slope angle S of 5 degrees.

Thus, the present ultracongruent prosthesis, as exemplified by tibial bearing component 12, blends a high-flexion design enabling at least 130 degrees of knee flexion with low points that are relatively further anterior as compared to prior art ultracongruent prostheses. Advantageously, this anterior low-point shift discourages "paradoxical movement," or movement between the femur and tibia in an opposite pattern from normal articulation. For example, the anterior shift of distal-most points 42, 44 inhibits anterior sliding of femoral component 20 with respect to tibial bearing component 12 when the knee is articulating from extension toward early flexion. Such early-flexion articulation is normally accompanied by a slight posterior shift in the contact points between condyles 22, 24 of femoral component 20 and articular compartments 16, 18 of tibial bearing component 12. This posterior shift is facilitated—and a paradoxical anterior shift is inhibited—by the relative anterior positioning of distal-most points 42, 44. Meanwhile, the potential of high-flexion articulation is preserved by the high-flexion features incorporated into tibial bearing component 12, as described in detail herein.

The above discussion regarding anterior shift of articular surface low points refers to exemplary ultracongruent (UC) type tibial bearing components. However, such anterior shift may be applied to tibial bearing components of other designs, such as cruciate-retaining (CR) and posterior-stabilized (PS) designs.

4. Articular Features: Differential Conformity in Medial/Lateral Articular Compartments.

Figure 4C:
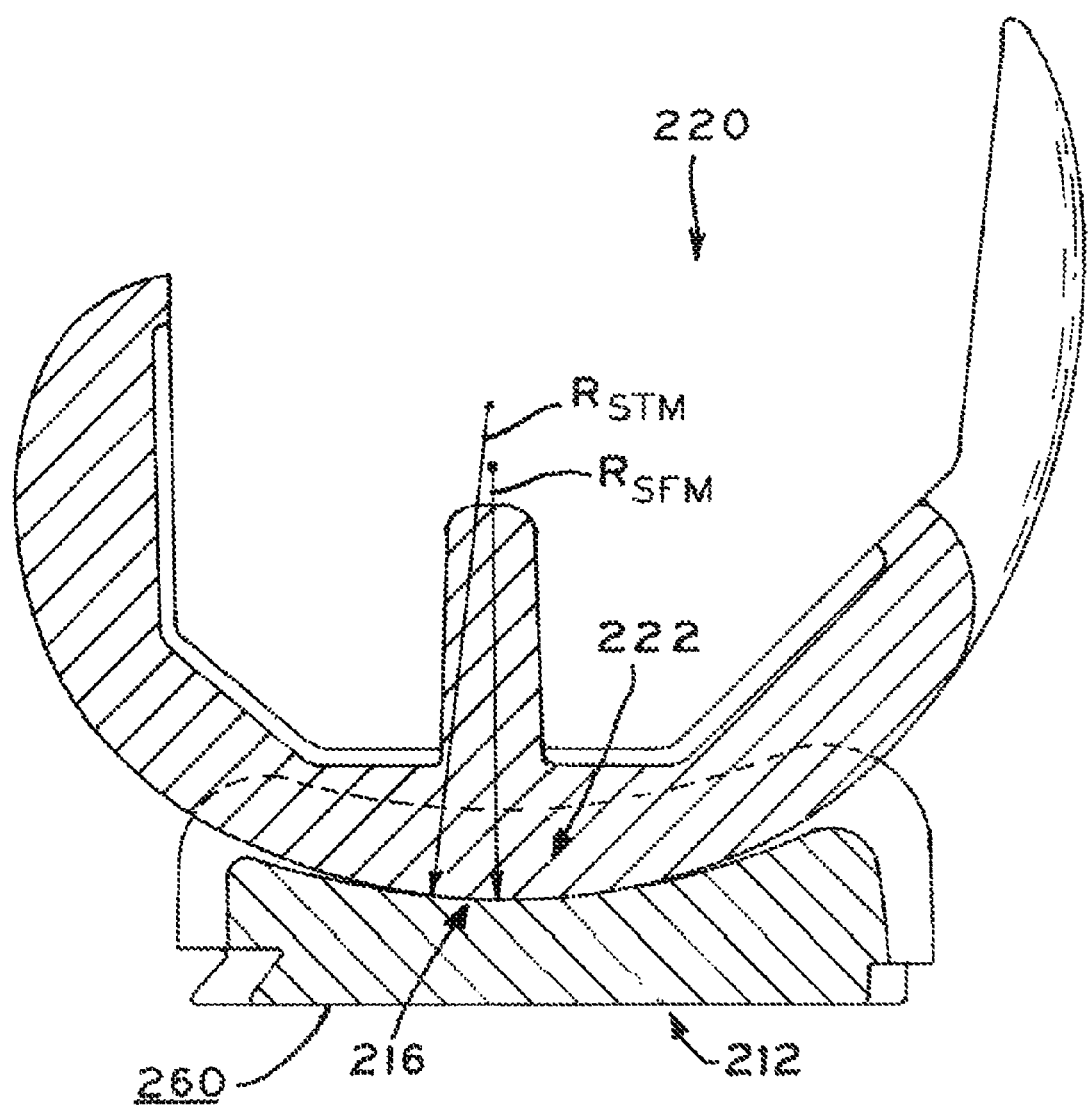
FIG. 4C is an elevation, cross-sectional view of the tibial bearing and femoral components shown in FIG. 4A, taken in a sagittal plane through the medial articular condyle and articular compartment thereof.

Referring now to FIGS. 4A-4C, femoral component 220 and tibial bearing component 212 are shown. For purposes of the following discussion, femoral component 20 and tibial bearing component 12 will be described in the context of FIGS. 4A-4C, it being appreciated that any potential prosthesis design (e.g., PS, UC and CR type femoral components) may each include the present described features as noted above.

Femoral component 20 cooperates with tibial bearing component 12 to provide relatively low conformity between lateral condyle 24 and lateral articular compartment 18, and relatively high conformity between medial condyle 22 and medial articular compartment 16.

A convex surface may be considered to be highly conforming with a corresponding concave surface where the two surfaces have similar or identical convex and concave geometries, such that the convex surface "nests" or tightly interfits with the concave surface. For example, a hemisphere having a radius perfectly conforms (i.e., defines high conformity) with a corresponding hemispherical cavity having the same radius. Conversely, the hemisphere would have no conformity with an adjacent flat or convex surface.

Femoral condyles 22, 24 define a coronal conformity with tibial articular compartments 16, 18, respectively, as shown in FIG. 4A. Similarly, femoral condyles 22, 24 define sagittal conformity with the corresponding articular compartments 16, 18, respectively, as shown in FIG. 4B. Thus, medial condyle 22 cooperates with medial articular compartment 16 to define a medial conformity comprised of both a medial sagittal conformity and a medial coronal conformity. Similarly, lateral femoral condyle 24 cooperates with lateral articular compartment 18 to define a lateral conformity comprised of the lateral sagittal conformity and lateral coronal conformity. Although only a single prosthesis is shown in FIGS. 4A-4C, it is contemplated that conformity may be similarly defined across a range of prosthesis sizes within a particular prosthesis design.

For purposes of the present disclosure, any given component of conformity is defined as a ratio of two radii. Referring to FIG. 4A, a lateral coronal conformity is defined by the ratio of the coronal radius of lateral articular compartment 18 of tibial bearing component 12 along lateral articular track 28, which is illustrated as radius $R_{CTL}$ (where CTL stands for coronal, tibial, lateral) to the corresponding coronal radius of lateral condyle 24 of femoral component 20, illustrated as radius $R_{CFL}$ (where CFL denotes coronal, femoral, lateral). The conformity defined by $R_{CTL}:R_{CFL}$ is a number greater than 1, because femoral condyle 24 is designed to fit within lateral articular compartment 18 to define point contact therewith, as described in detail above.

Similarly, medial coronal conformity is defined by the ratio $R_{CTM}:R_{CFM}$ (where M denotes medial). Sagittal conformity between lateral condyle 24 and lateral articular compartment 18 is defined as the ratio $R_{STL}:R_{SFL}$ (FIG. 4B, where S denotes sagittal, F denotes femoral, T denotes tibia, and L denotes lateral). Medial condyle 22 defines sagittal conformity with medial articular compartment 16 in a similar fashion, as $R_{STM}:R_{SFM}$ (FIG. 4C). In exemplary embodiments ultra-congruent type prostheses, lateral sagittal conformity ratio $R_{STL}:R_{SFL}$ may be between 1.0 and 1.7, and medial sagittal conformity ratio $R_{STM}:R_{SFM}$ may be between 1.0 and 1.9, with lateral ratio $R_{STL}:R_{SFL}$ greater than medial ratio $R_{STM}:R_{SFM}$ by at least 0.2 through at least a portion of the flexion range. In exemplary embodiments of posterior-stabilized type prostheses, lateral sagittal conformity ratio $R_{STL}:R_{SFL}$ may be between 1.4 and 1.8, and medial sagittal conformity ratio $R_{STM}:R_{SFM}$ may be between 1.0 and 1.8, with lateral ratio $R_{STL}:R_{SFL}$ greater than medial ratio $R_{STM}:R_{SFM}$ by at least 0.4 through at least a portion of the flexion range. In exemplary embodiments of cruciate-retaining type prostheses, lateral sagittal conformity ratio $R_{STL}:R_{SFL}$ may be between 1.1 and 2.6, and medial sagittal conformity ratio $R_{STM}:R_{SFM}$ may be between 1.1 and 2.2, with lateral ratio $R_{STL}:R_{SFL}$ greater than medial ratio $R_{STM}:R_{SFM}$ by at least 0.5 through at least a portion of the flexion range.

Predicate devices have defined varying levels of medial and lateral conformity between the femoral condyles thereof and the corresponding tibial articular compartments. Generally speaking, in the case of tibial bearing component 12 and femoral component 20, the lateral conformity (defined by ratios $R_{STL}:R_{SFL}$ and $R_{CTL}:R_{CFL}$) is approximately equal to the lowest lateral conformity defined by the predicate devices, while the medial conformity (defined by ratios $R_{STM}:R_{SFM}$ and $R_{CTM}:R_{CFM}$) is approximately equal to the highest medial conformity defined by predicate devices.

5. Articular Features: Low Barrier to Femoral Rollback in Posterior/Lateral Articular Compartment.

As used herein, "jump height" refers to the proximal/distal distance that a portion of femoral component 20 must traverse to sublux from the tibial bearing component 12. Referring to FIGS. 3A and 3B, medial and lateral articular compartments 16, 18 of tibial bearing component 12 are shown in cross-section to illustrate the location of distal-most points 42, 44. The vertical distance between respective distal-most points 42, 44 (FIGS. 3A, 3B) On the articular surface of tibial bearing component 12 to the highest point at the edge of such articular surface is the jump height of tibial bearing component 12. Referring to FIG. 3A, medial femoral condyle 22 (FIG. 2) would have to move proximally by a distance $H_M$ to move the contact point between condyle 22 and medial compartment 16 from distal-most point 42 to the highest point along the posterior edge of medial compartment 16. For purposes of the present disclosure, such "highest point" is the point at which a posterior extrapolation of medial articular track 26 reaches its proximal peak as the extrapolated line advances toward the posterior edge of the tibial bearing periphery.

Thus, $H_M$ may be referred to as the posterior jump height established by the particular curvature and geometry of medial articular compartment 16. Jump height $H_M$ is designed to provide an appropriately low barrier to desired posterior translation of the contact point between medial condyle 22 and medial compartment 16 along medial articular track 26, while also being sufficiently high to ensure that condyle 22 remains safely engaged with articular compartment 16 throughout the range of flexion provided by the knee prosthesis.

Referring to FIG. 3B, lateral jump height $H_L$ is lower than medial jump height $H_M$. Advantageously, setting $H_L$ lower than $H_M$ facilitates femoral rollback by presenting a relatively lower barrier to lateral condyle 24 to traverse the posterior arcuate portion 30 of lateral articular track 28 when the knee prosthesis is in deep flexion. In an exemplary embodiment, the height differential between lateral and medial jump heights $H_L$, $H_M$ are between 0.4 mm and 2.3 mm, which has been found to be an ideal range in order to facilitate femoral rollback while maintaining appropriate barrier to subluxation in both medial and lateral compartments 16, 18.

For example, FIG. 3C illustrates the height differential between jump heights $H_L$, $H_M$ for eleven sizes of a posterior-stabilized tibial component design in accordance with the present disclosure, when such posterior-stabilized components are implanted with a tibial slope angle S (FIGS. 3A and 3B) of 3 degrees. As shown in FIG. 3C, the jump height differential ranges from 1.15 mm in the smallest prosthesis size, then trends generally downwardly to a minimum of 0.45 mm for the seventh of 11 sizes. In other exemplary embodiments, the jump height differential may be as large as 2.68 mm. It is contemplated that a jump height differential up to 3 mm may be used with prostheses according to the present disclosure.

FIG. 3D graphically depicts the jump height differentials between jump heights $H_L$, $H_M$ for seven sizes of an ultra-congruent tibial component design in accordance with the present disclosure, when such ultra-congruent components are implanted with a tibial slope angle S (FIGS. 3A and 3B) of 5 degrees. As illustrated, the jump height differential ranges from 2.25 mm in the smallest prosthesis size, then trends generally downwardly to a minimum of 0.56 mm for the largest of the seven sizes. By comparison, jump height differential for the above-mentioned prior art high-flexion prosthesis, i.e., the Zimmer Natural Knee Flex Ultracongruent Tibial Bearing Component discussed above, range from 0.09 mm to 0.39 mm. For non-high-flexion prior art designs, such as the Zimmer Natural Knee II Ultracongruent Tibial Bearing Component discussed above, the jump height differential ranges from 0.22 mm to 0.88 mm.

Similar to the trending of clocking angle α (FIG. 1A) described in detail above, a majority of prosthesis sizes represented by FIGS. 3C and 3D experience a decrease in jump height differential from smaller to larger sizes, and an overall substantial decrease is exhibited in the difference between the smallest and largest sizes. Therefore, it may be said that the trend in jump height differential for posterior-stabilized and ultra-congruent tibial bearing components made in accordance with the present disclosure is generally downward across the range of sizes.

6. Articular Features: Progressively Angled Posterior Spine Surface

Figure 5A:
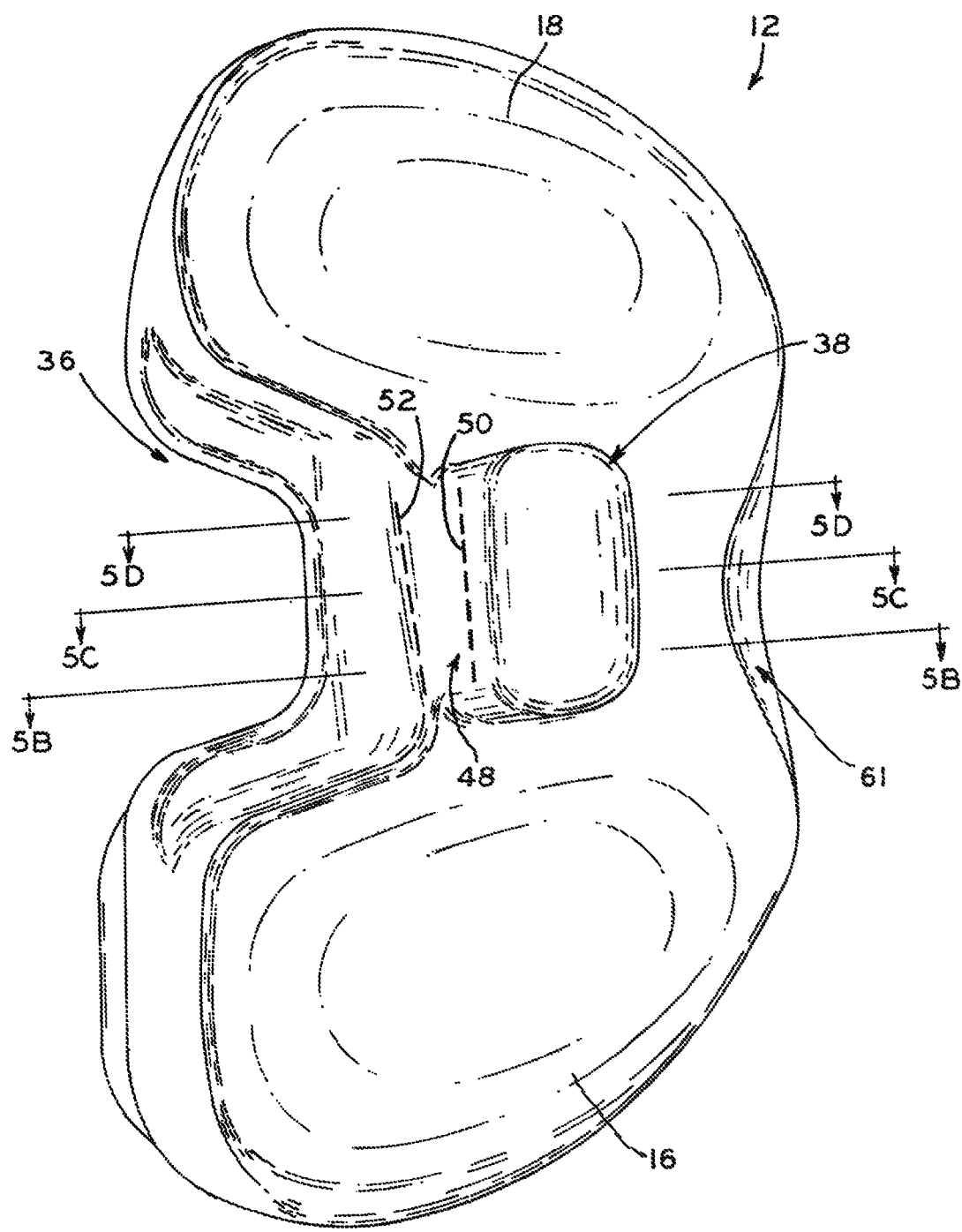
FIG. 5A is a top perspective view of the tibial bearing component shown in FIG. 1A.

Turning now to FIG. 5A, spine 38 of tibial bearing component 12 defines posterior articular surface 48, which is designed to articulate with femoral cam 40 (FIG. 2) of femoral component 20 during prosthesis articulation, and particularly in mid- and deep flexion. As described in detail below, posterior articular surface 48 defines a progressively angled surface from a proximal, symmetric beginning to an angled distal end. This progressive angling accommodates external rotation of femoral component 20 in deep flexion.

In use, initial contact line 50 represents the line of contact between femoral cam 40 and posterior surface 48 when femoral cam 40 initially contacts spine 38 during flexion, while deep flexion contact line 52 represents the line of contact therebetween when femoral cam 40 has moved posteriorly down posterior surface 48 to a deep flexion orientation. The total distance traversed by femoral cam 40 along posterior surface 48 is referred to as the articular extent of posterior surface 48 as measured along a proximal/distal direction. In FIG. 5A, this articular extent may be represented as the distance from initial contact line 50 to deep-flexion contact line 52. In an exemplary embodiment, the articular extent of posterior surface 48 may be as little as 2 mm, 3 mm or 5 mm and as large as 10 mm, 15 mm or 20 mm, or may be any value within any range defined by any of the foregoing values.

For purposes of the present disclosure, spine 38 is considered to be bisected by a sagittal plane into medial and lateral halves, such that a posterior spine centerline is formed along the intersection between the bisecting sagittal plane and posterior surface 48. Posterior surface 48 defines a series of medial/lateral tangent lines, each of which is tangent to posterior surface 48 at the spine centerline. For purposes of illustration, a medial/lateral tangent line at the proximal end of posterior articular surface 48 is illustrated as initial contact line 50 in FIG. 5A, while a medial/lateral tangent line at the distal end thereof is illustrated as deep flexion contact line 52. In normal articulation, initial contact line 50 will be coincident with the proximal-most medial/lateral tangent line and deep-flexion contact line 52 will be coincident with the distal-most medial/lateral tangent line, as shown in FIG. 5A and described herein. However, it is appreciated that a certain amount of variation from the designed articular profile of a prosthesis is normal for in vivo prosthesis articulation. Therefore, the actual lines of contact between femoral cam 40 and posterior surface 48 during prosthesis use may deviate slightly from the intended medial/lateral tangent lines. For, purposes of the present disclosure, prosthesis characteristics such as contact lines 50, 52 are described solely in terms of the designed articular profile of the prosthesis when tibial and femoral components 12, 20 are articulated through their nominal range of motion.

As illustrated in FIG. 5A, contact lines 50 and 52 are not parallel, with contact line 50 running medially/laterally along a direction parallel to a coronal plane, and contact line 52 oblique to the coronal plane such that line 52 advances posteriorly as it extends laterally (and, concomitantly, also advances anteriorly as it extends medially). Both of lines 50, 52 are parallel to the transverse plane, such that the angle formed between lines 50, 52 is solely with respect to the coronal plane. In an exemplary embodiment, the angle formed between initial contact line 50 and deep-flexion contact line 52 may be as large as 3 degrees. However, it is contemplated that other exemplary embodiments may form such angle at 7 degrees, and that an angle up to 10 degrees may be used in some instances.

Figure 5B:
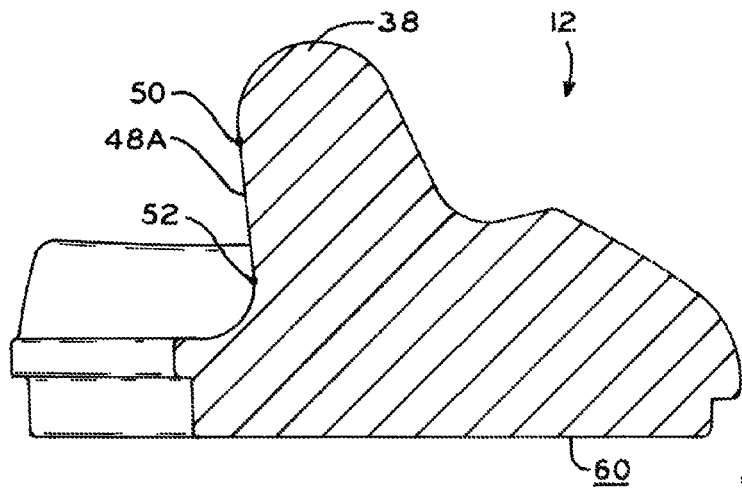
FIG. 5B is a sagittal, cross-sectional view of the tibial bearing component shown in FIG. 5A, taken along the line 5B-5B of FIG. 5A.

Turning to FIG. 5B, a cross-section of the medial portion of spine 38 is shown. Posterior articular surface 48 defines medial surface 48A, extending between initial contact line 50 and deep flexion contact line 52. As described in detail below, if posterior articular surface 48 defined articular surface line 48A across the medial/lateral extent of spine 38, spine 38 would be symmetric and external femoral rotation in deep flexion would not be accommodated in the manner provided by the asymmetric spine 38 of the present disclosure.

Figure 5C:
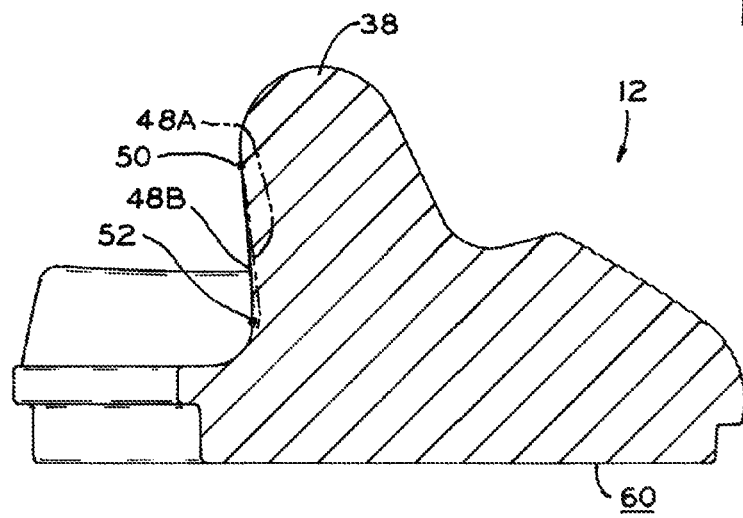
FIG. 5C is another sagittal, cross-sectional view of the tibial bearing component shown in FIG. 5A, taken along the line 5C-5C of FIG. 5A.

Turning to FIG. 5C, a cross-section medially/laterally bisecting spine 38 is shown. Articular surface line 48B is defined by posterior articular surface 48 at this cross-section, and is shown juxtaposed against a hidden line representing articular surface line 48A from FIG. 5B. As illustrated in FIG. 5C, lines 48A and 48B both extend from a common proximal point along initial contact line 50. However, the distal point of line 48B (along deep flexion contact line 52) has moved posteriorly with respect to the distal end of line 48A. This posterior movement reflects a progressively increasing material buildup along the base or distal end of posterior articular surface 48, such that this base is increasingly "augmented" by additional spine material as the deep flexion contact line 52 traverses from medial to lateral. Stated another way, spine 38 is effectively thicker in the region of contact line 52 at the bisecting cross-section of FIG. 5C as compared to the medially-biased cross-section of FIG. 5B.

Figure 5D:
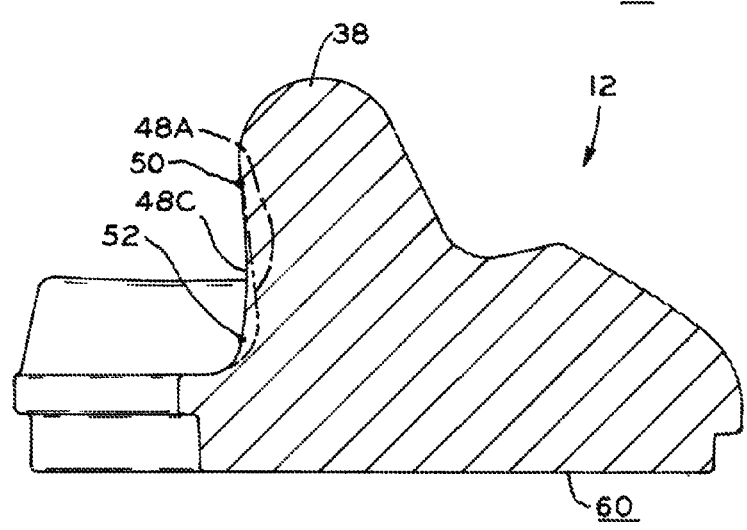
FIG. 5D is another sagittal, cross-sectional view of the tibial bearing component shown in FIG. 5A, taken along the line 5D-5D of FIG. 5A.

Turning to FIG. 5D, it can be seen that the process of material thickening or augmentation described above with respect to FIG. 5C has grown and further intensified. Thus, while line 48C still originates from a common proximal point with lines 48A, 48B along initial contact line 50, the distal end of line 48C along deep flexion contact line 52 has moved further posteriorly with respect to line 48A. Thus, at the lateral edge of posterior articular surface 48, the base of spine 38 is thicker still.

In effect, the changing geometry of posterior articular surface 48 of spine 38 from medial to lateral has the effect of imparting an angled appearance to the distal, deep-flexion portion of posterior articular surface 48. The remainder of spine 38 is generally symmetrical about the sagittal plane, as illustrated in FIG. 5A. As femoral cam 40 traverses posterior articular surface 48 from the initial contact line 50 in mid flexion to the deep flexion contact line 52 in deep flexion, the angle of the surface encountered by femoral cam 40 changes, thereby changing the angle of the medial/lateral tangent lines described above with respect to the coronal plane. In an exemplary embodiment, the initial transition from non-angled contact lines (e.g., initial contact line 50) to angled contact lines (e.g., deep-flexion contact line 52) is spaced from a proximal terminus of posterior surface 48 by a distance of between 0% and 100% of the total proximal/distal extent of posterior articular surface 48 (i.e., the transition may occur immediately or at the very end of the flexion range, or anywhere in between). For purposes of the present disclosure, the proximal/distal extent of posterior articular surface 48 is the total distance traversed by femoral cam 40 throughout the range of flexion motion. In the illustrative embodiment of FIG. 5A, this total proximal/distal articular extent of posterior articular surface 48 (i.e., the distance between a proximal start point and a distal end point) may be as little as 2 mm, 3 mm or 4 mm and as large as 17 mm, 18.5 mm or 20 mm, or may be any value within any range defined by any of the foregoing values. The proximal end point coincides with an initial contact between cam 40 and posterior articular surface 48 at a prosthesis flexion of between 75 degrees flexion and 93 degrees flexion, while the distal end point is at a final contact between cam 40 and posterior articular surface 48 at a prosthesis flexion of 155 degrees.

Advantageously, the extent of the angling of posterior articular surface 48 changes with changing levels of flexion. More particularly, the angle grows by an amount corresponding to the expected increase in external rotation of femoral component 20 as flexion progresses, thereby ensuring that line contact is made between femoral cam 40 and posterior articular surface 48 throughout the range of flexion of prosthesis 10. In an exemplary embodiment, a maximum external rotation of femoral component 20 occurs between 120 degrees flexion and 155 degrees flexion.

In contrast, if the posterior surface 48 of spine 38 had no angled surface portions (i.e., if initial contact line 50 were parallel to deep flexion contact line 52) femoral cam 40 would transition from line contact along initial contact line 50 to an increasingly point-like contact near the medial edge of posterior articular surface 48.

In the exemplary embodiment illustrated in the figures, femoral cam 40 is symmetrical in nature, such that accommodation of deep flexion external rotation without diminishment of cam/spine contact area is accomplished solely through the above described lateral augmentation of posterior articular surface 48 at the distal base of spine 38. Femoral cam 40 is described in detail in: U.S. Provisional Patent Application Ser. No. 61/561,658, filed on Nov. 18, 2011 and entitled FEMORAL COMPONENT FOR A KNEE PROSTHESIS WITH IMPROVED ARTICULAR CHARACTERISTICS; U.S. Provisional Patent Application Ser. No. 61/579,873, filed on Dec. 23, 2011 and entitled FEMORAL COMPONENT FOR A KNEE PROSTHESIS WITH IMPROVED ARTICULAR CHARACTERISTICS; U.S. Provisional Patent Application Ser. No. 61/592,575 filed on Jan. 30, 2012 and entitled FEMORAL COMPONENT FOR A KNEE PROSTHESIS WITH IMPROVED ARTICULAR CHARACTERISTICS; U.S. Provisional Patent Application Ser. No. 61/594,113 filed on Feb. 2, 2012 and entitled FEMORAL COMPONENT FOR A KNEE PROSTHESIS WITH IMPROVED ARTICULAR CHARACTERISTICS; U.S. Provisional Patent Application Ser. No. 61/621,370 filed on Apr. 6, 2012 and entitled FEMORAL COMPONENT FOR A KNEE PROSTHESIS WITH IMPROVED ARTICULAR CHARACTERISTICS; U.S. Provisional Patent Application Ser. No. 61/621,372, filed on Apr. 6, 2012, and entitled FEMORAL COMPONENT FOR A KNEE PROSTHESIS WITH IMPROVED ARTICULAR CHARACTERISTICS; U.S. Provisional Patent Application Ser. No. 61/621,373, filed on Apr. 6, 2012 and entitled FEMORAL COMPONENT FOR A KNEE PROSTHESIS WITH IMPROVED ARTICULAR CHARACTERISTICS; U.S. patent application Ser. No. 13/459,061, filed on Apr. 27, 2012, now issued as U.S. Pat. No. 9,060,868 and entitled FEMORAL COMPONENT FOR A KNEE PROSTHESIS WITH IMPROVED ARTICULAR CHARACTERISTICS; U.S. patent application Ser. No. 13/459,064, filed on Apr. 27, 2012, now issued as U.S. Pat No. 8,932,365, and entitled FEMORAL COMPONENT FOR A KNEE PROSTHESIS WITH IMPROVED ARTICULAR CHARACTERISTICS; and in U.S. patent application Ser. No. 13/459,060, filed on Apr. 27, 2012, now issued as U.S. Pat. No. 9,308,095, and entitled FEMORAL COMPONENT FOR A KNEE PROSTHESIS WITH IMPROVED ARTICULAR CHARACTERISTICS. The entire disclosures of each of the above-identified patent applications are hereby expressly incorporated herein by reference.

7. Articular Features: Posterior Eminence Providing Media Lateral Stability While also Accommodating Hyperextension.

As noted above, FIGS. 6A and 6B illustrate an ultra congruent (UC) type tibial bearing component 112 designed for use with femoral component 120 lacking the femoral cam 40 found on femoral component 20 (FIG. 2). As also noted above, ultra congruent tibial bearing components such as component 112 lack spine 38 found on bearing component 12. Tibial bearing component 112 and femoral component 120 are otherwise substantially similar to tibial bearing component 12 and femoral component 20 described above, with reference numerals of components 112 and 120 analogous to the reference numerals used in components 12 and 20 respectively, except with 100 added thereto. Structures of tibial bearing component 112 and femoral component 120 correspond to similar structures denoted by corresponding reference numerals of tibial bearing component 12 and femoral component 20, except as otherwise noted. In one exemplary embodiment, femoral component 120 is similar or identical to cruciate-retaining (CR) femoral component 220 (FIGS. 4A and 4B).

In order to provide some medial/lateral constraint of femoral component 20, particularly in extension and early flexion configurations, posterior eminence 138 may be provided. As shown in FIG. 6A, femoral component 120 includes intercondylar notch 154 which, when in an extension orientation as shown, defines a width which provides minimal medial lateral clearance with posterior eminence 138. Thus, any forces tending to urge femoral component 120 medially or laterally upon the proximal articular surface of tibial bearing component 112 encounter resistance as the inwardly facing lateral and medial sidewalls $155_L$, $155_M$ of intercondylar notch 154 engage the lateral and medial sidewall portions $158_L$, $158_M$ of sidewall 158 of posterior eminence 138.

As best seen in FIG. 6A, anterior portion $158_A$ of sidewall 158 of posterior eminence 138 is generally arcuate and defines radius $R_{EA}$, thereby corresponding in shape to the inwardly facing anterior wall $155_A$ defining radius $R_{NA}$ which joins lateral and medial sidewalls $155_L$, $155_M$ to form intercondylar notch 154. In an exemplary embodiment, radius $R_{EA}$ is defined at the outer periphery of proximal surface 156, i.e., at the point where the planarity of proximal surface 156 gives way to the distally sloping profile of sidewall 158. Similarly, radius $R_{NA}$ of anterior wall $155_A$ is measured at that portion of anterior wall $155_A$ which is complimentary to radius $R_{EA}$ when femoral component 120 is seated upon tibial bearing component 112 in an extension orientation.

Thus, posterior eminence 138 and intercondylar notch 154 interfit with one another when femoral component 120 is in the extension orientation as shown. In an exemplary embodiment, radius $R_{EA}$ may be 4 mm and radius $R_{NA}$ may be 6 mm, such that a minimal clearance is provided between posterior eminence 138 and intercondylar notch 154 in the fully extended position of FIG. 6A.

Further, as best seen in FIG. 6B, the transition from proximal surface 156 to sidewall 158 is gradual and sloped, such that every potentially articular portion of posterior eminence defines a radius of at least 1 mm, including the sagittal/coronal radii $R_{SC1}$, $R_{SC2}$ defined by sidewall 158. Radii $R_{SC1}$, $R_{SC2}$ are shown denoted only in the sagittal perspective in FIG. 6D, it being understood that radii $R_{SC1}$, $R_{SC2}$ also extend around lateral and medial sidewall portions $158_L$, $158_M$. Thus, radii $R_{SC1}$, $R_{SC2}$ extend around the medial, anterior and lateral portions of sidewall 158, thereby forming the gradual rounded transition between proximal surface 156 to the surrounding articular surfaces of ultra-congruent tibial bearing component 112. Stated another way, any section plane perpendicular to a transverse plane (e.g., the transverse and coronal planes) taken through any of lateral, medial and anterior sidewall portions $158_L$, $158_M$, $158_A$ of sidewall 158 will define radii greater than 1 mm at such sidewall portions $158_L$, $158_M$, $158_A$, such as radii $R_{SC1}$, $R_{SC2}$. The posterior face of posterior eminence 138, which forms a portion of peripheral sidewall 172 of tibial bearing component 112, is not designed for articulation with any structure as femoral component 120 lacks any structure bridging the gap between medial and lateral condyles 122, 124 (such as, for example, femoral cam 40 of posterior-stabilized femoral component 20).

When femoral component 120 ethers a hyperextension configuration (i.e., when knee prosthesis 110 is articulated beyond full extension to a "backwards bend" of the knee), intercondylar notch 154 ascends the anterior portion of sidewall 158, gradually "beaching" or transitioning into contact between the patello-femoral groove adjacent intercondylar notch 154 and the medial and lateral portions of sidewall 158 over proximal surface 156. In an exemplary embodiment, such transition is designed to occur at 3.5 degrees of hyperextension (i.e., minus-3.5 degrees flexion), though other exemplary embodiments may experience the transition as high as 7 or 10 degrees of hyperextension. As shown in FIG. 6D, the level of hyperextension is controlled by the distance between anterior wall $155_A$ of intercondylar notch 134 and anterior portion $158_A$ of sidewall 158 in extension (as shown in FIG. 6D). This distance can be made smaller for an earlier engagement and larger for a later engagement.

The hyperextension "beaching" transition is further aided by the complementary angular arrangement of lateral and medial sidewalls $155_L$, $155_M$ of intercondylar notch 154 as compared to lateral and medial sidewall portions $158_L$, $158_M$ of posterior eminence 138. More particularly, FIG. 6A illustrates that angles $\mu_F$, $\mu_T$ are formed by sidewalls $155_L$, $155_M$ and $158_L$, $158_M$ of intercondylar notch 154 and posterior eminence 138, respectively, and are both arranged to converge anterior of posterior eminence 138 as shown. In the illustrative embodiment of FIG. 6A, angles $\mu_F$, $\mu_T$ are measured in a transverse plane with femoral component 120 seated upon tibial bearing component 112 in an extension orientation. Angles $\mu_F$, $\mu_T$ are large enough to guide and center femoral component 120 into engagement with posterior eminence 138 during hyperextension, but are small enough so that interaction between intercondylar notch 154 and posterior eminence 138 provides effective medial/lateral stability in extension and early flexion. In an exemplary embodiment, angle $\mu_T$, is 21.5 degrees and angle $\mu_F$ ranges from 21 degrees to 23 degrees through a range of prosthesis sizes. However, it is contemplated that angles $\mu_F$, $\mu_T$ would accomplish their dual roles of medial/lateral stability and hyperextension accommodation at any angle between 15 degrees and 30 degrees.

The distal portion of the patellofemoral groove or sulcus, which coincides with and gradually transitions into the anterior terminus of intercondylar notch 154, also has a shape which matches the profile of lateral and medial portions $158_L$, $158_M$ of sidewall 158. Advantageously, this matching shape and volume between intercondylar notch 154 and posterior eminence 138 cooperates with the gently sloped sidewall 158 to accommodate hyperextension by minimizing the abruptness of impact therebetween. Because hyperextension interaction is spread over a large area, potential abrasion of posterior eminence 138 by such interaction is also minimized, thereby potentially extending the service life of posterior eminence 138 and, ultimately, of tibial bearing component 112 in patients with hyperextending knees.

Figure 6C:
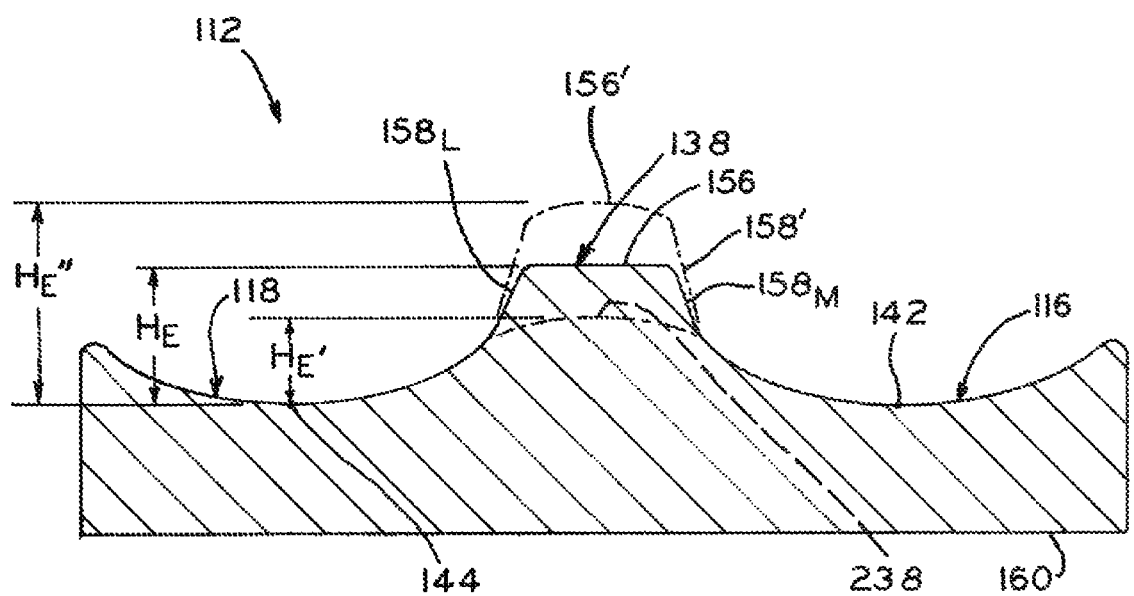
FIG. 6C is an elevation, cross-sectional view of tibial bearing component shown in FIG. 6A, taken in a coronal plane.
Figure 6D:
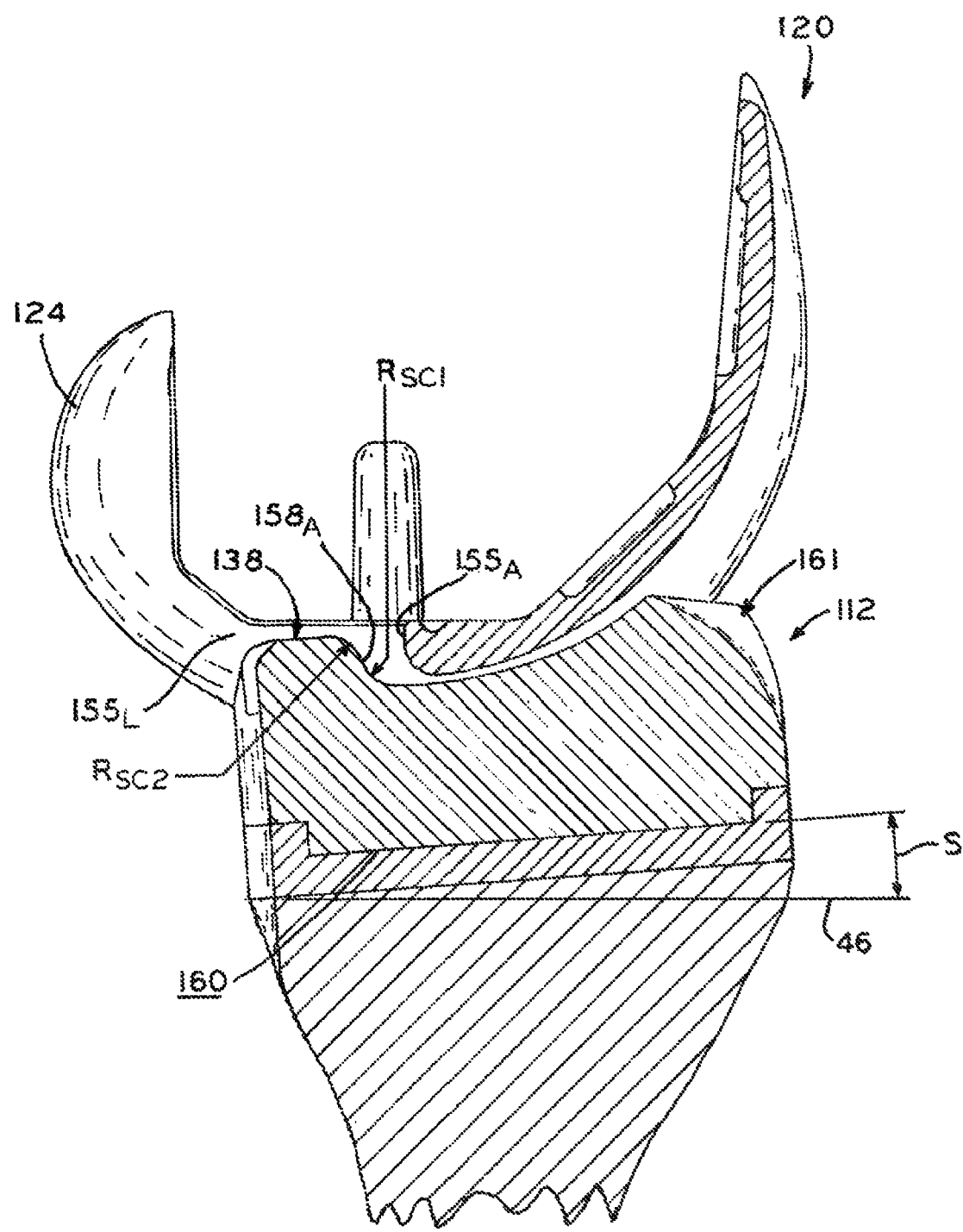
FIG. 6D is a sagittal, elevation, cross-sectional view of the tibial bearing component of FIG. 6A, in combination with a femoral component.
Figure 6E:
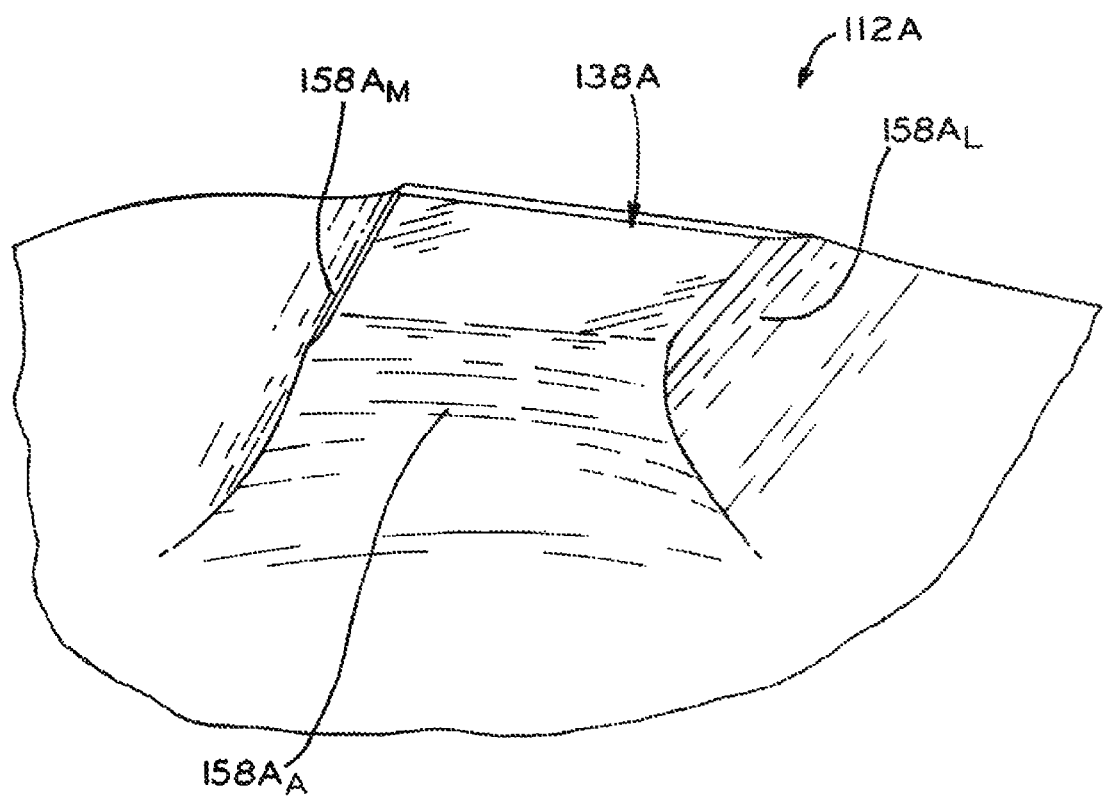
FIG. 6E is a fragmentary, anterior perspective view of a prior art ultracongruent (UC) tibial bearing component, illustrating a posterior eminence thereof (where prior art devices are listed as "predicate")

By contrast, the prior art Zimmer Natural Knee Flex Ultracongruent knee prosthesis, available from Zimmer, Inc. of Warsaw, Ind. includes prior art tibial bearing component 112A having posterior eminence 138A having areas which define a radius of less than 1 mm, as shown in FIG. 6E. The angle formed between lateral and medial sidewall portions $158A_L$, $158A_M$ of posterior eminence 138A is substantially less than angle $\mu_T$ defined by posterior eminence 138. More particularly, the prior art angle is 9-12 degrees, while angle $\mu_T$ is between 21 and 23 degrees as noted above. Further, the intercondylar walls of the prior art femoral component designed for use with prior art tibial bearing component 112A (not shown) has parallel intercondylar walls, i.e., no angle is formed between the intercondylar walls. Moreover, the distance between posterior eminence 138A and the anterior edge of the intercondylar notch of the prior art femoral component is larger than the corresponding distance defined by eminence 138 and anterior wall $155_A$ of the intercondylar notch of femoral component 120 (FIG. 6D), such that the prior art Zimmer Natural Knee Flex Ultracongruent knee prosthesis lacks the capability for hyperextension "beaching" as described above.

Turning back to FIG. 6C, medial/lateral stability is provided by the sloped surface provided by sidewall 158, and more particularly the height $H_E$ of proximal surface 156 over distal-most points 142, 144, of medial and lateral articular compartments 116, 118. However, such stability is primarily desired for early flexion and is not needed in deeper levels of flexion. Accordingly, posterior eminence 138 is sized and shaped to cooperate with intercondylar notch 154 to provide steadily decreasing levels of medial/lateral constraint starting from a maximum at full extension and transition to a minimum at 90 degrees flexion, after which such constraint is no longer needed.

More particularly, as illustrated in FIG. 6A, lateral and medial sidewalls $155_L$, $155_M$ of intercondylar notch 154 diverge posteriorly from the anterior terminus of notch 154 (at anterior wall $155_A$), such that the effective width between lateral and medial sidewalls $155_L$, $155_M$ becomes steadily greater than posterior eminence 138 as flexion progresses. Thus, additional medial/lateral space between posterior eminence 138 and intercondylar notch becomes available as prosthesis 110 is transitioned into deeper flexion. An exemplary femoral component with such a divergent intercondylar notch is described in: U.S. Provisional Patent Application Ser. No. 61/561,658, filed on Nov. 18, 2011 and entitled FEMORAL COMPONENT FOR A KNEE PROSTHESIS WITH IMPROVED ARTICULAR CHARACTERISTICS; U.S. Provisional Patent Application Ser. No. 61/579,873, filed on Dec. 23, 2011 and entitled FEMORAL COMPONENT FOR A KNEE PROSTHESIS WITH IMPROVED ARTICULAR CHARACTERISTICS; U.S. Provisional Patent Application Ser. No. 61/592,575 filed on Jan. 30, 2012 and entitled FEMORAL COMPONENT FOR A KNEE PROSTHESIS WITH IMPROVED ARTICULAR CHARACTERISTICS; U.S. Provisional Patent Application Ser. No. 61/594,113 filed on Feb. 2, 2012 and entitled FEMORAL COMPONENT FOR A KNEE PROSTHESIS WITH IMPROVED ARTICULAR CHARACTERISTICS; U.S. Provisional patent application Ser. No. 61/621,370 filed on Apr. 6, 2012 and entitled FEMORAL COMPONENT FOR A KNEE PROSTHESIS WITH IMPROVED ARTICULAR CHARACTERISTICS; U.S. Provisional Patenet Application Ser. No. 61/621,372, filed on Apr. 6, 2012 and entitled FEMORAL COMPONENT FOR A KNEE PROSTHESIS WITH IMPROVED ARTICULAR CHARACTERISTICS; U.S. Provisional Patent Application Ser. No. 61/621,373, filed on Apr. 6, 2012 and entitled FEMORAL COMPONENT FOR A KNEE PROSTHESIS WITH IMPROVED ARTICULAR CHARACTERISTICS; U.S. patent application Ser. No. 13/459,061 filed on Apr. 27, 2012, now issued as U.S. Pat. No. 9,060,868, and entitled FEMORAL COMPONENT FOR A KNEE PROSTHESIS WITH IMPROVED ARTICULAR CHARACTERISTICS; U.S. patent application Ser. No. 13/459,064 filed on Apr. 27, 2012, now issued as U.S. Pat. No. 8,932,365, and entitled FEMORAL COMPONENT FOR A KNEE PROSTHESIS WITH IMPROVED ARTICULAR CHARACTERISTICS; and in U.S. patent application Ser. No. 13/459,060 filed on Apr. 27, 2012, now issued as U.S. Pat. No. 9,308,095, and entitled FEMORAL COMPONENT FOR A KNEE PROSTHESIS WITH IMPROVED ARTICULAR CHARACTERISTICS. The entire disclosures of each of the above-identified patent applications are hereby expressly incorporated herein by reference.

Posterior eminence 138 has a limited anterior/posterior extent which also operates to effect disengagement of posterior eminence 138 from intercondylar notch 154 at a desired level of prosthesis flexion, as described in detail below.

Thus, advantageously, posterior eminence 138 is shaped to cooperate with intercondylar notch 154 to be functional only where its medial/lateral stability function is desired, and to avoid interaction with intercondylar notch 154 where such function is no longer required. As compared to predicate posterior eminences, posterior eminence 138 accomplishes this balance by having a rounded shape that is complementary to intercondylar notch 154 of femoral component 120 as described above. For example, the prior art Natural Knee Flex Ultracongruent knee prosthesis, available from Zimmer, Inc. of Warsaw, Ind., includes a tibial bearing component 112A (FIG. 6E) having a posterior eminence 138A which does not "interfit" with the corresponding femoral component in the manner described above.

In the illustrated embodiment of FIG. 6C, proximal surface 156 is substantially flat and/or planar and rises above distal-most points 144, 142 by a height $H_E$. In an exemplary embodiment, height $H_E$ is between 3.8 mm and 5.5 mm. However, it is contemplated that height $H_E$ may be as high as 10 mm, provided that anterior wall $155_A$ is appropriately angled so as to prevent presentation of a non-ramped surface to anterior portion $158_A$ of sidewall 158 of femoral intercondylar notch 154 during hyperextension.

By contrast, a traditional "cruciate retaining" tibial bearing component 212 (FIGS. 7A and 7B, described herein) includes intercompartmental eminence 238 which defines a reduced height $H_E'$ and is not flat or planar in its proximal surface. In an exemplary embodiment, height $H_E'$ of intercompartmental eminence is between 3.7 mm and 5.2 mm across a family of prosthesis sizes, but may have an alternative range of 2.0 mm-5.5 mm in some embodiments.

Further, posterior eminence 138 is distinguished from spine 38 of posterior-stabilized tibial bearing component (FIG. 5A) in that posterior eminence 138 is substantially shorter and defines a posterior surface that is non-articular. In an exemplary embodiment, for example, spine 38 protrudes proximally from the surrounding articular surface by at least 21 mm.

It is contemplated that posterior eminence 138 may define an increased height $H_E''$, and may include a rounded proximal surface 156' within the scope of the present disclosure. More particularly, increased height $H_E''$ and rounded proximal surface 156' may be sized and shaped to match the distal end of the patellofemoral groove of femoral component 120, such that sidewalls 158' and proximal surface 156' make continuous contact around the adjacent periphery of the patellofemoral groove in hyperextension. Advantageously, this full-area contact may further reduce the contact pressures and impact magnitude experienced by posterior eminence 138 when femoral component 120 is hyperextended.

Posterior eminence 138 defines an anterior/posterior extent $AP_{PE}$, which may be expressed in absolute terms or as a percentage of the corresponding overall anterior/posterior extent $AP_{UC}$ of ultracongruent tibial bearing component 112. For purposes of the present disclosure, anterior/posterior extent $AP_{UC}$ is measured at the same medial/lateral position as a sagittal plane bisecting posterior eminence 138. Across an exemplary range of sizes of tibial bearing component 112, anterior/posterior extent $AP_{PE}$ of posterior eminence 138 may be as little as 5 mm, 6 mm or 7 mm, and as much as 11 mm, 13 mm or 15 mm, or may be any value within any range defined by any of the foregoing values. This range of anterior/posterior extents $AP_{PE}$ correspond to a range of percentages of overall anterior/posterior extent $AP_{UC}$ for the respective sizes of tibial bearing component 112 that is as little as 10% or 18.7% and as much as 20.5% or 30%, or any percentage within any range defined by any of the foregoing values.

8. Soft Tissue Accommodation: Anterior/Lateral Relief Scallop.

Referring back to FIG. 7B, an anterior/lateral corner of tibial bearing component 212 may have material removed near the proximal edge thereof to create scallop 268. Scallop 268 creates extra space for the adjacent iliotibial (IT) band, which could potentially impinge upon tibial bearing component 212 in some patients. In an exemplary embodiment, scallop 268 extends around the entirety of the anterior/lateral corner of tibial bearing component 212. A detailed discussion of how the anterior/lateral corner of tibial prosthesis components are defined, and the advantages of pulling such corners away from the bone periphery, may be found in U.S. Patent Application Publication No. 2012/0022659 filed Jul. 22, 2011 and entitled "ASYMMETRIC TIBIAL COMPONENTS FOR A KNEE PROSTHESIS", the entire disclosure of which is hereby expressly incorporated herein by reference. Advantageously, scallop 268 may be used in lieu of or in addition to an anterior/lateral pullback to avoid or minimize the impact of potential impingement of the iliotibial band on such corner.

Scallop 268 extends inwardly into the area of lateral articular compartment 218, and downwardly toward the distal, baseplate-contacting surface of tibial bearing component 212. Thus, scallop 268 is a chamfer or fillet-like void in the periphery of tibial bearing component 212 which creates a space that may be occupied by nearby soft tissues that would otherwise impinge upon such periphery. Scallop 268 may extend distally almost to the distal baseplate-contacting surface, or may extend a lesser amount distally. The inward (i.e., medial and posterior) extent of scallop into lateral articular compartment 218 may be approximately equal to the distal extent, or may deviate from the distal extent. In an exemplary embodiment, scallop 268 occupies a 10-degree angular sweep around the anterior/lateral portion of the periphery of lateral articular compartment 218.

It is also contemplated that similar scallops or relief spaces may be provided around the periphery of tibial bearing component 212 to accommodate other adjacent soft tissues, such as the medial collateral ligament (MCL) and the lateral collateral ligament (LCL). Scallop 268 and any other scallops positioned for relief around other soft tissues are sufficiently sized and shaped to provide relief space for the intended soft tissue throughout a full range of flexion, and for a wide variety of patients.

9. Soft Tissue Accommodation: Anterior/Medial Bulbous Flare.

Figure 8A:
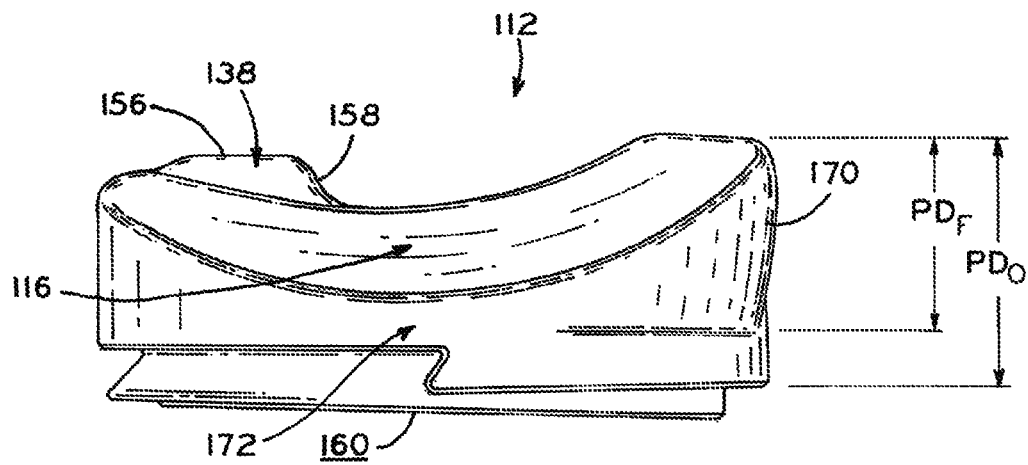
FIG. 8A is a side, elevation view of another ultracongruent (UC) tibial bearing component in accordance with the present disclosure, illustrating an anterior medial bulbous flare.
Figure 8B:
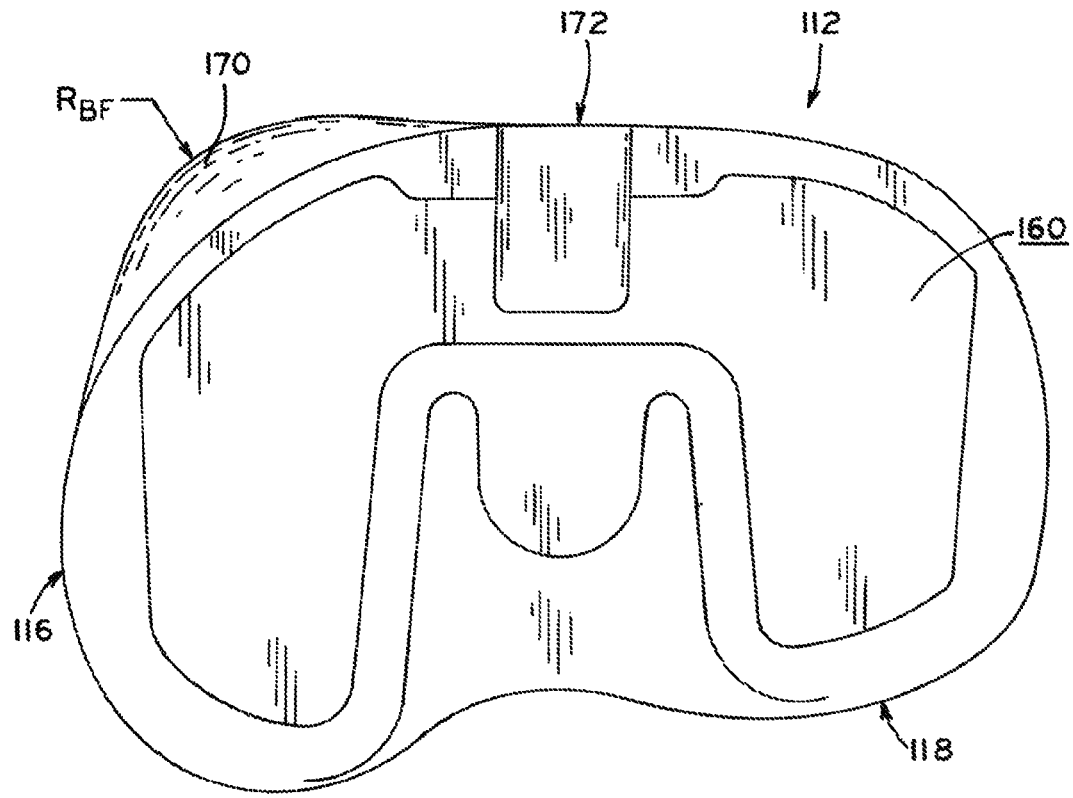
FIG. 8B is a bottom plan view of the tibial bearing component show in FIG. 8A.

Referring now to FIGS. 8A and 8B, ultra-congruent type tibial bearing component 112 is illustrated with a convex, bulbous flare 170 extending outwardly from peripheral sidewall 172. As described in detail below, flare 170 provides additional strength to medial compartment 116 at the anterior end thereof and protects adjacent soft tissues from abrasion, particularly the patellar tendon.

Most of sidewall 172 extends generally vertically (i.e., in a proximal-distal direction) between the distal, baseplate-contacting surface 160 (FIG. 8B) and the proximal articular surfaces of tibial bearing component 112. Accordingly, a majority of the periphery of baseplate contacting surface 160 substantially fits within the proximal periphery of the associated tibial baseplate (i.e., baseplate 14 shown in FIG. 1A). A detailed discussion of matching peripheries between a tibial baseplate and associated tibial bearing component may be found in U.S. Patent Application Publication No. 2012/0022659 filed Jul. 22, 2011 and entitled "ASYMMETRIC TIBIAL COMPONENTS FOR A KNEE PROSTHESIS", the entire disclosure of which is hereby expressly incorporated herein by reference.

Additionally, most of the outer periphery of the proximal articular surfaces of tibial bearing component 112 substantially matches the corresponding outer periphery of the distal (i.e., baseplate contacting) surface 160. However, bulbous flare 170 extends beyond the anterior/medial periphery of baseplate contacting surface 160, and therefore also extends beyond the corresponding periphery of the associated tibial baseplate when tibial bearing component 112 is fixed thereto (such as is shown in FIG. 1A in the context of tibial bearing component 12). Bulbous flare 170 thereby enables medial articular compartment 116 to "overhang" or extend anteriorly and medially beyond the periphery of tibial baseplate 14. Advantageously, this overhang allows an expanded anterior/medial and proximal reach of medial articular compartment 116, while obviating the need for a larger tibial baseplate. Avoiding the use of a larger baseplate size advantageously prevents overhang of tibial baseplate 14 over a small patient bone, while the bulbous flare 170 of tibial bearing component 112 preserves a relatively large articular surface. Accordingly, tibial components incorporating bulbous flare 170 are particularly suited to tibial prostheses for use in small stature patients, whose tibias commonly present a small proximal tibial resected surface which necessitates the use of a correspondingly small tibial baseplate 14.

As shown in FIG. 8A, bulbous flare 170 includes a convex curvature which extends up and around the proximal edge of medial articular compartment 116. Advantageously, this convex profile and associated soft proximal edge presents only large-radius, "soft" edges to the patellar tendon, particularly in deep flexion prosthesis configurations. In one exemplary embodiment, the convex curvature defined by bulbous flare 170 defines a flare radius $R_{BF}$ (FIG. 8B) of at least 10 mm, which extends around a partially spherical surface. However, it is contemplated that bulbous flare 170 may also be formed as a complex shape incorporating multiple radii, such that bulbous flare 170 may be defined by any surface with convexity in transverse and sagittal planes.

Referring now to FIG. 8A, another quantification for the broadly convex, soft-tissue friendly nature of flare 170 is the portion of proximal/distal extent $PD_O$ of the adjacent portion of sidewall 172 that is occupied by proximal/distal extent $PD_F$ of flare 170. In an exemplary embodiment, proximal/distal extent $PD_O$ is the portion of peripheral sidewall 172 of tibial bearing component not covered by tibial baseplate 14 when tibial bearing component 12 is assembled thereto, and proximal/distal extent $PD_F$ of the convexity of flare 170 occupies at least 80% of a proximal/distal extent $PD_O$.

Also advantageously, the additional material afforded by bulbous flare 170 at the anterior/medial portion of sidewall 172 provides a buttress for the anterior edge of medial articular compartment 116, thereby enabling tibial bearing component 112 to readily absorb substantial anteriorly-directed forces applied by the femur during prosthesis use.

Yet another advantage provided by the increased size of medial articular compartments 116 through use of flare 170 is that a larger femoral component 120 may be used in conjunction with a given size of tibial prosthesis. For some patients, this larger femoral/smaller tibial prosthesis arrangement may provide a closer match to a health a knee configuration, and/or enhanced articulation characteristics.

Still another advantage to the convex, bulbous shape of flare 170 is that the soft, rounded appearance thereof minimizes the visual impact of an increased proximal height of medial articular compartment 116 and the increased anterior extent thereof past the periphery of baseplate contacting surface 160. This minimized visual impact allows sufficient levels of buttressing material to be added to the anterior/medial portion of sidewall 172 while preserving surgeon confidence that the overhang of flare 170 past baseplate contacting surface 160 is appropriate.

10. Bone Conservation and Component Modularity: Variable Component Surface Geometries.

As illustrated in FIG. 4A, medial and lateral articular compartments 16, 18 of tibial bearing component 12 define substantially equal material thicknesses between their respective superior, dished articular surfaces and opposing distal (i.e. inferior) surface 60. Stated another way, the coronal "thickness profiles" of medial and lateral articular compartments 16, 18 are substantial mirror images of one another about a sagittal bisecting tibial bearing component 12.

Figure 9A:
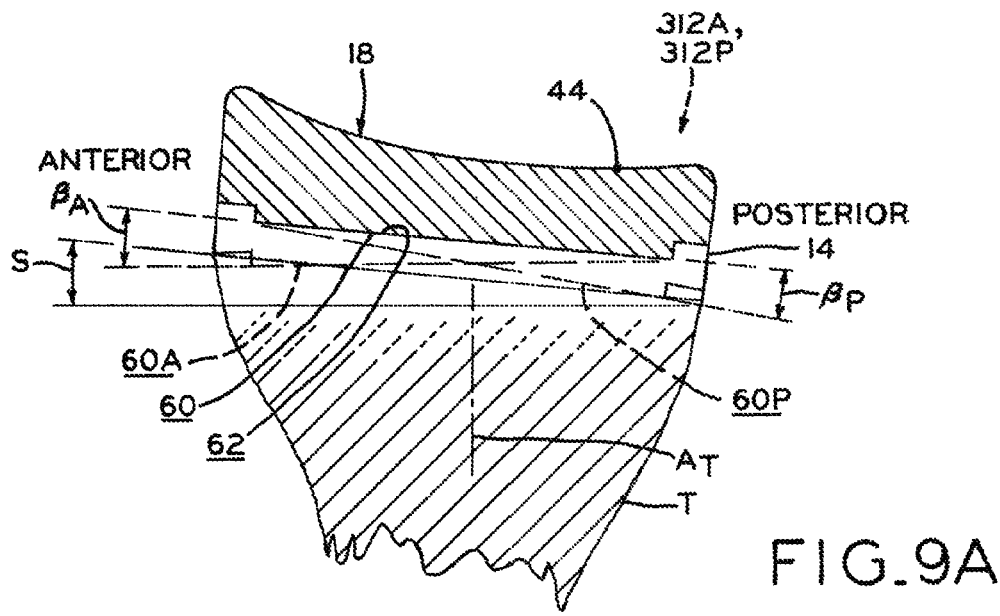
FIG. 9A is a sagittal, cross-sectional view of a tibial bearing component in accordance with the present disclosure, illustrating geometric changes to the distal surface of the tibial bearing component which affect the anterior/posterior orientation of the tibial articular surfaces with respect to the tibia.
Figure 9D:
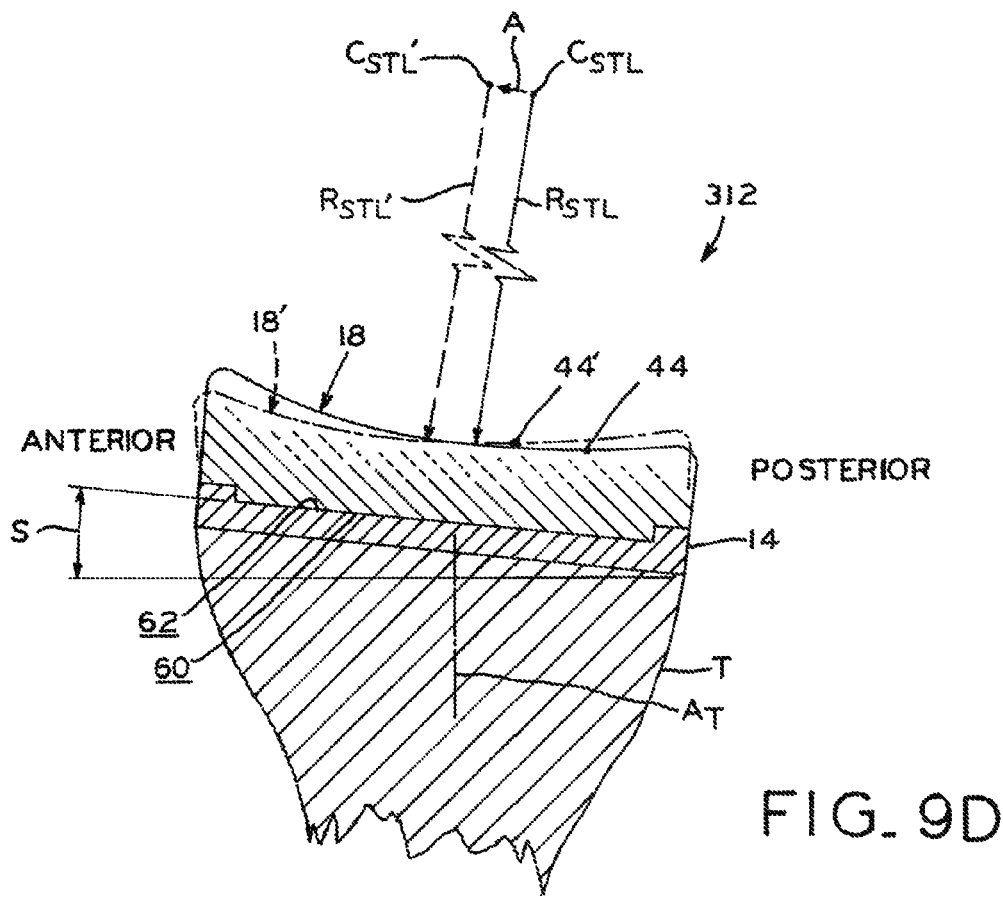
FIG. 9D is a sagittal, cross-sectional view of a tibial bearing component in accordance with the present disclosure, illustrating geometric changes to the articular surface of the tibial bearing component which affect the anterior/posterior orientation of the tibial articular surfaces with respect to the tibia.
Figure 9B:
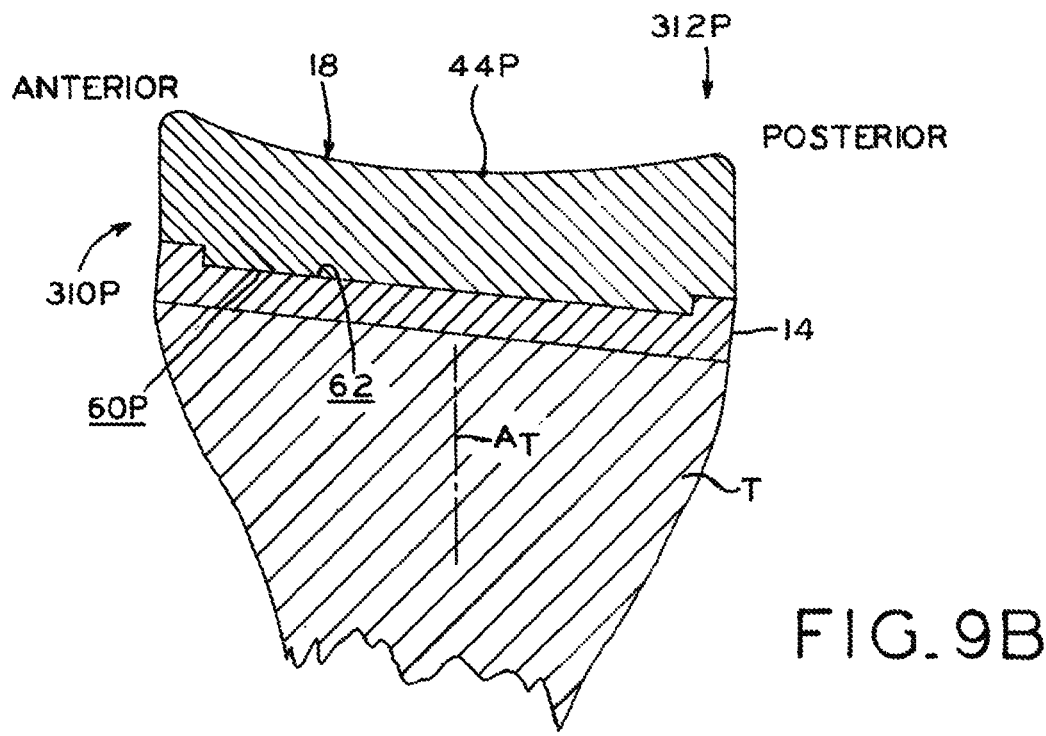
FIG. 9B is a sagittal, cross-sectional view of the tibial bearing component of FIG. 9A, in which the geometric changes to the tibial bearing component replicate a decrease in the anteroposterior slope defined by the resected surface of the tibia.
Figure 9C:
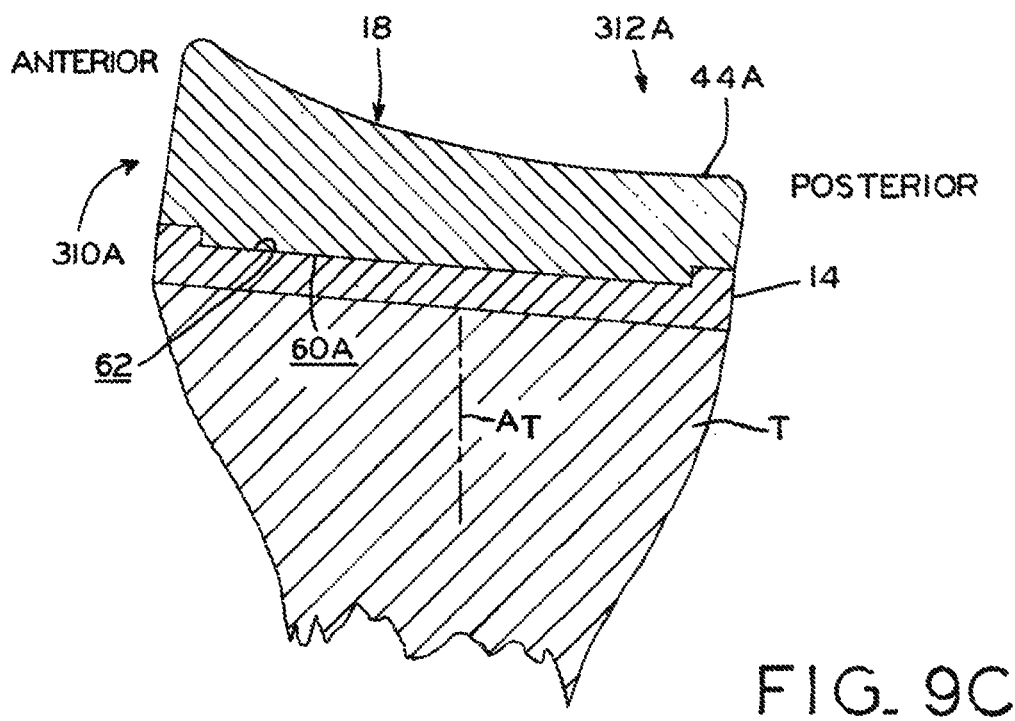
FIG. 9C is a sagittal, cross-sectional view of the tibial bearing component of FIG. 9A, in which the geometric changes to the tibial bearing component replicate an increase in the anteroposterior slope defined by the resected surface of the tibia.
Figure 10A:
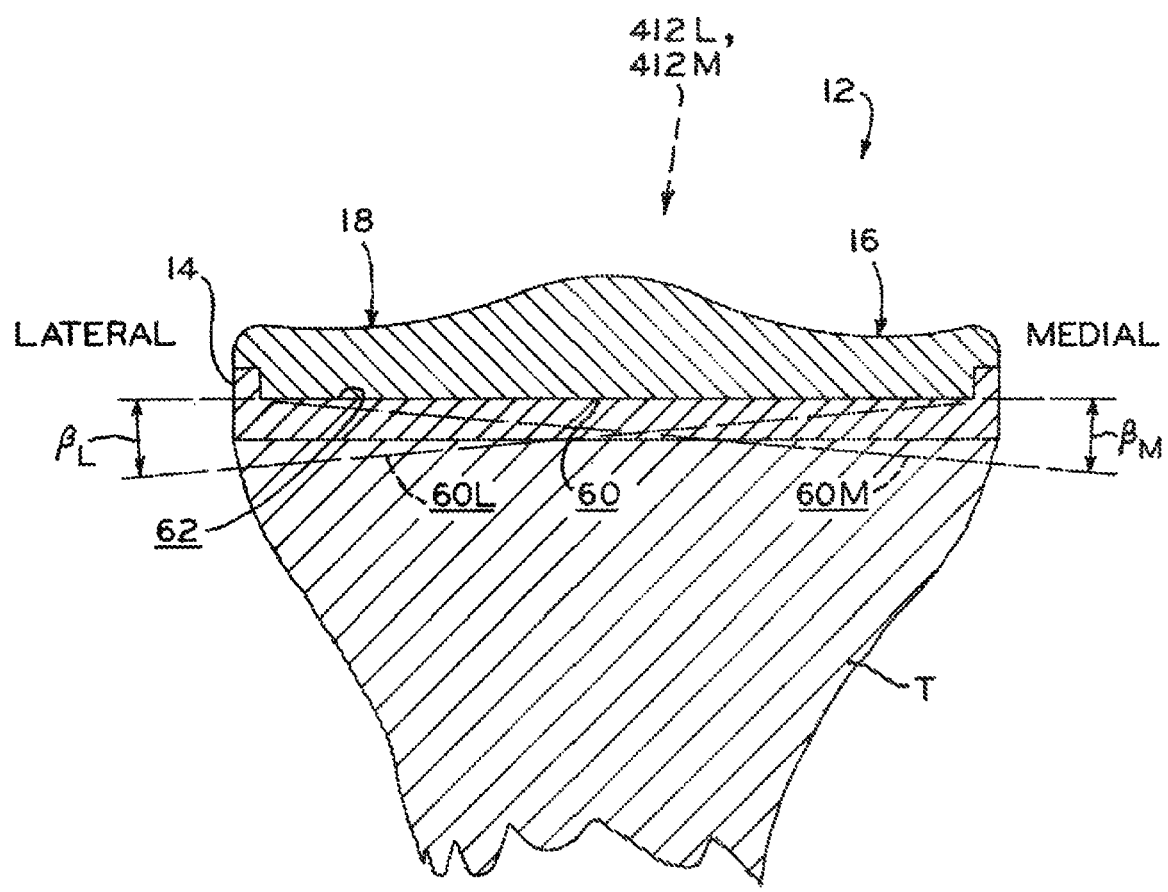
FIG. 10A is a coronal, cross-sectional view of a tibial bearing component in accordance with the present disclosure, illustrating potential geometric changes to the distal surface of the tibial bearing component which affect the medial/lateral orientation of the tibial articular surfaces with respect to the tibia.
Figure 10B:
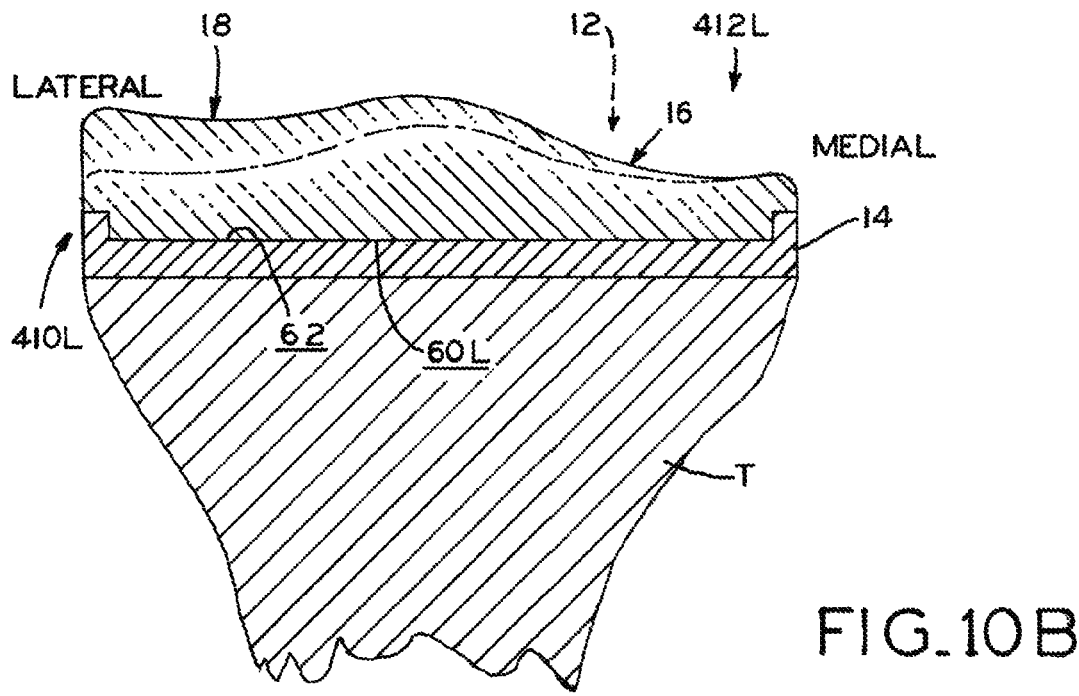
FIG. 10B is a coronal, cross-sectional view of an alternative tibial bearing component, in which one of the potential geometric changes to the bearing component shown in FIG. 10A is effected to compensate for a valgus deformity.
Figure 10C:
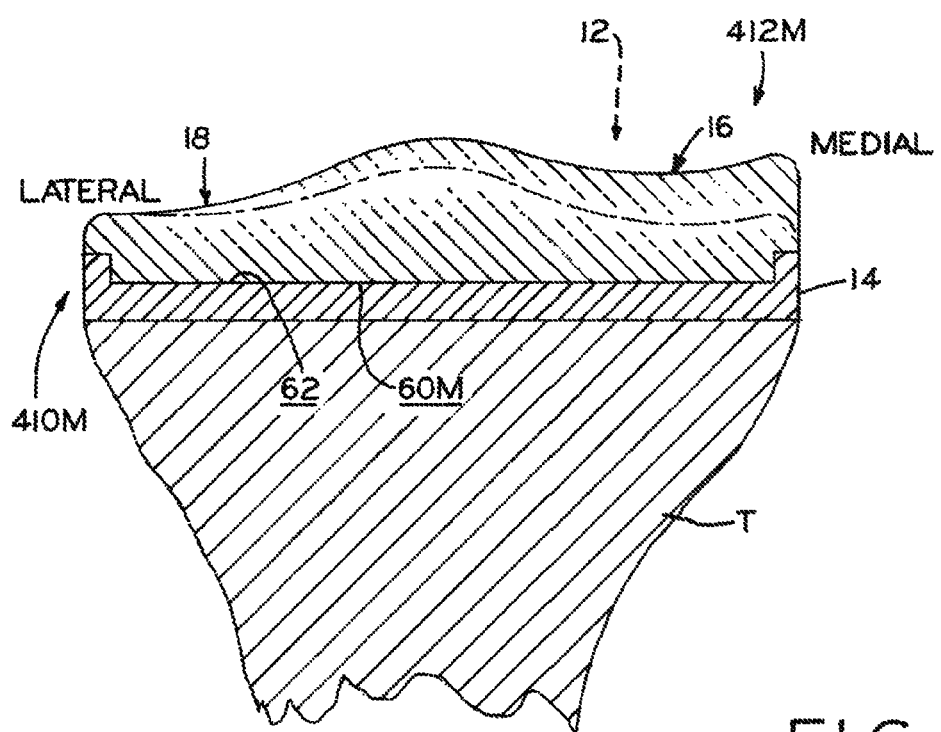
FIG. 10C is a coronal, cross-sectional view of an alternative tibial bearing component, in which one of the potential geometric changes to the bearing component shown in FIG. 10A is effected to compensate for a valgus deformity.

For purposes of the present disclosure, a thickness profile of tibial bearing component 12 may be defined as the changing material thicknesses of medial and/or lateral articular compartments 16, 18 across a defined cross-sectional extent, such as an anterior/posterior extent in a sagittal cross-section (FIGS. 9A-9D) or a medial/lateral extent in a coronal cross-section (FIGS. 10A-10C).

Thus, in addition to the coronal thickness profiles shown in FIG. 4A, medial and lateral articular compartments 16, 18 of tibial bearing component 12 define sagittal thickness profiles (FIGS. 3A and 3B, respectively) between the superior dished articular surfaces of medial and lateral articular compartments 16, 18 and distal surface 60. These sagittal thickness profiles cooperate with anterior/posterior slope S defined by the proximal respective surface of tibia T (described in detail above) to define the anterior/posterior locations of medial and lateral distal-most points 42, 44, respectively. Thus, distal-most points 42, 44 may shift anteriorly or posteriorly in response to a change in the sagittal thickness profile or tibial slope S, or both.

In alternative embodiments of tibial bearing component 12, shown generally in FIGS. 9A-10C, the orientation of distal surface 60 with respect to the superior articular surfaces of medial and lateral articular compartments 16, 18 may be reconfigured. This reconfiguration alters the spatial relationship of distal surface 60 to the articular surfaces, thereby effecting a change in the orientation of such articular surfaces with respect to the proximal resected surface of tibia T. As described below, this spatial alteration may be used to offer alternative bearing component designs tailored to the specific needs of some patients, while avoiding the need to recut or otherwise alter the geometry of the proximal tibia.

Referring now to FIG. 9A, one potential geometric reconfiguration of tibial bearing component 12 is alteration of the sagittal thickness profile to increase or decrease the anterior/posterior "tilt" of the proximal articular surfaces of medial and lateral articular compartments 16, 18. For simplicity, only lateral articular compartment 18 is shown in FIGS. 9A-9D and described detail below, it being understood that a similar geometric reconfiguration can be applied to medial compartment 16 in a similar fashion.

For example, if a surgeon wishes to tilt tibial bearing component 12 forward (such as to shift distal-most points 42, 44 anteriorly), he or she may recut the proximal tibia to reduce tibial slope S. Similarly, increasing tibial slope Stilts tibial bearing component 12 backward and posteriorly shifts distal-most points 42, 44. However, a similar "tilting" of the tibial articular surface and shifting of sagittal distal-most points, may be accomplished without altering tibial slope S by using alternative tibial bearing components in accordance with the present disclosure, as described below. For example, where the superior articular surfaces of regular and alternative bearing components share a common overall curvature and geometry, differing sagittal thickness profiles in the alternative component effects the same articular changes normally achieved by a change in tibial slope S.

Referring to FIG. 9D, one exemplary alternative tibial bearing component 312 is shown superimposed over tibial bearing component 12, with distal surfaces 60 aligned such that changes to the articular surface of lateral articular compartment 18 are illustrated. Tibial bearing component 312 features a sagittal radius $R_{STL}'$ defining radius center $C_{STL}'$ which is anteriorly shifted along direction A with respect to sagittal radius $R_{STL}$ and radius center $C_{STL}$ of tibial bearing component 12. This anterior shift reconfigures the spatial relationship of the articular surface of lateral articular compartment 18 with respect to distal surface 60. More particularly, this anterior shift mimics a reduction in tibial slope S, because alternative lateral articular compartment 18' defines an articular surface which is "anteriorly tilted" so as to shift distal-most point 44 anteriorly to the alternative distal-most point 44', as shown in the dashed-line articular surface profile of FIG. 9D. Conversely, center $C_{STL}$ of radius $R_{STL}$ could be shifted posteriorly to mimic an increase in posterior slope S by causing a posterior shift of distal-most point 44.

When center $C_{STL}$ is anteriorly shifted to alternative center $C_{STL}'$, the resulting articular surface may not be identical to its non-shifted counterpart. However, the articular characteristics of tibial bearing components 12, 312 will be comparable, provided an offsetting change in anterior slope S is made to place distal-most points 44, 44' at the same anterior/posterior position. Thus, a family of tibial bearing components may be provided in which one component in the family has an anteriorly shifted center $C_{STL}$ as compared to the other component in the family. Depending on a surgeon's choice of anterior slope 5, the surgeon may intraoperatively choose from the family of components to accommodate the chosen slope S and place the distal-most points of articular compartments 16, 18 at a desired anterior/posterior location. To this end, components within the family may have identical distal surfaces 60 such that each component in the family can be mounted to a common tibial baseplate 14.

Turning back to FIG. 9A, other alternative tibial bearing components 312A, 312P are shown superimposed over tibial bearing component 12, with articular compartment 18 aligned such that changes in distal surfaces 60, 60A, 60P are illustrated. For example, bearing component 312A selectively thickens portions of the sagittal thickness profile of lateral articular compartment 18, thereby angling the distal surface thereof with respect to the superior articular surfaces. Alternative distal surface 60A defines angle with respect to distal surface 60 of tibial bearing component 12. As compared with the unaltered bearing component 12, bearing component 312A progressively adds material to distal surface 60 along a posterior-to-anterior direction, such a minimum amount of added material is present at the posterior-most portion of distal surface 60 and a maximum amount of added material is present at the anterior-most portion of distal surface 60. However, alternative distal surface 60A is otherwise identical to distal surface 60, such that either of distal surfaces 60, 60A can be mounted to the same tibial baseplate.

Thus, the added material which defines distal surface 60A of tibial bearing component 312A operates in the manner of a wedge-shaped shim placed between distal surface 60 and the adjacent superior surface 62 of tibial baseplate 14, except that the added material of component 312A is unitarily or monolithically formed therewith. As shown by a comparison of FIGS. 9A and 9C, this wedge-shaped added material tilts the articular surface of lateral articular compartment 18 posteriorly (i.e., the posterior portion of component 312A shifts distally relative to the anterior portion), thereby shifting distal-most point 44 posteriorly to alternative distal-most point 44A. As compared to bearing component 12, the magnitude of the posterior tilt (and therefore, of the posterior low-point shift) is controlled by increasing or decreasing angle $\beta_A$ (FIG. 9A).

Conversely, tibial bearing component 312P (FIG. 9B) progressively adds material along an anterior-to-posterior direction, thereby adding a wedge-shaped portion of extra material to component 312P to define distal surface 60P. Distal surface 60P is also identical to distal surface 60, such that component 312P can be attached to tibial baseplate 14. When so attached, the superior articular surface of lateral articular compartment 18 is anteriorly tilted (i.e., the anterior portion of component 312P shifts distally relative to the posterior portion). As illustrated by a comparison of FIGS. 9A and 9B, distal-most point 44 is shifted anteriorly to alternative distal-most point 44P. As compared to bearing component 12, the magnitude of the anterior tilt (and therefore, of the anterior low-point shift) is controlled by increasing or decreasing angle $\beta_P$ (FIG. 9A).

A similar selective thickening of tibial bearing component 12 may be employed to provide alternative bearing components which allow a surgeon to intraoperatively correct for varus/valgus deformities. Referring now to FIG. 10A, alternative tibial bearing components 412L, 412M define distal surfaces 60L, 60M which progressively add material along medial-to-lateral and lateral-to-medial directions, respectively, as compared to distal surface 60 of tibial bearing component 12. As with alternative surfaces 60A, 60P, distal surfaces 60L, 60M are otherwise identical to distal surface 60 such that any of components 12, 412M, 412L can be mounted to a common tibial baseplate 14.

Distal surface 60L defines angle $\beta_L$, with distal surface 60, effectively placing the thickest part of a wedge-shaped shim of additional material underneath lateral articular compartment 18. Conversely, distal surface 60M defines angle $\beta_M$ with distal surface 60, such that the increased thickness of the coronal cross-sectional profile is concentrated underneath the medial articular compartment 16.

FIG. 10B illustrates tibial prosthesis 410L, which includes alternative tibial bearing component 412L having distal surface 60L mounted to superior surface 62 of tibial baseplate 14. Bearing component 412L is juxtaposed the profile of tibial bearing component 12, which is shown in dashed lines. As illustrated, the superior articular surfaces of medial and lateral articular compartments 16, 18 are tilted medially with respect to the resected surface of tibia T (i.e., the medial portion of component 412L shifts distally relative to the lateral portion) when tibial bearing component 412L is attached to tibial baseplate 14. Bearing component 412L defining such a medial tilt may be employed, for example, to intraoperatively correct for a varus deformity in the knee of the patient without altering the geometry of the proximal tibial cut surface or replacing tibial baseplate 14. The magnitude of the medial tilt is controlled by increasing or decreasing angle $\beta_L$ (FIG. 10A).

Turning to FIG. 10C, another alternative tibial bearing component 412M is shown juxtaposed against the dashed line profile of tibial bearing component 12. Bearing component 412M is similar to component 412L discussed above, except that distal surface 60M features a lateral tilt (i.e., the lateral portion of component 412M shifts distally relative to the medial portion) when tibial bearing component 412M is attached to tibial baseplate 14. Bearing component 412M defining such a lateral tilt may be employed, for example, to intraoperatively correct for a valgus deformity in the knee of the patient without altering the geometry of the proximal tibial cut surface or replacing tibial baseplate 14. The magnitude of the lateral tilt is controlled by increasing or decreasing angle $\beta_M$ (FIG. 10A).

In an exemplary embodiment, a set or family of tibial bearing components may be provided which includes any combination of tibial bearing components 12, 312A, 312P, 412M, and 412L. Further, multiple versions of components 312A, 312P, 412L, 412M may be provided, in which each version defines a unique value for angles $\beta_A$, $\beta_P$, $\beta_L$, $\beta_M$ respectively. When provided with such a family of components, a surgeon may intraoperatively select a tibial bearing component which positions distal-most points 42, 44 at a desired location, and/or corrects for varus or valgus deformities, without having to alter tibial slope S or change tibial baseplate 14. In an exemplary embodiment, the geometry and curvature of the superior dished articular surfaces of medial and lateral articular compartments 16, 18 will be identical for all components provided in the kit, such that no other changes to the articular characteristics of the tibial bearing component intermingle with the changes brought on by altering the thickness profile as described above.

While the alternative tibial baseplates described above have either reconfigured sagittal thickness profiles or reconfigured coronal thickness profiles, it is contemplated that tibial bearing components may be provided which incorporate reconfigurations to both the sagittal and coronal thickness profiles within a single tibial bearing component. Moreover, it is contemplated that any appropriate thickness profile or set of thickness profiles may be provided as required or desired for a particular application.

Thus, a family of tibial bearing components provided in accordance with the present disclosure obviates any need for a surgeon to recut the proximal surface of tibia T, and allows the surgeon to permanently implant tibial baseplate 14 while also preserving the intraoperative option to 1) alter the anterior/posterior tilt of the articular surfaces of medial and lateral articular compartments 16, 18, and/or 2) alter the medial/lateral tilt or the articular surfaces, such as for correction of a varus/valgus deformity.

Moreover, it is appreciated that a tibial bearing component in accordance with the present disclosure may be provided in a single-component design, i.e., not part of a kit, while still being designed to "alter" the tilt of the superior articular surface. For example, the articular surface of an alternative bearing component may be designed to may mimic the articular surface of a "regular" tibial bearing component (such as component 12, described above), even though the two components are designed to cooperate with differing anteroposterior tibial slopes.

In some instances, for example, differing classes of tibial bearing component (e.g., ultracongruent and posterior-stabilized) are designed to be used with differing tibial slopes. However, a surgeon may wish to intraoperatively select between these differing component classes, which in turn may necessitate reclining of tibia T. However, in an exemplary embodiment, ultracongruent tibial bearing component 112 (FIGS. 6A through 6C) may include distal surface 160 which defines an anterior/posterior slope with respect to medial and lateral articular compartments 116, 118 which effectively "tilts" the articular surfaces thereof forward sufficiently to render ultracongruent tibial bearing component 112 compatible with tibial slope S (shown in FIGS. 3A and 3B and described in detail above) used for posterior-stabilized tibial bearing component 12.

For example, an ultracongruent-type tibial bearing component may be typically designed for use with a tibial slope S equal to 3 degrees, while other bearing component designs (e.g., posterior-stabilized designs) may use a 5 degree tibial slope S. In this situation, ultracongruent tibial bearing component 112 may be effectively "tilted anteriorly" by 2 degrees in the manner described above, such that the articular characteristics designed into the articular surfaces of tibial bearing component 112 are achievable with a 5-degree tibial slope S. Thus, a surgeon may make a proximal cut of tibia T to create an anteroposterior slope S of 5 degrees, for example, while achieving articular characteristics normally associated with a tibial slope of 3 degrees by implanting tibial bearing component 112 on tibial baseplate 14. Thus, a surgeon may have the freedom to choose intraoperatively between ultracongruent tibial bearing component 112 and posterior stabilized tibial bearing component 12 without having to alter tibial slope S or tibial baseplate 14.

Moreover, it is contemplated that changing thickness profiles or the moving the center of sagittal curvature of an articular surface as described above may be accomplished with any combination of cruciate-retaining, ultracongruent and/or posterior-stabilized designs.

While the present disclosure has been described as having exemplary designs, the present disclosure can be further modified within the spirit and scope of this disclosure. This application is therefore intended to cover any variations, uses or adaptations of the disclosure using its general principles. Further, this application is intended to cover such departures from the present disclosure as come within know or customary practice in the art to which this disclosure pertains.

What is claimed is:

1. A system for knee arthroplasty comprising:
a plurality of tibial bearing components including at least a first tibial bearing component from a first tibial bearing component class and a second tibial bearing component from a second tibial bearing component class that differs from the first tibial bearing component class, the first tibial bearing component and the second tibial bearing component including:
an articular surface including medial and lateral dished articular compartments sized and shaped for articulation with a medial femoral condyle and lateral femoral condyle, respectively;
a distal surface opposing the articular surface, wherein the distal surface of the first tibial bearing component is substantially similar to the distal surface of the second tibial bearing component such that both the first tibial bearing component and the second tibial bearing component are mountable to a common tibial tray; and
a sagittal radius extending along the articular surface in an anterior-posterior direction and the sagittal radius having a radius center, wherein the sagittal radius and the radius center of the first tibial bearing component differs with respect to the sagittal radius and the radius center of the second tibial bearing component.

2. The system of claim 1, wherein the articular surface of the first tibial bearing component is differently shaped relative to the articular surface of the second tibial bearing component.

3. The system of claim 1, wherein each of the plurality of tibial bearing components has a periphery that bounds the articular surface and the distal surface, and the periphery of each of the tibial bearing components is the same size and shape.

4. The system of claim 1, further comprising a single common tibial tray configured to interchangeably couple with each of the plurality of tibial bearing components and configured to mount to a resected proximal surface of the tibia with the proximal surface having any chosen anterior slope.

5. The system of claim 1, wherein the first tibial bearing component class includes two or more tibial bearing components, and wherein each of the two or more tibial bearing components from the first tibial bearing component class have a sagittal thickness profile that differs with respect to each of the other tibial bearing components from the first tibial bearing component class.

6. The system of claim 5, wherein the plurality of bearing components from the first tibial bearing component class comprising the two or more tibial bearing components progressively thicken relative to one another along one of a posterior-to-anterior direction and an anterior-to posterior direction.

7. The system of claim 6, wherein one of the plurality of bearing components from the first tibial bearing component class comprising the two or more tibial bearing components has a minimum amount of material at a posterior-most portion and a maximum amount of material at an anterior-most portion relative to others of the plurality of bearing components from the first tibial bearing component class comprising the two or more tibial bearing components.

8. The system of claim 7, wherein the articular surface of the one of the plurality of bearing components from the first tibial bearing component class comprising the two or more tibial bearing components is tilted posteriorly such that a posterior portion of the one of the plurality of bearing components from the first tibial bearing component class comprising the two or more tibial bearing components is shifted distally relative to an anterior portion, whereby a distal-most point of the articular surface of the one of the plurality of bearing components from the first tibial bearing component class comprising the two or more tibial bearing components is shifted posteriorly relative to distal-most points of others of the plurality of tibial bearing components from the first tibial bearing component class comprising the two or more tibial bearing components.

9. The system of claim 6, wherein one of the plurality of bearing components from the first tibial bearing component class comprising the two or more tibial bearing components has a maximum amount of material at a posterior-most portion and a minimum amount of material at an anterior-most portion relative to others of the plurality of bearing components from the first tibial bearing component class comprising the two or more tibial bearing components.

10. The system of claim 9, wherein the articular surface of the one of the plurality of bearing components from the first tibial bearing component class comprising the two or more tibial bearing components is tilted anteriorly such that a posterior portion of the one of the plurality of bearing components from the first tibial bearing component class comprising the two or more tibial bearing components is shifted proximally relative to an anterior portion, whereby a distal-most point of the articular surface of the one of the plurality of bearing components from the first tibial bearing component class comprising the two or more tibial bearing components is shifted anteriorly relative to distal-most points of others of the plurality of tibial bearing components from the first tibial bearing component class comprising the two or more tibial bearing components.

11. A method comprising:
resecting a proximal portion of a tibia to achieve a surface having a desired anterior slope;
mounting a tibial tray to the surface;
selecting from a plurality of tibial bearing components including at least a first tibial bearing component from a first tibial bearing component class and a second tibial bearing component from a second tibial bearing component class that differs from the first tibial bearing component class, the first tibial bearing component and the second tibial bearing component including:
an articular surface including medial and lateral dished articular compartments sized and shaped for articulation with a medial femoral condyle and lateral femoral condyle, respectively;
a distal surface opposing the articular surface, wherein the distal surface of the first tibial bearing component is identical to the distal surface of the second tibial bearing component such that both the first tibial bearing component and the second tibial bearing component are mountable to the tibial tray; and
a sagittal radius extending along the articular surface in an anterior-posterior direction and the sagittal radius having a radius center, wherein the sagittal radius and the radius center of the first tibial bearing component differs with respect to the sagittal radius and the radius center of the second tibial bearing component;

coupling one of the plurality of tibial bearing components to the tibial tray; and
testing one or more of a stability, a force balance, or a range of motion of a knee joint in which the one of the plurality of tibial bearing components is coupled to the tibial tray, the testing producing a testing result;
wherein when the testing result is not satisfactory, removing the one of the plurality of tibial bearing components from the tibial tray, while preserving the mounting of the tibial tray to the surface of the tibia; and
coupling second of the plurality of tibial bearing components to the tibial tray.

12. The method of claim 11, further comprising:
testing one or more of a stability, a force balance, or a range of motion of the knee joint in which the second of the plurality of tibial bearing components is coupled to the tibial tray.

13. The method of claim 11, wherein the first tibial bearing component class includes two or more tibial bearing components, and wherein each of the two or more tibial bearing components from the first tibial bearing component class have a sagittal thickness profile that differs with respect to each of the other tibial bearing components from the first tibial bearing component class.

14. The method of claim 13, wherein the plurality of bearing components from the first tibial bearing component class comprising the two or more tibial bearing components progressively thicken relative to one another along one of a posterior-to-anterior direction and an anterior-to posterior direction.

15. The method of claim 11, wherein the articular surface of the first tibial bearing component is differently shaped relative to the articular surface the second tibial bearing component.

16. The system of claim 1, wherein the first tibial bearing component class comprises a cruciate-retaining design and the second tibial bearing component class comprises an ultracongruent design or a posterior-stabilized design.

17. The system of claim 1, wherein the first tibial bearing component class comprises an ultracongruent design and the second tibial bearing component class comprises a cruciate-retaining design or a posterior-stabilized design.

18. The system of claim 1, wherein the first tibial bearing component class comprises a posterior-stabilized design and the second tibial bearing component class comprises a cruciate-retaining design or an ultracongruent design.

19. The method of claim 11, wherein the first tibial bearing component class comprises a cruciate-retaining design and the second tibial bearing component class comprises an ultracongruent design or a posterior-stabilized design.

20. The method of claim 11, wherein the first tibial bearing component class comprises an ultracongruent design and the second tibial bearing component class comprises a cruciate-retaining design or a posterior-stabilized design.

21. The method of claim 11, wherein the first tibial bearing component class comprises a posterior-stabilized design and the second tibial bearing component class comprises a cruciate-retaining design or an ultracongruent design.

* * * * *